US012667106B2

(12) United States Patent
Afriat-Jurnou et al.

(10) Patent No.: US 12,667,106 B2
(45) Date of Patent: Jun. 30, 2026

(54) STABILIZED MUTANTS OF QUORUM QUENCHING LACTONASE AND USE THEREOF IN TREATMENT OF PATHOGENS

(71) Applicant: Migal Galilee Research Institute Ltd., Kiryat Shmona (IL)

(72) Inventors: Livnat Afriat-Jurnou, Kfar-Szold (IL); Maayan Erov, Kfar Blum (IL); David Gurevich, Manara (IL); Mery Dafny Yelin, Merom Golan (IL)

(73) Assignee: Migal Galilee Research Institute Ltd., Kiryat Shmona (IL)

( * ) Notice: Subject to any disclaimer, the term of this patent is extended or adjusted under 35 U.S.C. 154(b) by 1113 days.

(21) Appl. No.: 17/596,740

(22) PCT Filed: Jun. 17, 2020

(86) PCT No.: PCT/IL2020/050673
§ 371 (c)(1),
(2) Date: Dec. 16, 2021

(87) PCT Pub. No.: WO2020/255131
PCT Pub. Date: Dec. 24, 2020

(65) Prior Publication Data
US 2023/0240305 A1 Aug. 3, 2023

Related U.S. Application Data

(60) Provisional application No. 62/862,348, filed on Jun. 17, 2019.

(51) Int. Cl.
| | |
|---|---|
| *A01N 63/50* | (2020.01) |
| *A01P 1/00* | (2006.01) |
| *C12N 9/18* | (2006.01) |
| *C12N 15/70* | (2006.01) |

(52) U.S. Cl.
CPC ................ *A01N 63/50* (2020.01); *A01P 1/00* (2021.08); *C12N 9/18* (2013.01); *C12N 15/70* (2013.01); *C12Y 301/01081* (2013.01); *C12Y 301/08001* (2013.01)

(58) Field of Classification Search
CPC ...................................................... C12N 9/18
See application file for complete search history.

(56) References Cited

U.S. PATENT DOCUMENTS

| | | | |
|---|---|---|---|
| 10,202,587 B2 * | 2/2019 | Chabriere | C12N 9/16 |
| 2019/0040369 A1 | 2/2019 | Chabriere et al. | |

FOREIGN PATENT DOCUMENTS

WO 2019027528 A1 2/2019

OTHER PUBLICATIONS

Hiblot et al., "Crystal structure of VmoLac, a tentative quorum quenching lactonase from the extremophilic crenarchaeon Vulcanisaeta moutnovskia", Scientific Reports, 2015, 5:8372. 11 pages. DOI: 10.1038/srep08372.*
Goldman et al., "The TIM Barrel Architecture Facilitated the Early Evolution of Protein-Mediated Metabolism", J. Molecular Evolution, 2016, 82:17-26. DOI 10.1007/s00239-015-9722-8.*
Afriat et al; The latent promiscuity of newly identified microbial lactonases is linked to a recently diverged phosphotriesterase:. Biochemistry. 45(46):pp. 13677-13686. (2006).
Arnold et al ; "*Pseudomonas syringae* pv. phaseolicola: From "has bean" to supermodel". Molecular Plant Pathology 12(7), pp. 617-627(2011).
Barnard "Salmond GPC.Quorum sensing in *Erwinia* species." Anal. Bioanal. Chem. 387(2):pp. 415-423. (2007).
Bhat et al; "Current status of post harvest soft rot in vegetables: A review". Asian Journal of Plant Science 9 (4): pp. 200-208. (2010).
Chen et al; "Quorum quenching enzymes and their application in degrading signal molecules to block quorum sensing-dependent infection"International Journal of Molecular Sciences 14. pp. 17477-17500. (2013).
Choi et al; "Secretory and extracellular production of recombinant proteins using *Escherichia coli*"Appl Microbiol Biotechnol64: pp. 625-635. (2004).
Conway et al; "Quorum-sensing signals and quorum-sensing genes in Burkholderia vietnamiensis". Journal of Bacteriology vol. 184. No.4 pp. 1187-1191. (2002).
Crépin et al.;"Quorum sensing signaling molecules produced by reference and emerging soft-rot bacteria (*Dickeya* and *Pectobacterium* spp.)". PLoS One vol. 7 Issue 4. (2012).
Crépin et al; "N-Acyl Homoserine Lactones in diverse Pectobacterium and Dickeya plant pathogens: Diversity, abundance, and involvement in virulence". Sensors 12. pp. 3484-3497. (2012).
Duerkop et al; "Quorum-sensing control of antibiotic synthesis in Burkholderia thailandensis." Journal of Bacteriology vol. 191. No. 12 pp. 3909-3918. (2009).
Duffy et al; "Regulatory measures against Erwinia amylovora in Switzerland", Bulletin OEPP/EPPO Bulletin 35, pp. 239-244. (2005).
Freudl "Signal peptides for recombinant protein secretion in bacterial expression systems" Microbial Cell Factories 17:52 (2018).
Jayaraman et al; "Bacterial quorum sensing: signals, circuits, and implications for biofilms and disease". Annual Review of Biomedical Engineering 10:pp. 145-167. (2008).
Khersonsky et al; "Chromogenic and fluorogenic assays for the lactonase activity of serum paraoxonase". Chembiochem. 7(1):pp. 49-53 . (2006).

(Continued)

*Primary Examiner* — Suzanne M Noakes
(74) *Attorney, Agent, or Firm* — Knobbe, Martens, Olson & Bear, LLP

(57) ABSTRACT

Mutated phosphotriesterase-like lactonases or functional fragments can be used in methods for treating or preventing infection of a bacterium in a host, such as a plant or a part, organ or a plant propagation material. The methods include applying the mutated phosphotriesterase-like lactonases or the wild-type enzyme to the host Cells expressing the mutated phosphotriesterase-like lactonases can also be produced using nucleic acid molecules and vectors encoding the mutated phosphotriesterase-like lactonases or functional fragments.

27 Claims, 7 Drawing Sheets

Specification includes a Sequence Listing.

(56)　　　　　References Cited

OTHER PUBLICATIONS

Lade et al "N-Acyl Homoserine Lactone-Mediated Quorum Sensing with Special Reference to Use of Quorum Quenching Bacteria in Membrane Biofouling Control". BioMed Research International. (2014).

Li et al; "Inhibition of quorum sensing-controlled virulence factors and biofilm formation in Pseudomonas fluorescens by cinnamaldehyde" International journal of food microbiology. 23;269:pp. 98-106. (2018).

Licciardello et al; "Pseudomonas corrugata contains a conserved N-acyl homoserine lactone quorum sensing system; its role in tomato pathogenicity and tobacco hypersensitivity response". FEMS Microbiology Ecology, vol. 61, Issue 2 pp. 222-234. (2007).

Loh et al; "Quorum sensing in plant-associated bacteria" Current opinion in plant biology.5(4):pp. 285-290. (2002).

McManus et al; "Antibiotic Use in Plant Agriculture". Annual review of phytopathology. 40(1):pp. 443-465. (2002).

Molina et al: "Autoinduction in Erwinia amylovora: Evidence of an acyl-homoserine lactone signal in the fire blight pathogen". Journal of Bacteriology 187(9):pp. 3206-3213. (2005).

Pieper et al; "ModBase, a database of annotated comparative protein structure models,and associated resources" Nucleic Acids Research vol. 39, pp. D465-D747. (2010).

Pöllumaa et al; "Quorum sensing and expression of virulence in pectobacteria" Sensors 12,pp. 3327-3349. (2012).

Schuster et al; "A network of networks: Quorum-sensing gene regulation in Pseudomonas aeruginosa" International journal of medical microbiology 296(2-3):pp. 73-81. (2006).

Venturi et al; "The plant pathogen Erwinia amylovora produces acyl-homoserine lactone signal molecules in vitro and in planta" FEMS Microbiology Letters 241 pp. 179-183. (2004).

Venturi et al;"Quorum sensing in the Burkholderia cepacia complex" Research in Microbiology 155 pp. 238-244. (2004).

Vrancken et al; "Pathogenicity and infection strategies of the fire blight pathogen Erwinia amylovora in Rosaceae: State of the art" Microbiology 159 pp. 823-832. (2013).

Wierenga "The TIM-barrel fold: A versatile framework for efficient enzymes" FEBS Letters 492 (2001) pp. 193-198. (2001).

Zhao et al; "Identification of Erwinia amylovora genes induced during infection of immature pear tissue" Journal of Bacteriology vol. 187No. 23 pp. 8808-8813. (2005).

Zhang et al; "The crystal structure of the phosphotriesterase from M. tuberculosis, another member of phosphotriesterase-like lactonase family". Biochemical and biophysical research communications. 510(2):pp. 224-229. (2019).

International Search Report and Written Opinion issued in International Application No. PCT/IL2020/050673, mailed Sep. 6, 2020.

* cited by examiner

Fig. 5A
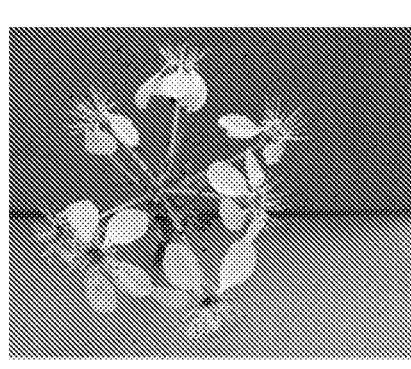
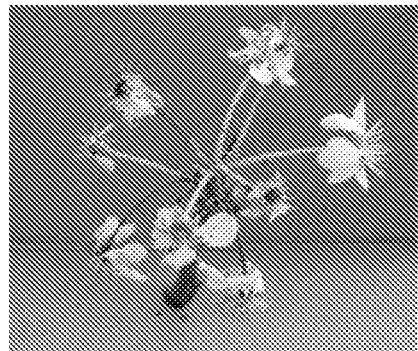
Fig. 5B
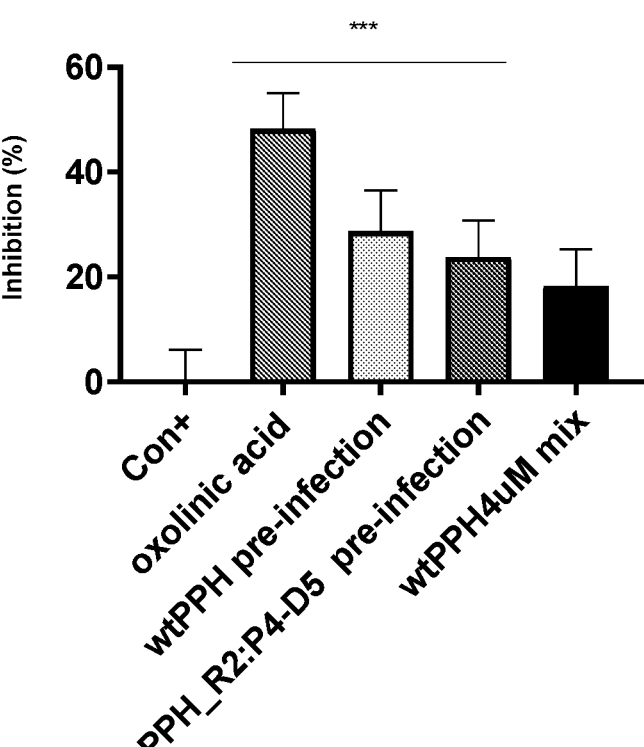
Fig. 5C
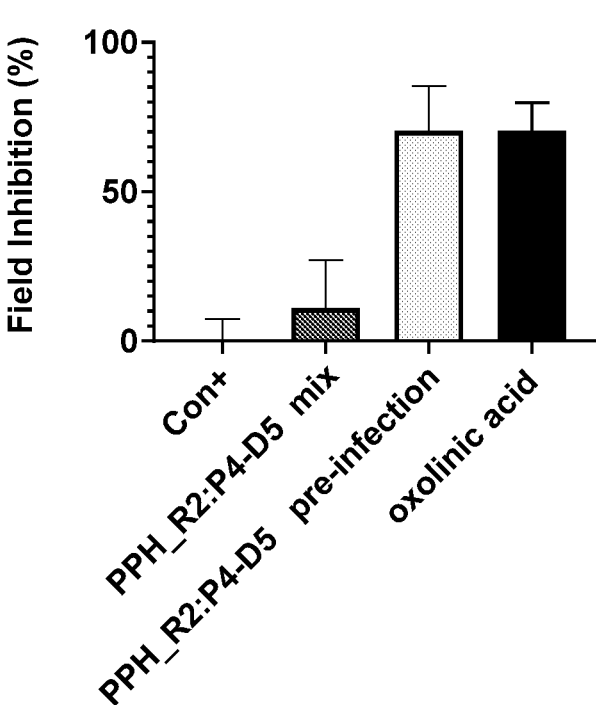

Fig. 6

```
- - - - - - - - - - - - - - - - - - - - - - - - - - - - - - - MISEFPELNTARGPIDTADLGV
- - - - - - - - - - - - - - - - - - - - - - - - - - - - - - - MISEFPELNTARGPIDTADLGV
- - - - - - - - - - - - - - - - - - - - - - - - - - - - - - - MISEFPELNTARGPIDTADLGV
VDEALKDAQTNSSSNNNNNNNNNLGIEGRISEFPELNTARGPIDTADLGV
- - - - - - - - - - - - - - - - - - - - - - - MPELNTARGPIDTADLGV

TLMRELVFIMTTEIAQNYPEAWGDEDKRVAGAIARLGELKARGVDTIVDLT
TLMRELVFIMTTEIAQNYPEAWGDEDKRVAGAIARLVELKARGVDTIVDLT
TLMRELVFIMTTEIAQNYPEAWGDEDKRVAGAIARLGELKARGVDTIVDLT
TLMRELVFIMTTEIAQNYPEAWGDEDKRVAGAIARLGELKARGVDTIVDLT
TLMRELVFIMTTEIAQNYPEAWGDEDKRVAGAIARLGELKARGVDTIVDLT

VIGLGRYIPRIARVAAATELNIVVATGLYTYNDVPFYFHYLGPGAQLDGPE
VIGLGRYIPRIARVAAATELNIVVATGLYTYNDVPFYFHYLGPGAQLDGPE
VIGLGRYIPRIARVAAATELNIVVATGLYTYNDVPFYFHYLGPGAQLDGPE
VIGLGRYIPRIARVAAATELNIVVATGLYTYNDVPFYFHYLGPGAQLDGPE
VIGLGRYIPRIARVAAATELNIVVATGLYTYNDVPFYFHYLGPGAQLDGPE

IMTDMFVRDIEHGIADTGIKAGILCATDEPGLTPGVERVLRAVAQAHKRT
IMTDMFVRDIEHGIADTGIKAGILCATDEPGLTPGVERVLRAVAQAHKRT
IMTDMFVRDIEHGIADTGIKAGILCATDEPGLTPGVERVLRAVAQAYKRT
IMTDMFVRDIEHGIADTGIKAGILCATDEPGLTPGVERVLRAVAQAHKRT
IMTDMFVRDIEHGIADTGIKAGILCATDEPGLTPGVERVLRAVAQAHKRT

GAPISTLTHAGLRRGLDQQRIFAEEGVDLSRVVIGLCGDSTDVGYLEELIA
GAPISTLTHAGLRRGLDQQRIFAEEGVDLSRVVIGLCGDSTDVGYLEELIA
GAPISTLTHAGLRRGLDQQRIFAEEGVDLSRVVIGLCGDSTDVGYLEELIA
GAPISTLTHAGLRRGLDQQRIFAEEGVDLSRVVIGLCGDSTDVGYLEELIA
GAPISTLTHAGLRRGLDQQRIFAEEGVDLSRVVIGLCGDSTDVGYLEELIA

AGSYLGMDRFGVDVISPFQDRVNIVARMCERGHADKMVLSHLACCYFDALP
AGSYLGMDRFGVDVISPFQDRVNIVARMCERGHADKMVLSHLACCYFDALP
AGSYLGMDRFGVDVISPFQDRVNIVARMCERGHADKMVLSHLACCYFDALP
AGSYLGMDRFGVDVISPFQDRVNIVARMCERGHADKMVLSHLACCYFDALP
AGSYLGMDRFGVDVISPFQDRVNIVARMCERGHADKMVLSHLACCYFDALP
```

Fig. 7A

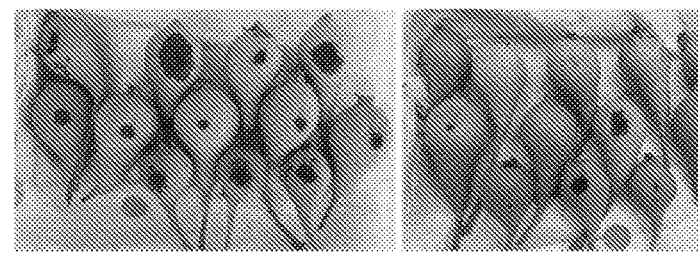

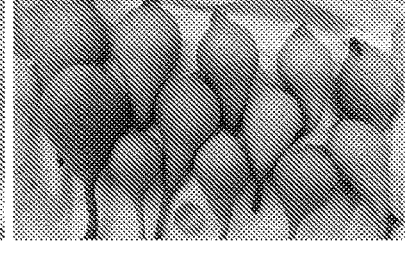

| Control | CuSO₄ | CuSO₄+PPH-R2:P4-D5 |

STABILIZED MUTANTS OF QUORUM QUENCHING LACTONASE AND USE THEREOF IN TREATMENT OF PATHOGENS

SEQUENCE LISTING IN ELECTRONIC FORMAT

The present application is being includes an Electronic Sequence Listing as an ASCII text file via EFS-Web. The Electronic Sequence Listing is provided as a file entitled SL_BEN046_001APC.txt created and last saved on May 18, 2022, which is approximately 323.7 KB in size, which is revised and saved on Dec. 16, 2025 as a file entitled SL2_BEN046_001APC.txt, which is approximately 323.9 KB in size. The information in the Electronic Sequence Listing is incorporated herein by reference in its entirety in accordance with 35 U.S.C. § 1.52(e).

FIELD OF THE INVENTION

The present invention relates in general to management of quorum sensing-dependent bacterial infections, and in particular to management of fire blight and other plant diseases.

BACKGROUND OF THE INVENTION

Disease caused by pathogens through quorum sensing regulation systems present an enormous challenge in clinical and agricultural settings. For example, effective management of fire blight, a contagious disease caused by *Erwinia amylovora* affecting apples, pears, and some other members of the family Rosaceae, is multi-faceted and largely preventative, utilizing a combination of sanitation, culturing practices, copper pesticide, products that contain *Streptomyces lydicus* as the active ingredient, and prophylactic application of antibiotics (e.g. streptomycin or oxytetracycline) (1).

Other examples of common plant pathogens that can cause diseases through quorum sensing regulation system in various crops are *Pectobacterium carotovorum* (2), *Pseudomonas syringae* (3) and *Pseudomonas corrugate* (4), affecting potatoes (*Solanum tuberosum* L.), kidney bean (*Phaseolus vulgaris*) and tomatoes (*Lycopersicon esculentum*). *Pseudomonas aeruginosa*, an opportunistic pathogen relying on a quorum sensing regulation system, is both a plant-pathogen and a leading cause of morbidity and mortality in cystic fibrosis patients and immunocompromised individuals.

However, regulatory restriction, public health concerns, and resistance development severely limit the long-term prospects of use of antibiotic and other agents (5).

There is thus an unmet need for effective agents and management of fire blight and other debilitating plant diseases.

SUMMARY OF INVENTION

In one aspect, the present invention provides a mutated phosphotriesterase-like lactonase comprising mutated phosphotriesterase-like lactonase, or a functional fragment thereof, in which an amino acid residue corresponding to position 59 or 172 of SEQ ID NO: 1 in an amino acid sequence having at least 30% identity with SEQ ID NO: 1 is substituted, wherein a glycine residue corresponding to G59 is substituted by an amino acid residue selected from valine, alanine, leucine, and isoleucine, or a histidine residue corresponding to H172 is substituted by an amino acid residue selected from tyrosine, phenylalanine and tryptophan, and said mutated phosphotriesterase-like lactonase has substantially identical TIM-barrel fold to the wild-type phosphotriesterase-like lactonase and preserved catalytic residues in its active site.

In another aspect, the present invention provides a composition comprising the mutated phosphotriesterase-like lactonase as defined above.

In an additional aspect, the present invention provides a method for treating or preventing infection of a bacterium in a plant or a part, organ or a plant propagation material thereof, said plant being infected by or susceptible to a bacterium secreting a lactone selected from N-(3-hydroxybutanoyl)-L-homoserine lactone (C4-HSL), N-(3-oxohexanoyl)-homoserine lactone (C6-oxo-HSL), N-[(3S)-tetrahydro-2-oxo-3-furanyl]octanamide (C8-oxo-HSL), and N-[(3S)-tetrahydro-furanyl]decanamide (C10-HSL), said method comprising applying on said plant or said part, organ or plant propagation material thereof, a phosphotriesterase-like lactonase having at least 30% identity to wild-type putative parathion hydrolase from *M. tuberclorosis* (PPH; SEQ ID NO: 1), substantially identical TIM-barrel fold to the wild-type putative parathion hydrolase and preserved catalytic residues in its active site, or a functional fragment thereof, or the mutated phosphotriesterase-like lactonase as defined above or any one of the above defined compositions.

In yet an additional aspect, the present invention provides an isolated nucleic acid molecule comprising a nucleic acid sequences encoding a mutated phosphotriesterase-like lactonase as defined above.

In still an additional aspect, the present invention provides an expression vector comprising the nucleic molecule of the present invention operatively linked to a promoter.

In still another aspect, the present invention provides a cell comprising the isolated nucleic acid molecule of or the expression vector as defined above.

In yet another aspect, the present invention is directed to a method of producing a mutated phosphotriesterase-like lactonase as defined above, or a functional fragment thereof, comprising: (i) cultivating a cell of any one of the above disclosed embodiments; and (ii) separating said mutated phosphotriesterase-like lactonase from said cell, thereby obtaining a mutated phosphotriesterase-like lactonase.

In a further aspect, the present invention provides a plant or a part, organ or a plant propagation material thereof, at least partly covered or coated with a composition as defined above.

BRIEF DESCRIPTION OF DRAWINGS

FIGS. 5A-C depict a pathogenicity assay of *E. amylovora* infection in healthy (A; upper picture) and infected (A; lower picture) pears flowers, in growth chamber, following infection with ($10^7$ CFU/ml) *E. amylovora*. Briefly, blooming branches with open flowers of *P. communis*, 'Spadona' were placed in a growth camber at 22° C. (12 h day, 12 h night). Enzyme solutions containing 4 μM of wtPPH and its evolved mutant, PPH_R2: P4-D5 (corresponding to G59V), were either sprayed on the flowers, and 2 hours later, cell suspension ($10^7$ CFU/ml) of *E. amylovora* were sprayed, or both enzyme and culture was mixed in a 1:1 ratio for 30 min and then sprayed. *E. amylovora* culture alone was used as a control (Positive control). As a standard we used 4 ppm oxolinic acid, the commonly used antibiotic. The experiment was done in three repeats, in each repeat 10 blossoms. The air condition and the light in the chamber where shut off over night after infection, in order to preserve humidity. Fire blight symptoms were evaluated after 3, 7 and 12 days from infection, showing results after 12 days, (LSD, P<0.05, n=30) 5B. In FIG. 5C, the evolved mutant PPH_R2: P4-D5 reduces Fire-blight symptoms in the field, presenting 70% inhibition. This inhibition degree is similar with the antibiotic used today, oxolinic acid (70%). Briefly, blossoms of *P. communis* 'Spadona' pear trees were sprayed with the evolved mutant PPH-G58V (4 μM), in different times of application; 30-45 minutes before, or simultaneously to infection (by mixing the enzymes solution with the culture for half an hour before spraying). In all cases $10^9$ CFU/ml *E.*

*amylovora* bacterial culture was used. After the infection, the blossoms were covered with plastic bag overnight to ensure high humidity. The experiment was done in 5 repeats, every repeat contained 10 blossoms, 5 blossoms on each side of the tree. No more than 4 treatments on a tree. Disease symptoms were evaluated following evaluation 13 days post inoculation by counting the diseased flowers in each blossom. The field trails were conducted at Hula Valley Orchards Experimental Farm in the north (33° 8'58.10"N35°37'16.93"E).

FIG. 6 shows alignment of partial sequences SEQ ID Numbers 1, 2, 3, 10 and 50. Conserved active site catalytic residues (white letters) and two residues substituted in PPH (G59V and H172Y) are shown.

Figure 7B:
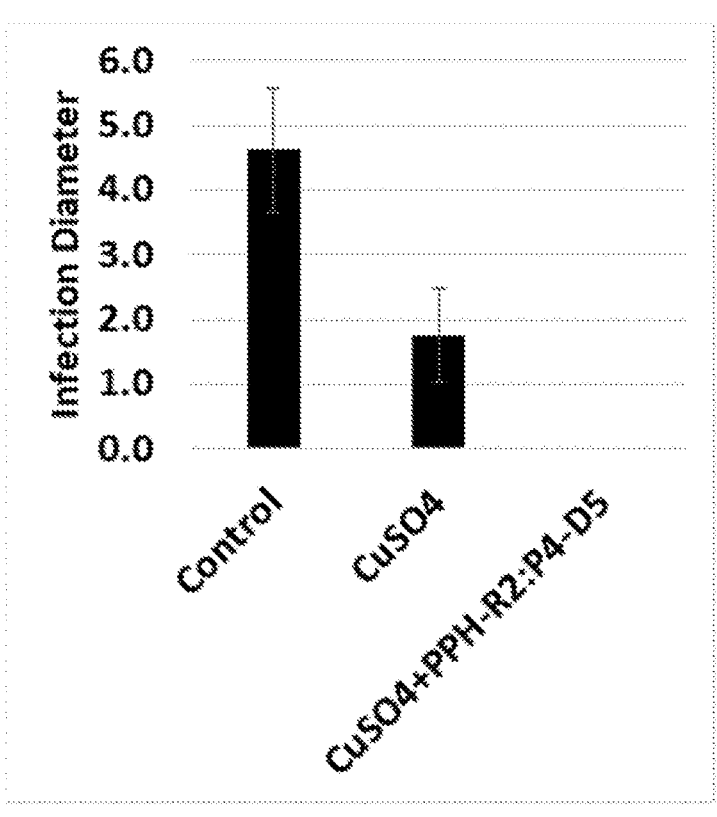

FIGS. 7A-B show results of a pathogenicity assay of *E. amylovora* infection in pear fruits. (A) Infected fruit was either untreated (left) or treated with 0.25 mM CuSO$_4$ alone (middle), or a combination of 0.25 mM CuSO$_4$ and 4 μM PPH-R2: P4-D5 (right). (B) A bar graph showing a summary of measurements of infection diameters in control and treated fruit.

DETAILED DESCRIPTION OF THE PREFERRED EMBODIMENT

Quorum sensing (QS) is a signaling system that occurs in various bacteria to sense its own population density and synchronize the expression of virulence genes via the secretion of small, diffusible signal molecules, such as N-acyl-homoserine lactone (AHL) (8). These molecules play a critical role in triggering virulence gene expression in QS-dependent pathogens, such as in the production of rotting enzyme (e.g. polygalacturonase) or biofilm components such as amylovoran (9). Interfering with the microbial QS system by quorum quenching (QQ) enzymes has been suggested as a potential strategy for disease control because QQ aims to shut down the virulence expression in pathogenic bacteria rather than restrict cell growth and has shown potential to overcome antibiotic resistance (10).

Phosphotriesterase-like lactonase from *M. tuberculosis* (also referred to herein as putative parathion hydrolase from *M. tuberclorosis*, PPH) is a quorum quenching enzyme (7), which belongs to the phosphotriesterase (PTE) like lactonases (7) possessing the TIM barrel fold and preserved catalytic site as defined below.

Figure 2A:
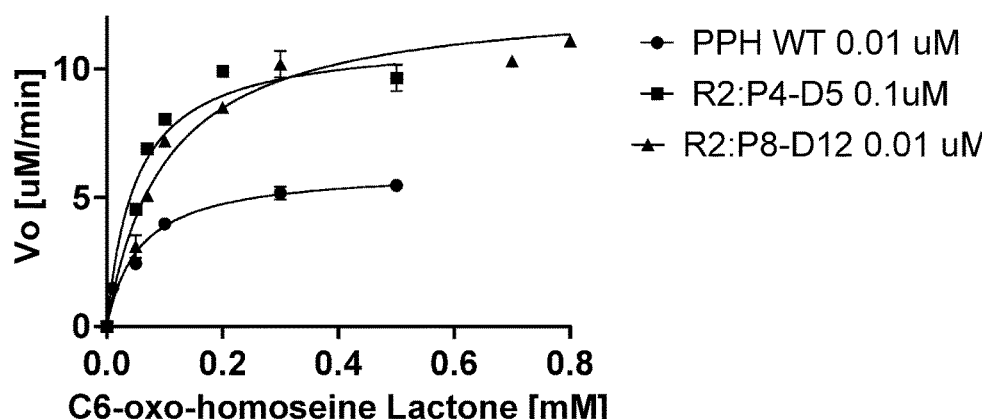
FIGS. 2A-D show that PPH evolved variants exhibit increased activity with C6-oxo HSL, increased thermal stability and improved shelf life. (a) The library of PPH was screened with TBBL as a substrate, following bacterial lysate incubation at 45° C. The variants with highest activity after heat incubation were taken for largescale production and purification. The variants harboring the following mutations: G58V in variant PPH_R2: P4-D5 and H171Y in variant PPH_R2: P8-D12, that present high catalytic activity $k_{cat}/K_M$ of $3.70*10^5$ s$^{-1}$M$^{-1}$, in the case of PPH_R2: P4-D5, which is 2 fold higher than the wildtype enzyme, and $k_{cat}/K_M$ of $9.67*10^4$ s$^{-1}$/M$^{-1}$ for PPH_R2: 8-D12. (b) Both variants have increased thermal stability exhibiting 15 degrees increase in their 50% residual activity, and maintaining 100% up to 60° C. (c) Following 4 days from purification, variant PPH_R2: P4-D5 maintained 100% of its activity, while wild-type (wt)PPH had 50% of its activity, moreover, following 37 days, while wtPPH lost 95% of its activity, PPH_R2: P4-D5 lost 80% of its activity. (d) The solved structure of PPH from *M. tuberculosis*, pdb number pdb 4if2, showing the location of the evolved variant's mutations G58V (*) and H171Y (**), which are far away from the active site.
Figure 2B:
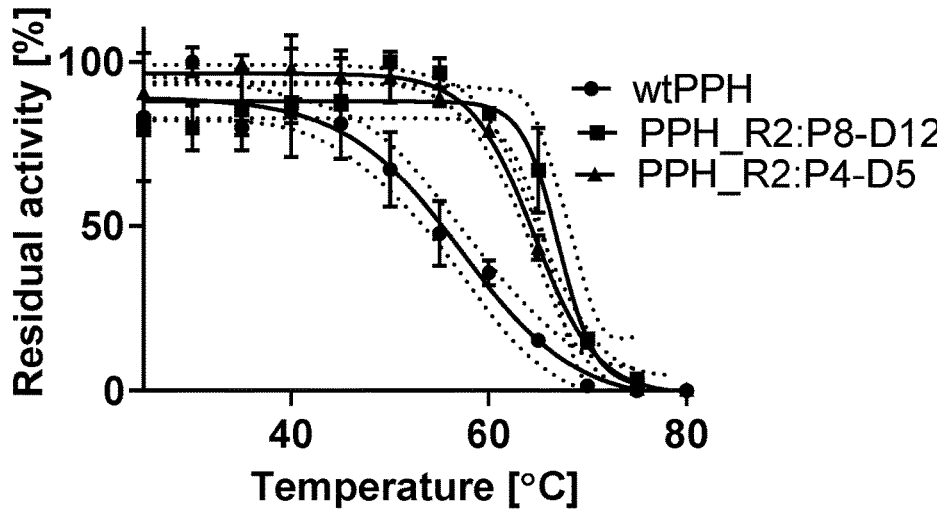

It has been found in accordance with the present invention that certain mutations in the sequence of PPH imbue the mutated enzyme with increased thermostability as compared with the corresponding wild-type enzyme. The particular variants used as an example were wild-type or mutant proteins lacking the first N-terminal methionine fused to maltose-binding protein (MBP), used as a tag for purifying the enzyme (SEQ ID NOs: 10-12), and it was found that a substitution of G58 to valine results in an enzyme with 50% residual activity at 62° C., and a substitution of H171 to tyrosine results in an enzyme with 50% residual activity at 65° C., while preserving or improving the catalytic activity as compared with wild type *M. tuberculosis* phosphotriesterase-like lactonase (FIGS. 2A-B). Moreover, the substitution of G58 to valine results in an enzyme with a $k_{cat}/K_M$ that is twofold higher than that of the wild-type enzyme. It should be noted that due to the very high intrinsic catalytic activity of the mutant enzymes (see Table 3), they remain highly active even with 50% residual activity at the relatively very high temperature of 62-65° C. (with a $k_{cat}/K_M$ of about $1-2*10^5$ s$^{-1}$M$^{-1}$).

The location of a certain amino acid residue in the proteins or fragments thereof disclosed herein is according to the numbering of the wild type M. tuberculosis phosphotriesterase-like lactonase as depicted in SEQ ID NO: 1 and is designated by referring to the one-letter code of the amino acid residue and its position in the wild type M. tuberculosis phosphotriesterase-like lactonase. Thus, for example, the glycine at the position corresponding to position 59 of the wild type M. tuberculosis phosphotriesterase-like lactonase, also referred to herein as G59, would be referred to as G59 also in a phosphotriesterase-like lactonase fragment or in a homologous phosphotriesterase-like lactonase of a different size according to alignment algorithms well known in the art of protein chemistry, such as (MUSCLE (Multiple Sequence Comparison by Log-Expectation) or MAFFT (Multiple Alignment using Fast Fourier Transform) (see e.g. FIG. 6).

For clarity, the positions of the amino acid residues in the sequences of the fusion-proteins used in Examples 2 to 4 herein, G58 and H171, correspond to G59 and H172, respectively, in the isolated wild-type full length protein. Similarly, the sequence of the functionally active deletion mutant used to solve the three-dimensional structure of the phosphotriesterase-like lactonase from M. tuberculosis lacks the four first N-terminal amino acid residues (11). Consequently, glycine at position 55 in the enzyme characterized in this paper corresponds to G59 according to the system used to identify amino acid residue positions in the enzymes of the present invention.

A substitution of an amino acid residue at a certain position with another amino acid residue is designated by referring to the one-letter code of the amino acid residue, its position as defined above and the one-letter code of the amino acid residue replacing the original amino acid residue. Thus, for example, a substitution of G59 with valine would be designated G59V.

In view of the above, in one aspect, the present invention provides a mutated phosphotriesterase-like lactonase comprising mutated wild-type phosphotriesterase-like lactonase, or a functional fragment thereof, in which an amino acid residue corresponding to position 59 or 172 of SEQ ID NO: 1 in an amino acid sequence having at least 30% identity with SEQ ID NO: 1 is substituted, wherein a glycine residue corresponding to G59 is substituted by an amino acid residue selected from valine, alanine, leucine, and isoleucine, or a histidine residue corresponding to H172 is substituted by an amino acid residue selected from tyrosine, phenylalanine and tryptophan, and said mutated phosphotriesterase-like lactonase has substantially identical TIM-barrel fold to the wild-type phosphotriesterase-like lactonase and preserved catalytic residues in its active site, i.e. the active site of said mutated phosphotriesterase-like lactonase are identical to the catalytic residues of the wild-type phosphotriesterase-like lactonase.

The proteins encoded by the nucleic acid molecules of the invention are not limited to those defined herein by specific amino acid sequences but may also be variants of these proteins or have amino acid sequences that are substantially identical to those disclosed above. A "substantially identical" amino acid sequence as used herein refers to a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid with another of the same class, e.g., substitution of one hydrophobic amino acid with another hydrophobic amino acid, a polar amino acid with another polar amino acid, a basic amino acid with another basic amino acid and an acidic amino acid with another acidic amino acid. One or more amino acids can be deleted from the peptide, thus obtaining a fragment thereof without significantly altering its biological activity, referred to herein as a "functional fragment".

The term "variant" as used herein refers to polynucleotides or polypeptides modified at one or more base pairs, codons, or amino acid residues, respectively, yet still retain the biological and enzymatic activity of a polypeptide of the naturally occurring sequence.

In certain embodiments, the biological activity or enzymatic function of all mutated phosphotriesterase-like lactonases including all variants and homologs are defined by substrate specificity and kinetic parameters, such as $k_{cat}$, $K_M$ and $k_{cat}/K_M$. Methods for measuring lactonase activity are well known in the art; for example, as taught in the Examples below, the hydrolysis of a lactone, such as C6-oxo-Homoserine lactone, can be monitored by following the appearance of the carboxylic acid products using a pH indicator as described previously (35).

Figure 2C:
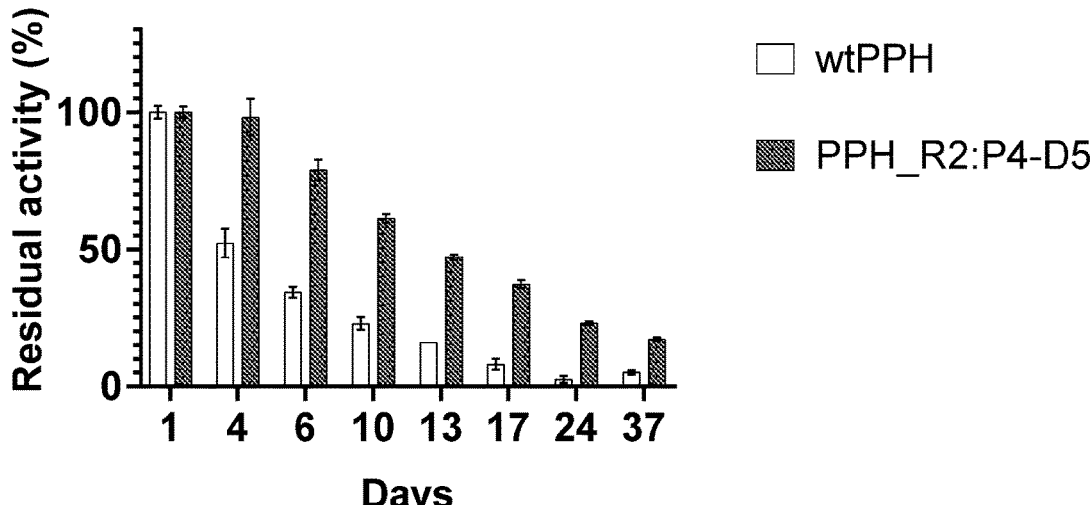
Figure 2D:
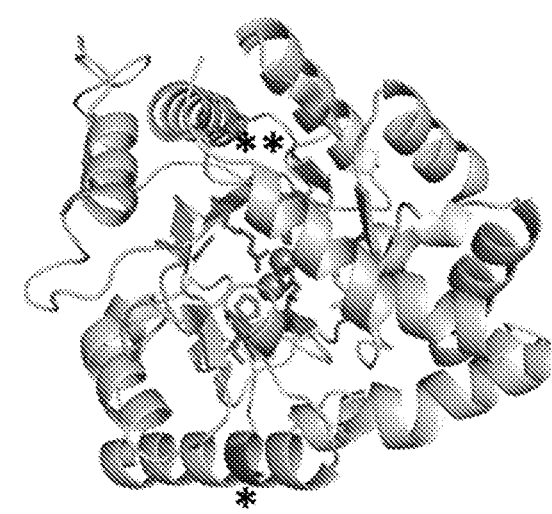

The catalytic residues are conserved throughout the PTE Like Lactonases (PLLs): His26, His28, His182 and His211, and Asp270. The sixth ligating residue is a carbamylated Lys149, (numbering are for PPH) (FIG. 2D and FIG. 6). A mutation in any one of these amino acid residues leads to loss of function.

Consequently, as defined above, any one of the mutated phosphotriesterase-like lactonases of the present invention has an intact active site, i.e. each one of the amino acid residues of these mutated phosphotriesterase-like lactonases corresponding to His26, His28, Lys149, His182, His211 and Asp270 in the wild-type full length PPH of SEQ ID NO: 1 is conserved.

In certain embodiments, each mutated phosphotriesterase-like lactonase, homologue and variant/mutant PPH described herein having at least 30% identity with SEQ ID NO: 1 and comprising a TIM-barrel fold that is substantially identical to that of the wild-type enzyme, are active enzymes capable of hydrolyzing lactones, such as C4-HSL (PubChem CID: 10330086 aka 3-Hydroxy-C4-HSL, N-(3-Hydroxybutanoyl)-L-homoserine lactone), C6-oxo-HSL (PubChem CID, 688505, aka N-(3-oxo-hexanoyl)-homoserine, N-Caproyl-L-homoserine lactone, N-[(3S)-Tetrahydro-2-oxo-3-furanyl]hexanamide, HHL), C8-oxo-HSL (PubChem CID: 6914579 aka N-[(3S)-Tetrahydro-2-oxo-3-furanyl]octanamide) and C10-HSL (PubChem CID: 10131281 aka N-[(3S)-Tetrahydro-2-oxo-3-furanyl]decanamide), and in particular C6-oxo-HSL.

The term "TIM-barrel fold" is used herein in its conventional meaning and refers to a conserved protein fold consisting of eight α-helices and eight parallel β-strands that alternate along the peptide backbone (12).

Methods for determining tertiary structure of a protein or generating a model thereof are well-known in the arts and can easily be done for a large number of proteins. For example, a model of the TIM-barrel fold may be generated using MODPIPE, an automated software, pipeline, that calculates models on the basis of known structural templates and sequence-structure alignments (13).

The variants and homologs of the mutated wild-type phosphotriesterase-like lactonase of the present invention are defined by their sequence identity with the wild-type phosphotriesterase-like lactonase of SEQ ID NO: 1, not including the mutation characterizing the mutant protein. Thus for example, a homolog having 90% identity with the mutant G59V has 90% identity with the sequence including amino acid residues 1-58 and 60-330 (or with the sequence including amino acid residues 1-330 and relating to position 59 as identical to wild-type G59).

In certain embodiments, the amino acid sequence having at least 30% identity with SEQ ID NO: 1 has 30%-99%, 30%-98%, 30%-97%, 30%-96%, 30%-95%, 30%-90%, 30%-85%, 30%-80%, 30%-75%, 30%-70%, 30%-65%, 30%-60%, 30%-55%, 30%-50%, 30%-45%, 30%-40%, 40%-99%, 40%-98%, 40%-97%, 40%-96%, 40%-95%, 40%-90%, 40%-85%, 40%-80%, 40%-75%, 40%-70%, 40%-65%, 40%-60%, 40%-55%, 40%-50%, 40%-45%, 50%-99%, 50%-98%, 50%-97%, 50%-96%, 50%-95%, 50%-90%, 50%-85%, 50%-80%, 50%-75%, 50%-70%, 50%-65%, 50%-60%, 50%-55%, 60%-99%, 60%-98%, 60%-97%, 60%-96%, 60%-95%, 60%-90%, 60%-85%, 60%-80%, 60%-75%, 60%-70%, 60%-65%, 70%-99%, 70%-98%, 70%-97%, 70%-96%, 70%-95%, 70%-90%, 70%-85%, 70%-80%, 70%-75%, 80%-99%, 80%-98%, 80%-97%, 80%-96%, 80%-95%, 80%-90%, 80%-85%, 90%-99%, 90%-98%, 90%-97%, 90%-96%, or 90%-95% identity with SEQ ID NO: 1.

In certain embodiments, the amino acid sequence having at least 30% identity with SEQ ID NO: 1 has at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, or at least 98% identity with SEQ ID NO: 1

In certain embodiments, the amino acid sequence having at least 30% identity with SEQ ID NO: 1 has 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% identity with SEQ ID NO: 1. In certain embodiments, the amino acid sequence has at least 79% identity and is selected from the group of sequences set forth in SEQ ID NOs: 16-110 (Table 2).

In certain embodiments, a glycine residue corresponding to G59 of SEQ ID NO: 1 is substituted by valine, alanine, leucine, or isoleucine; or a histidine residue corresponding to H172 of SEQ ID NO: 1 is substituted by tyrosine phenylalanine or tryptophan. In certain embodiments, any one of these substitutions is the sole substitution in the sequence of the mutated phosphotriesterase-like lactonase as compared with any one of SEQ ID NOS: 16-110, except for optional conservative substitutions of other amino acid residues or optional deletion of one or more amino acid residues at the N- or C-terminus. In certain embodiments, any one of these substitutions is the sole substitution in the sequence of the mutated phosphotriesterase-like lactonase as compared with SEQ ID NO: 1, i.e. no other modifications are made to the amino acid sequence, except for optional deletions of amino acid residues, for example at the N- or C-terminus that do not affect enzymatic function.

In certain embodiments, a glycine residue corresponding to G59 of SEQ ID NO: 1 is substituted by valine. In certain embodiments, this is the sole substitution in the sequence of the mutated phosphotriesterase-like lactonase as compared with any one of SEQ ID NOS: 16-110, except for optional conservative substitutions of other amino acid residues or optional deletion of one or more amino acid residues at the N- or C-terminus. In certain embodiments, this is the sole substitution in the sequence of the mutated phosphotriesterase-like lactonase as compared with SEQ ID NO: 1, except for conservative substitutions of other amino acid residues. In certain embodiments, this is the sole substitution in the sequence of the mutated phosphotriesterase-like lactonase as compared with SEQ ID NO: 1, i.e. no other modifications are made to the amino acid sequence, except for optional deletion of one or more amino acid residues at the N- or C-terminus. In certain embodiments, the mutated phosphotriesterase-like lactonase comprises or essentially consists of the amino acid sequence as set forth in SEQ ID NO: 2.

In certain embodiments, a histidine residue corresponding to H172 of SEQ ID NO: 1 is substituted by tyrosine. In certain embodiments, the is the sole substitution in the sequence of the mutated phosphotriesterase-like lactonase as compared with any one of SEQ ID NOS: 16-110, except for optional conservative substitutions of other amino acid residues or optional deletion of one or more amino acid residues at the N- or C-terminus. In certain embodiments, this is the sole substitution in the sequence of the mutated phosphotriesterase-like lactonase as compared with SEQ ID NO: 1, except for conservative substitutions of other amino acid residues. In certain embodiments, this is the sole substitution in the sequence of the mutated phosphotriesterase-like lactonase as compared with SEQ ID NO: 1, i.e. no other modifications are made to the amino acid sequence, except for optional deletion of one or more amino acid residues at the N- or C-terminus. In certain embodiments, the mutated phosphotriesterase-like lactonase comprises or essentially consists of the amino acid sequence as set forth in SEQ ID NO: 3.

For practical purposes, any one of the wild-type or mutated phosphotriesterase-like lactonases of the present invention may be provided as a fusion protein containing a tag useful for separating it from the cell extract by specific binding to a ligand-containing substrate or for improving solubility. For example, any one of the improved phosphotriesterase-like lactonases of the present invention may be provided as a fusion protein with a maltose binding protein at the amino terminus. Other examples of tags include chitin binding protein (CBP), Strep-tag (e.g. a selected nine-amino acid peptide (AWRHPQFGG, SEQ ID NO: 116) that displays intrinsic binding affinity towards streptavidin), glutathione-S-transferase (GST), and poly(His) tag. Tags including thioredoxin (TRX) and poly(NANP), used to improve solubility of the mutated phosphotriesterase-like lactonase may also be used. The tag is optionally removable by chemical agents or by enzymatic means, such as proteolysis or intein splicing.

Alternatively, the phosphotriesterase-like lactonase may be provided or encoded as a fusion protein containing a signal sequence facilitating its secretion into the growth medium. This is useful because it eliminates the need for disrupting the cells and provides for harvesting the protein of the invention simply by collecting the growth medium. The signal sequence is tailored for the host cell type used to express the protein. Freudl (14) teaches that, in bacteria, two major export pathways, the general secretion or Sec pathway and the twin-arginine translocation or Tat pathway, exist for the transport of proteins across the plasma membrane. The routing into one of these alternative protein export systems requires the fusion of a Sec- or Tat-specific signal peptide to the amino-terminal end of the desired target protein.

In short, the phosphotriesterase-like lactonase of the present invention may be provided as a fusion protein containing a Sec or Tat signal peptide. These peptides possess a similar tripartite overall structure consisting of a positively charged n-region, a central hydrophobic h-region, and a polar c-region that contains the recognition site (consensus: A-X-A) for signal peptidase. In Tat signal peptides, a characteristic amino acid consensus motif including two highly conserved arginine residues is present at the boundary between the often significantly longer n-region and the h-region. Furthermore, the h-region of Tat signal peptides is mostly less hydrophobic than those found in Sec signal peptides and in the c-region of Tat signal peptides, frequently positively charged amino acids (the so-called Sec-avoidance motif) are present that prevent a mistargeting of Tat substrates into the Sec pathway.

Since signal peptides, besides being required for the targeting to and membrane translocation by the respective protein translocases, also have additional influences on the biosynthesis, the folding kinetics, and the stability of respective target proteins, it is not possible so far to predict in advance which signal peptide will perform best in the context of a given target protein and a given bacterial expression host. However, methods for finding an optimal signal peptide for a desired protein are well known and are described e.g. in Freudl (incorporated by reference as if fully disclosed herein). The signal sequence may be removed during the process of secretion or it is optionally removable by chemical agents or by enzymatic means, such as proteolysis or intein splicing.

In certain embodiments, any one of the mutated phosphotriesterase-like lactonases of the present invention fused to a tag may lack 1 to 10 amino acid residues at its N- or C-terminus (as compared with the wild-type PPH), such as 1-4 amino acid residues at the N-terminus and said tag is fused to the N-terminus. Furthermore, a linker may be inserted between the sequence of the tag and the mutated phosphotriesterase-like lactonases, such as a poly-asparagine of e.g. about 10 residues.

In certain embodiments, the mutated phosphotriesterase-like lactonases fusion protein is of SEQ ID NO: 10, 11 or 12.

In certain embodiments, the mutated phosphotriesterase-like lactonase of any one of the above embodiments has an increased thermostability in comparison with thermostability of a non-mutated wild-type phosphotriesterase-like lactonase and/or substantially similar or higher lactonase catalytic activity provided with N-(3-oxo-hexanoyl)-homoserine lactone (C6-oxo-HSL) as a substrate in comparison with said non-mutated wild-type phosphotriesterase-like lactonase.

The term "thermostability" as used herein refers to the inherent property of a protein of maintaining its activities at or after being exposed to high temperatures, i.e. at temperatures that causes partial or total denaturation and loss of activity in most related proteins. The thermostability is often measured in relative term, $T_{50}$, as the temperature at which 50% of the enzymes maximal activity (at optimal conditions) is obtained after incubating the enzyme in a range of temperatures and then measuring catalytic activity at optimal temperature, referred to herein as "50% residual activity".

In certain embodiments, the increased thermostability is characterized by 50% residual activity (following incubation at a certain temperature) that is substantially or significantly higher than that of the wild type phosphotriesterase-like lactonase, i.e. at a temperature substantially or significantly higher than about 40° C.

In certain embodiments, the increased thermostability expressed as 50% residual activity ($T_{50}$) is at about 50° C.-80° C., 50° C.-75° C., 50° C.-70° C., 50° C.-65° C., 60° C.-80° C., 60° C.-75° C., 60° C.-70° C., 60° C.-65° C., 70° C.-80° C., 70° C.-75° C., or 75° C.-80° C.; or at 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C.

In certain embodiments, the increased thermostability comprises 50% residual activity at about 65° C., and in particular a substitution of G59 to valine results in an enzyme with 50% residual activity at about 62° C. or a substitution of H172 to tyrosine results in an enzyme with 50% residual activity at about 65° C.

In certain embodiments, the mutated phosphotriesterase-like lactonase G59V results in an enzyme with a $k_{cat}/K_M$ that is twofold higher than that of the wild-type enzyme.

The term "substantially similar lactonase catalytic activity" as used herein refers to a lactonase activity that is in the same order of magnitude as the reference, e.g. the same order of magnitude as the lactonase activity of the wild-type enzyme.

It has further been found in accordance with the present invention that the mutated phosphotriesterase-like lactonase has an extended shelf-life as compared with said non-mutated wild-type phosphotriesterase-like lactonase, as manifested e.g. by the lactonase catalytic activity of the mutated phosphotriesterase-like lactonase being substantially higher (by two fold) for a period of 37 days of storage at room temperature (about 25° C.) while the lactonase catalytic activity of the non-mutated wild-type phosphotriesterase-like lactonase is about 5% of its original activity after 37 days of storage at room temperature. Following 13 days from purification, variant PPH_R2: P4-D5 (corresponding to G59V) had about 50% residual activity, while the wild-type enzyme had 20% of its activity (FIG. 2C).

Thus, in certain embodiments, the mutated phosphotriesterase-like lactonase of any one of the above embodiments has an extended shelf-life as compared with said non-mutated wild-type phosphotriesterase-like lactonase.

In certain embodiments, the mutated phosphotriesterase-like lactonase of any one of the above embodiments has a shelf-life of up to 40 days, such as 4-40, 6-40, 8-40, 10-40, 12-40, 14-40, 16-40, 18-40, 20-40, 22-40, 24-40, 26-40, 28-40, 30-40, 32-40, 34-40, 36-40, 38-40, 4-38, 6-38, 8-38, 10-38, 12-38, 14-38, 16-38, 18-38, 20-38, 22-38, 24-38, 26-38, 28-38, 30-38, 32-38, 34-38, 36-38, 4-36, 6-36, 8-36, 10-36, 12-36, 14-36, 16-36, 18-36, 20-36, 22-36, 24-36, 26-36, 28-36, 30-36, 32-36, 34-36, 4-34, 6-34, 8-34, 10-34, 12-34, 14-34, 16-34, 18-34, 20-34, 22-34, 24-34, 26-34, 28-34, 30-34, 32-34, 4-32, 6-32, 8-32, 10-32, 12-32, 14-32, 16-32, 18-32, 20-32, 22-32, 24-32, 26-32, 28-32, 30-32, 4-30, 6-30, 8-30, 10-30, 12-30, 14-30, 16-30, 18-30, 20-30, 22-30, 24-30, 26-30, 28-30, 4-28, 6-28, 8-28, 10-28, 12-28, 14-28, 16-28, 18-28, 20-28, 22-28, 24-28, 26-28, 4-26, 6-26, 8-26, 10-26, 12-26, 14-26, 16-26, 18-26, 20-26, 22-26, 24-26, 4-24, 6-24, 8-24, 10-24, 12-24, 14-24, 16-24, 18-24, 20-24, 22-24, 4-22, 6-22, 8-22, 10-22, 12-22, 14-22, 16-22, 18-22, 20-22, 4-20, 6-20, 8-20, 10-20, 12-20, 14-20, 16-20, 18-20, 4-18, 6-18, 8-18, 10-18, 12-18, 14-18, 16-18, 4-16, 6-16, 8-16, 10-16, 12-16, 14-16, 4-14, 6-14, 8-14, 10-14, 12-14, 4-12, 6-12, 8-12, 10-12, 4-10, 6-10, 8-10, 4-8, 6-8, or 4-6 days. In certain embodiments, the mutated phosphotriesterase-like lactonase of any one of the above embodiments has a shelf-life of about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days.

In certain embodiments, in a mutated phosphotriesterase-like lactonase of the present invention, a glycine residue corresponding to G59 of SEQ ID NO: 1 is substituted by valine or a histidine residue corresponding to H172 of SEQ ID NO: 1 is substituted by tyrosine; and said mutated phosphotriesterase-like lactonase has an increased thermostability in comparison with the thermostability of a non-mutated wild-type phosphotriesterase-like lactonase as defined above or substantially similar or higher lactonase catalytic activity provided with N-(3-oxo-hexanoyl)-homoserine lactone as a substrate in comparison with said non-mutated phosphotriesterase-like lactonase as defined above.

In certain embodiments, the mutated phosphotriesterase-like lactonase comprises or essentially consists of the amino acid sequence as set forth in SEQ ID NO: 2, SEQ ID NO: 3; SEQ ID NO: 11 or SEQ ID NO: 12, said increased thermostability expressed as $T_{50}$ is about 55° C. to about 80° C., such as about 65° C. (or as defined above) or said mutated phosphotriesterase-like lactonase has an extended shelf-life as compared with said non-mutated phosphotriesterase-like lactonase as defined above.

In another aspect, the present invention is directed to a composition comprising the mutated phosphotriesterase-like lactonase of any one of the above disclosed embodiments.

In certain embodiments, any one of the compositions described above further comprises an agriculturally acceptable surfactant, such as soap, higher alcohol sulfate, alkyl sulfonate, alkylaryl sulfonate, quaternary ammonium salts, polyalkylene oxide; a coating agent, such as xanthan gum and talc, sodium lignosulfate, carboxymethylcellulose sodium and dextrin; a gel-forming agent, such as sodium alginate; a wetting agent, such as Genapol® X060—a fatty alcohol polyglycol ether and AF® 365 Antifoam—a polydimethylsiloxane antifoam emulsion; a non-ionic surfactant antifoam agent, such as AF® 365 Antifoam—a polydimethylsiloxane antifoam emulsion; and/or a stabilizer, such as glycerol. The composition may further comprise solid carriers, liquid carriers, emulsifying and dispersing agents etc., which are all well known in the art. Examples of these carriers include acacia, acidic terra abla, bentonite, calcium carbonate, carbon dioxide, clay, diatomaceous earth, freon, kaolin, nitrocellulose, and starch.

In certain embodiments, any one of the compositions described above is formulated in the form of a solid material (e.g. powder) or a solution.

In certain embodiments, any one of the compositions described above further comprises an additional antimicrobial agent, such as a metal, e.g. silver or copper or an alloy thereof (brass, bronze, cupronickel, copper-nickel-zinc), a metal ion salt, such as copper sulfate ($CuSO_4$); an antibiotic used in plant agriculture, such as streptomycin sulfate, oxytetracycline, oxolinic acid and gentamicin; or a fungicide, such as Mancozeb, Tricyclazole, Carbendazim, Hexaconazole, Metalaxyl, Benomyl, Difenoconazole, Propiconazole, Kitazin, Tebuconazole, Copper oxychloride, Tridemorph, and Propineb.

In certain embodiments, any one of the compositions described above is a pharmaceutical composition further comprising one or more physiologically acceptable carriers or excipients. The carrier(s) must be "acceptable" in the sense of being compatible with the other ingredients of the composition and not deleterious to the recipient thereof.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

In an additional aspect, the present invention provides a method for treating or preventing a bacterial infection in a host infected by or susceptible to a bacterium causing disease through quorum sensing regulation systems, wherein said bacteria secret a lactone selected from N-(3-Hydroxybutanoyl)-L-homoserine lactone (C4-HSL), N-(3-oxo-hexanoyl)-homoserine lactone (C6-oxo-HSL), N-[(3S)-Tetrahydro-2-oxo-3-furanyl]octanamide (C8-oxo-HSL) and N-[(3S)-Tetrahydro-furanyl]decanamide (C10-HSL), and said method comprising applying or administering to said host phosphotriesterase-like lactonase having at least 30% identity to wild-type putative parathion hydrolase from M. tuberclorosis (PPH; SEQ ID NO: 1), substantially identical TIM-barrel fold to the wild-type putative parathion hydrolase and preserved catalytic residues in its active site, or a functional fragment thereof, or the mutated phosphotriesterase-like lactonase of any one of the above disclosed embodiments or any one of the above defined compositions. The substrate-specificity of putative parathion hydrolase from M. tuberclorosis is known from Afriat et al., 2006 (7).

Examples of bacteria secreting one or more of the above-mentioned lactones are:

Pseudomonas aeruginosa, a Gram-Negative opportunistic pathogen relying on a quorum sensing regulation system, is both a plant pathogen and a leading cause of morbidity and mortality in cystic fibrosis patients and immunocompromised individuals, secrets C4-HSL and C12-oxo-HSL) (22).

Pseudomonas fluorescens can be found in soil and in water and is an important food spoiling bacteria secreting C8-HSL (23). It is an unusual cause of disease in humans, and usually affects patients with compromised immune systems.

Erwinia amylovora causes fire blight on Rosaceae crops and produces and secretes N-acyl homoserine lactone a N-(3-oxo-hexanoyl)-homoserine lactone and N-(3-hydroxy-hexanoyl)-homoserine lactone (15).

Pectobacterium. carotovorum causes bacterial stem rot and fruit rot in tomatoes and soft rot in potatoes and uses QS signaling to control the expression of pathogenicity factors, such as extracellular enzymes and the Hrp (type III secretion) system, and carbapenem antibiotic production (16) (17) (18) (19), which are mainly controlled by 3-oxo-C6 and 3-oxo-C8 AHL (Barnard a et al, 2007).

Pseudomonas corrugata secrets C6-HSL quorum sensing signals (3-oxo-C6 and 3-oxo-C8 AHL) to regulate traits that contribute to virulence, antimicrobial activity and fitness (4).

P. syringae causes bacterial speck disease and is reported to use multiple QS circuits, specific to 3-oxo-C6, 3-oxo-C8 and C8-AHL (21).

Burkholderia vietnamiensis produces multiple AHL molecules, with the predominant AHL being N-decanoylhomoserine lactone (C10-HSL) and with C8-HSL and N-hexanoylhomoserine lactone ($C_6$-HSL) (24); Burkholderia cepacia secrets N-octanoylhomoserine lactone (C8-HSL) (25); and Burkholderia thailandensis secrets N-oxo-decanoylhomoserine lactone (C10-oxo-HSL) and N-oxo-octanoylhomoserine lactone (C8-oxo-HSL) (26).

In certain embodiments, the host is a plant and thus the present invention provides a method for treating or preventing infection of a bacterium in a plant or a part, organ or a plant propagation material thereof, said plant being infected by or susceptible to a bacterium secreting a lactone selected from N-(3-hydroxybutanoyl)-L-homoserine lactone (C4-HSL), N-(3-oxo-hexanoyl)-homoserine lactone (C6-oxo-HSL), N-[(3S)-tetrahydro-2-oxo-3-furanyl]octanamide (C8-oxo-HSL), and N-[(3S)-tetrahydro-furanyl]decanamide (C10-HSL), said method comprising applying on said plant or said part, organ or plant propagation material thereof, a phosphotriesterase-like lactonase having at least 30% identity to wild-type putative parathion hydrolase from *M. tuberclorosis* (PPH; SEQ ID NO: 1), substantially identical TIM-barrel fold to the wild-type putative parathion hydrolase and preserved catalytic residues in its active site, or a functional fragment thereof, or the mutated phosphotriesterase-like lactonase of any one of the above disclosed embodiments or any one of the above defined compositions.

Thus, in certain embodiments, the bacterium is selected from the group consisting of *Erwinia amylovora, Pectobacterium carotovorum, Pseudomonas syringae, Pseudomonas corrugata, Burkholderia vietnamiensis, Burkholderia cepacia, Burkholderia thailandensis* and *Pseudomonas aeruginosa*, including any pathovars. In certain embodiments, the bacterium is a bacterium secreting C6-oxo-HSL selected from *Erwinia amylovora, Pectobacterium carotovorum* and *Pseudomonas syringae*.

In certain embodiments, the bacterium is *Erwinia amylovora* and the plant disease caused by it is fire blight on Rosaceae crops, e.g. pome fruit trees such as apple and pear.

In certain embodiments, the bacterium is *Pectobacterium carotovorum* and the plant disease caused by it, is bacterial soft rot on a plant such as carrot, potato, tomato, leafy greens, squash and other cucurbits, onion, green peppers, and African violets, and in particular beet vascular necrosis and blackleg of potato as well as slime flux on many different tree species.

In certain embodiments, the bacterium is *Pseudomonas syringae* and the plant disease caused by it is bacterial speck disease. In particular, the *Pseudomonas syringae* bacterium may be *Pseudomonas tomato* (formerly known as *Pseudomonas syringae* pv. *tomato*) and the disease tomato bacterial speck disease.

In certain embodiments the host is a mammal, such as cystic fibrosis patients and immunocompromised individuals, and the bacterium is *Pseudomonas aeruginosa* or *Pseudomonas fluorescens*.

In certain embodiments, the putative parathion hydrolase from *M. tuberclorosis* or a composition thereof as defined in any one of the above embodiments, and a separate composition comprising a copper salt, such as $CuSO_4$, are separately applied to said plant, part, organ or plant propagation material of said plant. The two compositions may be applied concomitantly or sequentially.

In certain embodiments, the method of treating or preventing infection of a bacterium of any one of the above disclosed embodiments comprises applying the mutated phosphotriesterase-like lactonase of any one of the above embodiments.

In certain embodiments, the method of treating or preventing infection of a bacterium of any one of the above disclosed embodiments comprises applying the mutated phosphotriesterase-like lactonase, wherein G59 of SEQ ID NO: 1 is substituted by valine, such as the mutated phosphotriesterase-like lactonase comprising or essentially consisting of the amino acid sequence as set forth in SEQ ID NO: 2 or SEQ ID NO: 11 or as defined in any one of the above embodiments; or the phosphotriesterase-like lactonase, wherein H172 of SEQ ID NO: 1 is substituted by tyrosine, such as the mutated phosphotriesterase-like lactonase comprising or essentially consisting of the amino acid sequence as set forth in SEQ ID NO: 3 or SEQ ID NO: 12 or as defined in any one of the above embodiments.

In yet an additional aspect, the present invention provides an isolated nucleic acid molecule comprising a nucleic acid sequence encoding a mutated phosphotriesterase-like lactonase of any one of the above disclosed embodiments.

In certain embodiments, the isolated nucleic acid molecule encodes for a fusion protein containing a tag useful for separating it from the cell extract by specific binding to a ligand-containing substrate. For example, the nucleic acid sequence encoding any one of the wild-type or improved mutant phosphotriesterase-like lactonases of the present invention may be fused to sequences encoding a maltose binding protein, (e.g. as set forth in any one of SEQ ID NOs: 13-15 or it may encode any of the sequences of SEQ ID Nos: 16-110 in Table 2 similarly fused to such a tag). Alternatively, the nucleic acid sequence encodes any one of the phosphotriesterase-like lactonases of the present invention containing a signal sequence facilitating its secretion into the growth medium as described above.

In certain embodiments, the nucleic acid sequence is the original unmodified DNA sequence encoding the wild-type or mutant enzymes as set forth in SEQ ID NOs: 4 (wild-type), SEQ ID NO: 5 (G59V), SEQ ID NO: 6 (H172Y), or SEQ ID NO: 10 (wild-type fusion with MBP).

In certain embodiments, the nucleic acid sequence is optimized for expression in *E. coli* to increase its expression level. For example, the nucleic acid sequence may be optimized by changing its codons to match the most prevalent tRNAs in *E. coli* (see e.g. Puigbò et al., Nucleic Acids Research, 2007, Vol. 35). In certain embodiments, the optimized sequence of the wild-type enzyme is as set forth in SEQ ID NO: 7.

In certain embodiments, the (codon-optimized) nucleic acid sequence is as set forth in SEQ ID NO: 8 [G59V] or SEQ ID NO: 9 [H172Y] or MBP-fusion proteins thereof as set forth in SEQ ID NOs: 14 and 15.

In still an additional aspect, the present invention provides an expression vector comprising the nucleic molecule of any one of the above disclosed embodiments operatively linked to a promoter.

A coding nucleic acid sequence is "operably linked" to a regulatory sequence (e.g., promoter) if the regulatory sequence is capable of exerting a regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls initiation of gene expression.

According to some embodiments of the invention, the promoter is heterologous to the isolated polynucleotide and/or to the host cell.

Any suitable promoter sequence can be used by the nucleic acid construct of the present invention. It can be constitutive or inducible.

In still another aspect, the present invention provides a cell comprising and/or expressing the isolated nucleic acid molecule of any one of the above disclosed embodiments or the expression vector defined above.

In certain embodiments, the cell is selected from a bacterial, fungal, mammal or plant cell, preferably a bacterial cell and in particular *E. coli*.

In yet another aspect, the present invention is directed to a method of producing a mutated phosphotriesterase-like lactonase, or a functional fragment thereof, comprising: (i) cultivating a cell of any one of the above disclosed embodiments; and (ii) separating said mutated phosphotriesterase-like lactonase from said cell, thereby obtaining a mutated phosphotriesterase-like lactonase.

In certain embodiments, the cell is selected from a bacterial, fungal, mammal or plant cell preferably a bacterial cell and in particular *E. coli.*

Methods for growing bacterial cells and for harvesting secreted proteins from the cells are well-known in the arts (Choi, J. H., and Lee, S. Y., 2004). As a non-limiting example, *E. coli* cells may be grown in a suitable growth medium, such as Lysogeny Broth (LB) medium comprising glucose. The bacteria is then harvested and lysed in a suitable lysis buffer and disrupted, for example by sonication. Alternatively, the protein is tagged with a signal sequence facilitating secretion of the protein into the growth medium, which saves the step of lysing the cells. The secreted or released protein is then isolated and purified from a clarified growth medium or lysate. In case the protein of interest is tagged for the purpose of facilitating isolation, it is purified on a column that specifically binds the tag, washed and eluted. For example, clarified lysate containing a recombinant protein comprising the protein of interest and a maltose-binding protein is loaded onto an amylose column. The recombinant protein is then eluted with maltose-supplemented column buffer. Protein-containing elution fractions are collected, concentrated and optionally fractionized using a size exclusion column. A non-limiting specific example of a method for producing the mutated enzyme is found in the Examples below.

In certain embodiments, the phosphotriesterase-like lactonase further comprises a tag, such as maltose binding protein (MBP) (e.g. as set forth in any one of SEQ ID NOs: 10-12 or any of the sequences of SEQ ID Nos: 16-110 in Table 2 similarly fused to such a tag. Alternatively, the phosphotriesterase-like lactonase of the present invention may be provided or encoded as a fusion protein containing a signal sequence facilitating its secretion into the growth medium as described above.

Furthermore, lactonase and phosphotriesterase catalytic activities can be tested on their respective substrate e.g. according to methods disclosed in experimental part of the invention.

In a further aspect, the present invention provides a plant or a part, organ or a plant propagation material thereof, at least partly covered or coated with a composition of any one of the embodiments described above.

In certain embodiments, the plant is selected from Rosaceae crops, such as apple and pear trees; carrot; potato; tomato; leafy greens; squash and other cucurbits; onion; green peppers; *Gesneriacea*, such as African violets; beet; and potato.

The term "treating" as used herein refers to means of obtaining a desired physiological effect. The effect may be therapeutic in terms of partially or completely curing a disease and/or symptoms attributed to the disease. The term refers to inhibiting the disease, i.e. arresting its development; ameliorating the disease, i.e. causing regression of the disease; or protecting a plant or a part, organ or a plant propagation material thereof from the disease by preventing or limiting infection. The term as used herein further refers to reduction of bacterial virulence as exhibited e.g. in reduced extracellular polysaccharide (EPS) matrix or levan that contribute to the formation of the EPS (see FIG. 3).

The term "preventing" may be used herein interchangeably with the term "protecting" or "prophylactic treatment" and refers to application of the composition of the present invention to a susceptible mammal, plant or a part, organ or a plant propagation material thereof, before discernible microbial infection.

A method of preventing infection on e.g. a seed, fruit, blossom or flower by applying the composition may result in subsequent reduced infection as compared with a seed, fruit, blossom or flower that was not subject to this method of prevention, and the term should not be understood as necessarily resulting in the total absence of microbial infection or microbial presence, since the treatment neither kills the bacteria nor inhibits cell growth. The effect of the method of prevention of the present invention may be observed for example in the case of seeds that have been subject to the method of preventing microbial infection prior to discernible infection, which subsequent to planting yield plants having higher stem length and foliage mass as compared to plants derived from seeds that have not been subject to this method. The difference in plant biomass yield is a result of the absence of infection, or reduced level of infection in the pretreated seeds that developed subsequent and in spite of the prophylactic treatment, as compared with the non-treated seeds. Flowers, whole blossoms and fruit may similarly be pretreated by application of the composition of the present invention, which results in preservation of flower, blossom and fruit integrity (see FIGS. 4A-C) and thus increased yield. Another example would be using the method of the present invention for preventing infection of a microorganism in a plant or seedling growing in the vicinity of infected plants (from the same field or from other fields). In case the infective agent spreads from the infected plants or field to the initially non-infected plants or field, prophylactic treatment will protect the plants and thus result in higher yield as compared with plants or seedlings that have not been subject to this method.

The method of the present invention may comprise direct application of the composition defined herein to the plant or part, organ or plant propagation material thereof, or the composition may be applied thereto in a formulation such as granules, dusts, emulsifiable concentrates, wettable powders, pastes, water-based flowables, dry flowables, oil agents, aerosols, fogs or fumigants with suitable solid carriers, liquid carriers, emulsifying and dispersing agents, etc., as described above.

In certain embodiments, any one of the compositions or formulations described above is applied to the plant or a part, organ or a plant propagation material thereof by spraying, immersing, dressing, coating, pelleting or soaking.

In certain embodiments, the method of the present invention is for treating or preventing infection of a bacterium defined above on a propagation material such as a seed, root, fruit, tuber, bulb, rhizome, or part of a plant, wherein the composition is applied to the propagation material by spraying, immersing, dressing, coating, pelleting or soaking prior to or after detection of the infection.

In certain embodiments, the plant propagation material is a seed or a fruit.

In certain embodiments, the part of a plant is a leaf, branch, flower, blossom, inflorescence or a stem.

The term "phosphotriesterase-like lactonase from *M. tuberculosis*" is used interchangeably herein with the term "putative parathion hydrolase (PPH) from *M. tuberculosis*" and quorum quenching (QQ) PPH.

The transition phrase "consisting essentially of" or "essentially consisting of", when referring to an amino acid or nucleic acid sequence, refers to the a sequence that includes the listed sequence and is open to present or absent unlisted sequences that do not materially affect the basic and novel properties of the protein itself or the protein encoded by the nucleic acid sequence.

The term "substantially higher than" when referring to a temperature at which 50% residual activity is measured, refers to a difference of at least 5° C. higher than the reference.

The term "significantly higher than" refers to a statistically significant difference as tested with e.g. Student's t-test with $\alpha$=0.05.

The term "about" as used herein means that values which are 10% above or below the value provided are also included. Numbers that are not preceded by the term "about" are nevertheless to be understood as being modified in all instances by this term. Accordingly, unless indicated to the contrary, the numerical parameters set forth in this description and attached claims are approximations that may vary by up to plus or minus 10% depending upon the desired properties sought to be obtained by the present invention.

TABLE 1

Protein and DNA sequences of wild-type and mutant PPH

| Sequence ID number | Sequence type | Comment |
|---|---|---|
| SEQ ID NO: 1 | protein | wild type PPH (CKQ82621.1) |
| SEQ ID NO: 2 | protein | G59V PPH |
| SEQ ID NO: 3 | protein | H172Y PPH |
| SEQ ID NO: 4 | DNA | Unmodified* wild type PPH |
| SEQ ID NO: 5 | DNA | Unmodified* G59V PPH |
| SEQ ID NO: 6 | DNA | Unmodified* H172Y |
| SEQ ID NO: 7 | DNA | codon optimized wild type PPH |
| SEQ ID NO: 8 | DNA | codon optimized G59V PPH |
| SEQ ID NO: 9 | DNA | codon optimized H172Y PPH |
| SEQ ID NO: 10 | protein | wild type PPH-MBP fusion** |
| SEQ ID NO: 11 | protein | G59V PPH-MBP fusion** |
| SEQ ID NO: 12 | protein | H172Y PPH-MBP fusion** |
| SEQ ID NO: 13 | DNA | wild type PPH-MBP fusion** |
| SEQ ID NO: 14 | DNA | G59V PPH-MBP fusion** |
| SEQ ID NO: 15 | DNA | H172Y PPH-MBP fusion** |

*unmodified means native DNA sequence or not codon optimized.
**PPH is lacking the N-terminal Methionine

TABLE 2

Protein sequences of PPH homologs (PTE Like Lactonases (PLLs).

| Sequence ID number | Accession no/Protein name. | Protein source |
|---|---|---|
| SEQ ID NO: 16 | CKS73406.1 parathion hydrolase | *Mycobacterium tuberculosis* |
| SEQ ID NO: 17 | SGN98718.1 parathion hydrolase | *Mycobacterium tuberculosis* |
| SEQ ID NO: 18 | AAK44461.1 parathion hydrolase | *Mycobacterium tuberculosis* CDC1551 |
| SEQ ID NO: 19 | WP_003900835.1 phosphotriesterase-related protein | *Mycobacterium tuberculosis* |
| SEQ ID NO: 20 | WP_031702804.1 phosphotriesterase-related protein | *Mycobacterium tuberculosis* |
| SEQ ID NO: 21 | WP_070891680.1 phosphotriesterase-related protein | *Mycobacterium tuberculosis* |
| SEQ ID NO: 22 | WP_069334075.1 phosphotriesterase | *Mycobacterium tuberculosis* |
| SEQ ID NO: 23 | WP_003401263.1 MULTISPECIES: phosphotriesterase | *Mycobacterium* |
| SEQ ID NO: 24 | WP_055366308.1 phosphotriesterase | *Mycobacterium tuberculosis* |
| SEQ ID NO: 25 | WP_057136094.1 phosphotriesterase | *Mycobacterium tuberculosis* |
| SEQ ID NO: 26 | WP_031672770.1 phosphotriesterase family protein | *Mycobacterium tuberculosis* |
| SEQ ID NO: 27 | WP_031726559.1 phosphotriesterase-related protein | *Mycobacterium tuberculosis* |
| SEQ ID NO: 28 | WP_031700829.1 phosphotriesterase family protein | *Mycobacterium tuberculosis* |
| SEQ ID NO: 29 | WP_031665946.1 phosphotriesterase | *Mycobacterium tuberculosis* |
| SEQ ID NO: 30 | WP_031687538.1 phosphotriesterase family protein | *Mycobacterium tuberculosis* |
| SEQ ID NO: 31 | WP_128884084.1 phosphotriesterase-related protein | *Mycobacterium tuberculosis* |
| SEQ ID NO: 32 | WP_057118862.1 phosphotriesterase | *Mycobacterium tuberculosis* |
| SEQ ID NO: 33 | WP_031751683.1 phosphotriesterase family protein | *Mycobacterium tuberculosis* |

TABLE 2-continued

Protein sequences of PPH homologs (PTE Like Lactonases (PLLs).

| Sequence ID number | Accession no/Protein name. | Protein source |
|---|---|---|
| SEQ ID NO: 34 | WP_015629423.1 phosphotriesterase-related protein | *Mycobacterium tuberculosis* |
| SEQ ID NO: 35 | WP_015302462.1 phosphotriesterase Php (parathion hydrolase) (PTE) (aryldialkylphosphatase) (paraoxonase) (a-esterase) (aryltriphosphatase) (paraoxon hydrolase) | *Mycobacterium canettii* |
| SEQ ID NO: 36 | WP_070916822.1 phosphotriesterase-related protein | *Mycobacterium tuberculosis* |
| SEQ ID NO: 37 | WP_057370492.1 phosphotriesterase | *Mycobacterium tuberculosis* |
| SEQ ID NO: 38 | WP_041153720.1 phosphotriesterase | *Mycobacterium tuberculosis* |
| SEQ ID NO: 39 | WP_031751646.1 phosphotriesterase | *Mycobacterium tuberculosis* |
| SEQ ID NO: 40 | WP_031716625.1 phosphotriesterase | *Mycobacterium tuberculosis* |
| SEQ ID NO: 41 | WP_031707299.1 phosphotriesterase | *Mycobacterium tuberculosis* |
| SEQ ID NO: 42 | WP_052636504.1 phosphotriesterase | *Mycobacterium tuberculosis* |
| SEQ ID NO: 43 | WP_031711112.1 phosphotriesterase | *Mycobacterium tuberculosis* |
| SEQ ID NO: 44 | RYD10130.1 phosphotriesterase | *Mycobacterium tuberculosis* |
| SEQ ID NO: 45 | WP_017487637.1 phosphotriesterase | *Mycobacterium tuberculosis* |
| SEQ ID NO: 46 | WP_014585487.1 phosphotriesterase | *Mycobacterium tuberculosis* |
| SEQ ID NO: 47 | WP_102776491.1 phosphotriesterase-related protein | *Mycobacterium tuberculosis* |
| SEQ ID NO: 48 | WP_055384803.1 phosphotriesterase | *Mycobacterium tuberculosis* |
| SEQ ID NO: 49 | WP_057174556.1 phosphotriesterase | *Mycobacterium tuberculosis* |
| SEQ ID NO: 50 | 4IF2_A Chain A, Structure Of The Phosphotriesterase From Mycobacterium Tuberculosis | |
| SEQ ID NO: 51 | WP_055374072.1 phosphotriesterase | *Mycobacterium tuberculosis* |
| SEQ ID NO: 52 | WP_031725478.1 phosphotriesterase-related protein | *Mycobacterium tuberculosis* |
| SEQ ID NO: 53 | WP_031738135.1 phosphotriesterase | *Mycobacterium tuberculosis* |
| SEQ ID NO: 54 | WP_014000125.1 phosphotriesterase | *Mycobacterium canettii* |
| SEQ ID NO: 55 | WP_052632536.1 phosphotriesterase | *Mycobacterium tuberculosis* |
| SEQ ID NO: 56 | WP_031752956.1 phosphotriesterase | *Mycobacterium tuberculosis* |
| SEQ ID NO: 57 | WP_015288873.1 phosphotriesterase Php (parathion hydrolase) (PTE) (aryldialkylphosphatase) (paraoxonase) (a-esterase) (aryltriphosphatase) (paraoxon hydrolase) | *Mycobacterium canettii* |
| SEQ ID NO: 58 | WP_050895789.1 phosphotriesterase | *Mycobacterium tuberculosis* |
| SEQ ID NO: 59 | WP_031652122.1 phosphotriesterase | *Mycobacterium tuberculosis* |
| SEQ ID NO: 60 | WP_052655401.1 phosphotriesterase | *Mycobacterium tuberculosis* |
| SEQ ID NO: 61 | WP_057136546.1 phosphotriesterase | *Mycobacterium tuberculosis* |
| SEQ ID NO: 62 | WP_013988719.1 phosphotriesterase | *Mycobacterium tuberculosis* |

TABLE 2-continued

Protein sequences of PPH homologs (PTE Like Lactonases (PLLs).

| Sequence ID number | Accession no/Protein name. | Protein source |
|---|---|---|
| SEQ ID NO: 63 | WP_015291993.1 phosphotriesterase Php (parathion hydrolase) (PTE) (aryldialkylphosphatase) (paraoxonase) (a-esterase) (aryltriphosphatase) (paraoxon hydrolase) | *Mycobacterium canettii* |
| SEQ ID NO: 64 | AUS49258.1 phosphotriesterase | *Mycobacterium tuberculosis* |
| SEQ ID NO: 65 | SGD30548.1 parathion hydrolase | *Mycobacterium tuberculosis* |
| SEQ ID NO: 66 | WP_049873613.1 phosphotriesterase | *Mycobacterium tuberculosis* |
| SEQ ID NO: 67 | WP_085159921.1 phosphotriesterase-related protein | *Mycobacterium lacus* |
| SEQ ID NO: 68 | WP_009979649.1 MULTISPECIES: phosphotriesterase | *Mycobacterium avium* complex (MAC) |
| SEQ ID NO: 69 | WP_016810152.1 phosphotriesterase | *Mycobacterium tuberculosis* |
| SEQ ID NO: 70 | WP_054878907.1 phosphotriesterase | *Mycobacterium haemophilum* |
| SEQ ID NO: 71 | WP_063470385.1 MULTISPECIES: phosphotriesterase | *Mycobacterium* |
| SEQ ID NO: 72 | WP_069397147.1 phosphotriesterase | *Mycobacterium shimoidei* |
| SEQ ID NO: 73 | WP_113963099.1 phosphotriesterase-related protein | *Mycobacterium shimoidei* |
| SEQ ID NO: 74 | WP_085182214.1 phosphotriesterase-related protein | *Mycobacterium bohemicum* |
| SEQ ID NO: 75 | WP_075542160.1 phosphotriesterase | *Mycobacterium kansasii* |
| SEQ ID NO: 76 | WP_003874067.1 phosphotriesterase | *Mycobacterium avium* |
| SEQ ID NO: 77 | WP_082966984.1 phosphotriesterase-related protein | *Mycobacterium* sp. 852002-51163_SCH5372311 |
| SEQ ID NO: 78 | VDM86860.1 Parathion hydrolase precursor | *Mycobacterium* sp. DSM 104308 |
| SEQ ID NO: 79 | WP_047316850.1 phosphotriesterase | *Mycobacterium haemophilum* |
| SEQ ID NO: 80 | WP_075546659.1 phosphotriesterase | *Mycobacterium persicum* |
| SEQ ID NO: 81 | WP_122510178.1 phosphotriesterase-related protein | *Mycobacterium persicum* |
| SEQ ID NO: 82 | WP_023369760.1 MULTISPECIES: phosphotriesterase | *Mycobacterium* |
| SEQ ID NO: 83 | WP_067372810.1 phosphotriesterase | *Mycobacterium* sp. 1164966.3 |
| SEQ ID NO: 84 | WP_094028596.1 phosphotriesterase-related protein | *Mycobacterium avium* |
| SEQ ID NO: 85 | WP_066917426.1 phosphotriesterase | *Mycobacterium interjectum* |
| SEQ ID NO: 86 | WP_122440715.1 MULTISPECIES: phosphotriesterase-related protein | *Mycobacterium* |
| SEQ ID NO: 87 | ORB95896.1 phosphotriesterase-related protein | *Mycobacterium persicum* |
| SEQ ID NO: 88 | WP_083124567.1 phosphotriesterase-related protein | *Mycobacterium kansasii* |
| SEQ ID NO: 89 | WP_085199107.1 phosphotriesterase-related protein | *Mycobacterium fragae* |
| SEQ ID NO: 90 | WP_068024441.1 phosphotriesterase | *Mycobacterium kubicae* |

TABLE 2-continued

Protein sequences of PPH homologs (PTE Like Lactonases (PLLs).

| Sequence ID number | Accession no/Protein name. | Protein source |
|---|---|---|
| SEQ ID NO: 91 | WP_068157568.1 phosphotriesterase | *Mycobacterium kubicae* |
| SEQ ID NO: 92 | WP_068229952.1 phosphotriesterase | *Mycobacterium* sp. E3198 |
| SEQ ID NO: 93 | WP_085327573.1 phosphotriesterase-related protein | *Mycobacterium decipiens* |
| SEQ ID NO: 94 | WP_083116038.1 MULTISPECIES: phosphotriesterase-related protein | *Mycobacterium* |
| SEQ ID NO: 95 | WP_068061678.1 phosphotriesterase | *Mycobacterium* sp. E342 |
| SEQ ID NO: 96 | WP_067254020.1 phosphotriesterase | *Mycobacterium* sp. 852002-10029_SCH5224772 |
| SEQ ID NO: 97 | WP_036413589.1 phosphotriesterase | *Mycobacterium gastri* |
| SEQ ID NO: 98 | WP_085250078.1 phosphotriesterase-related protein | *Mycobacterium riyadhense* |
| SEQ ID NO: 99 | WP_046184118.1 phosphotriesterase | *Mycobacterium nebraskense* |
| SEQ ID NO: 100 | WP_103845650.1 phosphotriesterase-related protein | *Mycobacterium kansasii* |
| SEQ ID NO: 101 | WP_067099853.1 phosphotriesterase | *Mycobacterium* sp. 852002-40037_SCH5390672 |
| SEQ ID NO: 102 | WP_085072500.1 phosphotriesterase-related protein | *Mycobacterium kubicae* |
| SEQ ID NO: 103 | WP_117389070.1 phosphotriesterase-related protein | *Mycobacterium marinum* |
| SEQ ID NO: 104 | WP_065475716.1 phosphotriesterase | *Mycobacterium malmoense* |
| SEQ ID NO: 105 | WP_083178402.1 phosphotriesterase-related protein | *Mycobacterium scrofulaceum* |
| SEQ ID NO: 106 | WP_012392457.1 phosphotriesterase | *Mycobacterium marinum* |
| SEQ ID NO: 107 | WP_068094268.1 phosphotriesterase | *Mycobacterium* sp. E2497 |
| SEQ ID NO: 108 | WP_044509449.1 phosphotriesterase | *Mycobacterium simiae* |
| SEQ ID NO: 109 | WP_117431711.1 phosphotriesterase-related protein | *Mycobacterium marinum* |
| SEQ ID NO: 110 | WP_068140455.1 phosphotriesterase | *Mycobacterium* sp. E796 |

The invention will now be illustrated by the following non-limiting Examples.

EXAMPLES

Materials and Methods:

Cloning, Expression and Purification

A synthetic gene of putative parathion hydrolase (PPH) from *M. tuberculosis* (7) (Syntezza) was cloned into expression vector, pMal-c4X (NEB) at its EcoRI and PstI sites, for expression as fusions with maltose binding protein (MBP), to give the pMAL-c4x-PPH, which was then used to transform *Escherichia coli* DH5R cells.

Expression and Purification of PPH Wildtype and Variants

For large-scale production, LB medium (5 mL) containing 100 µg/mL ampicillin, and 0.5 mM MnCl$_2$ was inoculated with a single colony of *E. coli* BL21 (DE3) cells freshly transformed with pMAL-c4xPPH and grown overnight. The resulting culture added to 500 mL of the same medium and grown overnight at 30° C. The subsequent steps performed at 4° C. Cells were harvested by centrifugation and resuspended in lysis buffer [50 mM Tris-HCl (pH 8.0), 10 mM NaHCO3, the histidine-tagged protease inhibitor Cocktail (Sigma) diluted 1:500, and 100 µM ZnCl$_2$. After centrifugation, the supernatants were passed through an amylose column (NEB) equilibrated with column buffer [50 mM Tris (pH 8.0), 0.25 M NaCl, and 100 µM ZnCl2]. The fusion proteins eluted with column buffer supplemented with 10 mM maltose. The enzymatic activity of the collected fractions was analyzed with thiobutyryl butyrolactone (TBBL), and the fractions containing the highest activity were pooled together and dialyzed against assembly buffer. The purity of the fusion enzymes was established by 12% sodium dodecyl sulfate polyacrylamide gel electrophoresis (SDS-PAGE), and they were stored at 4° C.

Enzyme Kinetics.

The lactonase activity of PPH variants was analyzed by monitoring absorbance changes in 200 µL reaction volumes using 96-well plates and a microtiter plate reader (BioTeK, optical length of ~0.5 cm) at 25° C. For each substrate, reactions were performed as described (7), at the same concentration of organic solvent, regardless of substrate concentration. The substrates that were used are listed below, with the monitoring wavelength, extinction coefficient for the 0.5 cm pathway, and final organic solvent content: TBBL together with 0.5 mM 5,5'-dithiobis(2-nitrobenzoic acid) (DTNB) as an indicator (33) (412 nm, 7000 OD/M, 1% acetonitrile and 0.5% DMSO). The hydrolysis of C6-oxo-Homoserine lactone was monitored by following the appearance of the carboxylic acid products using a pH indicator as described previously (35). The reaction mixtures contained 0.01-1 mM lactone substrates in 0.2 M NaCl and 2.5 mM bicine buffer (pH 8.3), supplemented with 0.2-0.3 mM cresol purple as a pH indicator (577 nm, 1550-2500 OD/M, 1% DMSO). Initial rates ($V_0$) were corrected for the background rate of spontaneous hydrolysis in the absence of enzyme. Kinetic parameters were obtained by fitting initial rates directly to the Michaelis-Menten equation [$V_0=k_{cat}[E]_0[S]_0/([S]_0+K_M)$] with GraphPad. Error ranges relate to the standard deviation of the data obtained from at least three independent measurements.

Library Construction and Screening

Genetic libraries originating from the PPH gene were constructed using GeneMorph II Random Mutagenesis Kit (Agilent) adjusted to produce an average of 2 non-synonymous mutations per gene. Following the mutagenic PCR, libraries were cloned back into the modified pMAL vector as described for the pMal-c4X. The cloned libraries were transformed into BL21 cells and platted on LB plates supplemented with 100 µg/ml ampicillin and 1% (w/v) glucose. In each round of screening, approximately 600 randomly chosen single colonies were picked and grown overnight in 96 deep-well plates containing 500 µl of LB supplemented with 100 µg/mL ampicillin and 1% (w/v) glucose, at 37° C. with shaking. The overnight cultures were used to inoculate (at 1:20 dilution) fresh 500 µl LB supplemented with 200 µg/mL ampicillin in 96 deep-well plates. Cells were grown at 30° C. with shaking for about 4 h, to an $OD_{600}$=0.6-1.0, Isopropyl β-d-1-thiogalactopyranoside (IPTG) was then added (final concentration 0.4 mM) to induce expression of the phosphotriesterase-like lactonase variants. Following overnight incubation at 20° C., the cells were pelleted and frozen at −80° C. Cells were resuspended in lysis buffer (100 mM Tris pH 8, 100 µM MnCl$_2$, 150 mM NaCl, 100 µg/mL lysozyme, 0.5 unit/mL benzonase, 0.1% triton X-100, 1:500 protease inhibitor cocktail (Sigma P8849) for 1 h shaking at 960 RPM at 25° C.). The lysates were clarified by centrifugation, incubated in 45° C., cooled to room temperature, diluted in activity buffer, and assayed for hydrolysis of TBBL together with 0.5 mM 5,5'-dithiobis (2-nitrobenzoic acid) (DTNB) as an indicator. In each round, variants with top activities were selected to serve as parents for the next round, where their genes were shuffled and mutated using GeneMorphII kit.

Thermostability and Shelf Life of wtPPH and Its Evolved Variants

The thermal stability was tested by pre-incubating the enzyme variants at temperatures ranging between 4-70° C. for 1 h, was set to be 0.5 µM, and TBBL (6) to 0.2 mM. Residual activity was than measured by following lactonase activity at room temperature. For shelf life measurements, the lactonase activity of both wtPPH and the evolved variants (at 0.5 µM enzyme concentration) was measured with 0.1 mM TBBL for 18 days following purification and keeping the enzyme solution in room temperature.

Figure 1A:
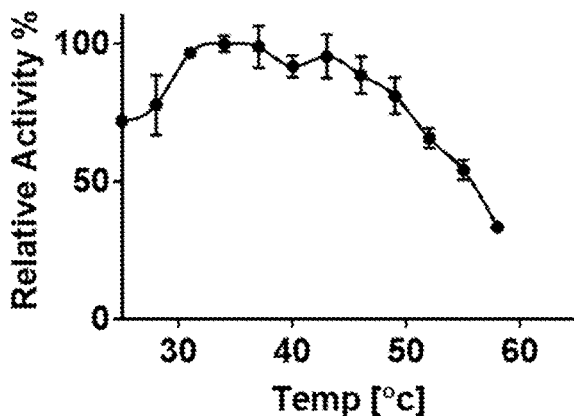
FIGS. 1A-B show the biochemical characterization of putative parathion hydrolase from *M. tuberclorosis* (PPH). PPH was recombinantly expressed in *E. coli*-BL21(DE3) followed by a purification step using amylose column and PPH activity was analyzed with c6-oxo-HSL ($E_o$=0.01 μM at 25° C.). The hydrolysis of c6-oxo-HSL was monitored by the release of their carboxylic acid products using cresol purple, a pH indicator. (a) PPH was found to be active in a range of temperatures; activity was tested with thiobutyryl butyrolactone (TBBL) (6) (thiobutyryl butyrolactone). Its optimal activity was 40° C., and it maintained 80% of its activity up to 50° C. $K_M$ value of 0.056±0.009 mM, 10.16±0.01 $s^{-1}$, $k_{cat}/K_M$ of 1.81*10$^5$ $s^{-1}$/M$^{-1}$ (b).
Figure 1B:
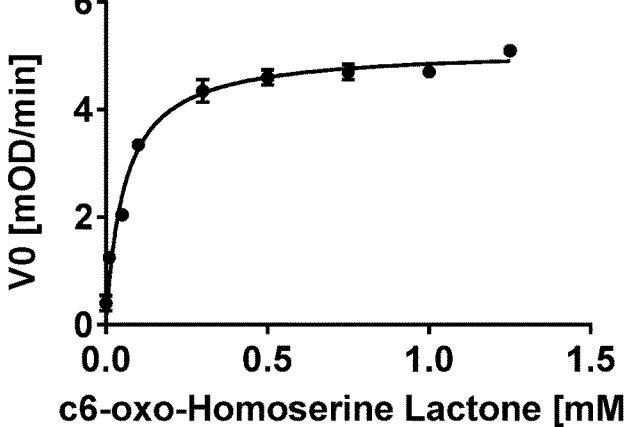

Example 1. Recombinant Expression, Purification and Biochemical Characterizations of Enzymes with c6-oxo-HSL The encoding genes of PPH from *M. tuberculosis* and its evolved variants, were cloned into expression vector, pMal-c4X, and overexpressed as a fusion protein with a high-binding mutant (A313V) maltose-binding protein in *E. coli*-BL21 (DE3) (SEQ ID NO: 10). Next, cells were lyzed and protein was purified using an amylose column (NEB). Following purification we tested, the optimal temperature of the enzymes, their thermal stability and shelf life with chromogenic substrate (TBBL, thiobutyryl butyrolactone). Their activity with C6-oxo-HSL (aka N-Caproyl-L-homoserine lactone, N-[(3S)-Tetrahydro-2-oxo-3-furanyl]hexanamide, HHL), the lactone secreted by the plant pathogen *E. amylovora*, using the pH indicator assay, as previously described (7), see FIGS. 1B and 2A; PPH exhibited high activity with C6-oxo-HSL, with $K_{cat}/K_M$ values of 1.24*10$^5$ s$^{-1}$/M$^{-1}$ (see Table 3). Its optimal temperature is at 40° C. (FIG. 1A) and in terms of thermal stability it exhibited 50% residual activity at 55° C., see FIG. 2B.

Example 2. Constructing Random Genetic Libraries and Isolating Improved Variants with Higher Activity, Thermal Stability and Shelf Life PPH coding gene was used to construct genetic library using Gene Morph random mutagenesis kit (Agilent). Following PCR amplification, the resulting PCR products was then used as templates for a nested PCR with external primers, following digestion with EcoRI and PstI and ligation into pMAL-c2x, the library plasmid was electroporated into *E. coli* DH5α and library size was estimated to be 5000, and isolation of plasmid DNA. Individual clones of the unselected library were sequenced and an average of 2-3 point mutations per gene was identified. Using several rounds of creating random mutagenesis (library size of 3-4*10$^5$ variants) and screening (600 variants per round) for increased thermal stability we have isolated two variants with unique sequences, see FIG. 2: The variants harboring the following mutations: G58V in variant PPH_R2: P4-D5 [G59V; SEQ ID NO: 11] and H171Y in variant PPH_R2: P8-D12 [H172Y; SEQ ID NO: 12], that present high catalytic activity $k_{cat}/K_M$ of 10$^5$ s$^{-1}$M$^{-1}$ in the same order of magnitude as the wildtype enzyme, Table 3, for PPH_R2: P4-D5 the $k_{cat}/K_M$ increased by 2 folds, see Table 3 and FIG. 2A. Moreover, they have increased thermal stability exhibiting about 15 degrees increase in their 50% residual activity, and maintain 100% of their activity up to 60° C. (FIG. 2B). We further analyzed the shelf life of the evolved variants compered to wtPPH, and as can be seen in FIG. 2C, following 13 days from purification, variant PPH_R2: P4-D5 had about 50% residual activity, while wtPPH had 20% of its activity. This makes them more suitable for use in agriculture as antibacterial treatment.

TABLE 3

| Kinetic parameters of PPH and its evolved variants | | | |
|---|---|---|---|
| | $k_{cat}$ [sec$^{-1}$] | $K_M$ [mM] | $K_{cat}/K_M$ [s$^{-1}$ M$^{-1}$] |
| wtPPH | 10.16 ± 0.01 | 0.056 ± 0.009 | 1.80*10$^5$ |
| PPH_R2:P4-D5 | 18.66 ± 1.16 | 0.050 ± 0.010 | 3.70*10$^5$ |
| PPH_R2:P8-D12 | 10.16 ± 1.46 | 0.105 ± 0.019 | 2.04*10$^5$ |

Example 3. Wild Type QQ PPH Lactonase Inhibits Extracellular Polysaccharide Formation in Culture As a measure of bacterial virulence as exhibited in the formation of extracellular polysaccharide (EPS) matrix Levan production was observed spectroscopically at 400 nm following supplementing 500 mM sucrose, according to a previously described protocol (Molina et al., 2005).

Figure 3:
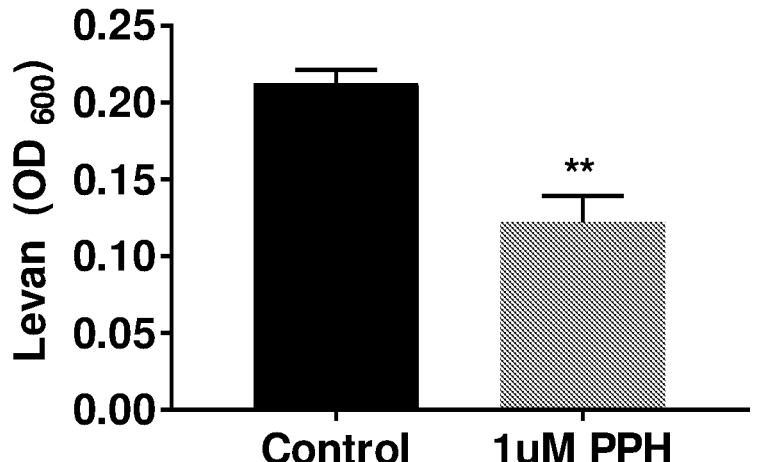
FIG. 3 is a bar graph showing the ability of wild-type QQ lactonase (PPH) to reduce the production of Levan in *E. amylovora*. Levan production was observed spectroscopically in *E. amylovora* (isolate Ea2tp0) cultures grown in LB medium supplemented with sucrose (buffer), with or without the addition of 1 uM of QQ lactonase after 3 h following the addition of sucrose.

A 30% reduction in EPS production was observed when purified wild-type PPH protein was applied to a cell culture of *E. amylovora* (FIG. 3). It is expected that the G59V and H172Y mutants are at least as effective in reducing EPS production.

Example 4. Treatment of Fire Blight with PPH Mutant

Figure 4A:
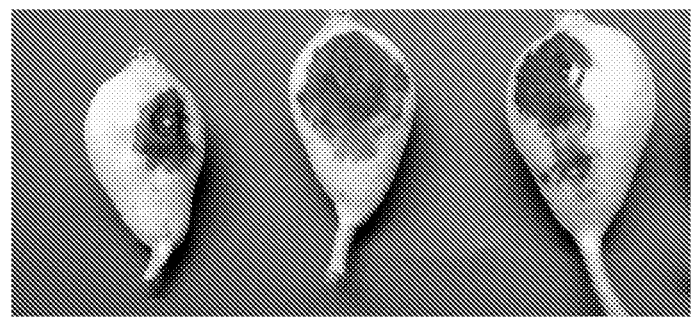
FIGS. 4A-C depict a pathogenicity assay of *E. amylovora* infection in planta. Pear fruits were inoculated with *E. amylovora* cell suspension ($10^8$ CFU/ml) incubated with activity buffer (a) or with *E. amylovora* cell suspension incubated with 2 μM PPH purified from *M. tuberculosis* (7) (b). After 7 days of incubation at 28° C., noninoculated controls remained asymptomatic throughout the experiments, and inoculated pears following incubation with purified PPH appeared less symptomatic than the control (only *E. amylovora* culture and buffer). Ten pears in the first row were treated with bacteria and enzyme's activity buffer, second row—bacteria with wild type PPH and third row—bacteria with PPH_R2: P4-D5 (corresponding to G59V-PPH) (C).
Figure 4B:
Figure 4C:

To assess the ability of QQ lactonases to inhibit fireblight disease in pears, we have established pathogenicity assays in planta with the wildtype PPH enzyme, following a previously described protocol (28) (29). Wounded immature pear fruits were inoculated with *E. amylovora* and then monitored for symptom development. Pears were subjected to three treatments; bacteria culture alone, bacteria culture with purified wild type or mutant PPH enzyme, bacteria culture with the enzyme activity buffer in a 1:1 ratio, following incubation for 1 h at 20° C., 300 rpm. To do so, immature pears (*Pyrus communis*, 'safadona') were surface sterilized with 70% ethanol and pricked with a sterile needle by bacteria culture alone, bacteria culture with lactonase buffer as a control and bacteria that were incubated with the enzyme, and incubated in a humidified chamber at 28° C. Symptoms were recorded at 2, 4, 6, and 7 days post inoculation. After 7 days of incubation at 28° C., disease symptoms were measured. Noninoculated controls remained asymptomatic throughout the experiments. Each treatment consisted of 10 pears, and the experiment was repeated in three independent trials over time. As can be seen in FIGS. 4A-C, the Fire blight lesions in the pears that were pricked with bacteria-enzyme (PPH from *Mycobacterium tuberculosis*) solution were not as dark and spread as compared to the control, and the PPH_R2: P4-D5 mutant (SEQ ID NO: 11) (FIG. 4C, 3$^{rd}$ row from the top) was more effective than the wild-type enzyme (SEQ ID NO: 10) (FIG. 4C, 2$^{nd}$ row from the top) in controlling the infection.

The efficacy of a mutated phosphotriesterase-like lactonase bearing a mutation at H172, such as H172Y (consisting of the amino acid sequence as set forth in SEQ ID NO: 3 or 12), or any one of the PLLs of SEQ ID NOs: 16-110, optionally expressed as a MBP-fusion protein, with a substitution of an amino acid residue corresponding to G59V or H172Y in SEQ ID NO: 1, in treating or preventing fire blight is tested similarly as described above for the wild-type PPH and G59V PPH. Higher efficacy of these mutants in reducing and inhibiting fireblight disease than the wild-type mutant is expected.

Example 5. Treatment of Fire Blight on Blossoms with PPH and Its Mutant in Growth Chamber and in the Field Method. Blooming branches with open flowers of *P. communis*, 'Spadona' were placed in a growth camber at 22° C. (12 h day, 12 h night). Enzyme solutions containing 4 μM of wtPPH and its evolved mutant were either sprayed on the flowers, and 2 hours later, cell suspension (10$^7$ CFU/ml) of *E. amylovora* were sprayed on the flowers (pre-infection), or both enzyme and culture was mixed in a 1:1 ratio for an half an hour and then sprayed (mix). *E. amylovora* culture alone was used as a control. The experiment was done in three repeats, in each repeat 10 blossoms were used. The air condition and the light in the chamber where shut off for 2 h after infection, in order to prevent dryness and elevated temperature in the chamber.

For the field experiment, blossoms of *P. communis* 'Spadona' pear trees were sprayed with different enzyme solutions; wtPPH and the evolved mutant PPH-G58V (4 μM). Different times of application were tested; 30-45 minutes before or simultaneously to infection (by mixing the enzymes solution with the culture for half an hour before spraying). In all cases 10$^9$ CFU/ml *E. amylovora* bacterial culture was used. After the infection, the blossoms were covered with plastic bag overnight to ensure high humidity. The experiment was done in five repeats, every repeat contained 10 blossoms, 5 blossoms on each side of the tree. No more than 4 treatments on a tree. Disease symptoms were evaluated following evaluation 13 days post inoculation by counting the diseased flowers in each blossom and 24 days post inoculation by counting infected blossom. Similar experiment was done in *P. communis Costia* pears; disease evaluation was done after 12 and 35 days post infection in the same manner. The field trails were conducted at Hula Valley Orchards Experimental Farm in the north (33° 8'58.10"N 35°37'16.93"E) for two consecutive years 2019, 2020. Data are shown for of *P. communis* 'Spadona' pear trees 24 days post inoculation by counting infected blossom.

Results. We tested the ability of the PPH wild-type and evolved mutant to inhibit pathogenicity in blossoms, in growth chamber. As FIGS. 5A-B indicate, 6 days post inoculation, 4 μM of both wtPPH and PPH-G58V inhibited flower infection by 30% relative to untreated control when they were applied prior to infection with the pathogen; the oxlinc acid inhibited by 45%. When the enzyme and bacteria were mixed together and then sprayed on the blossoms, the treatment was still effective (20% inhibition) but infection signs were increased.

In the field, a clear advantage was observed for the pre-incubation of the mutant over the mix treatment, with close to 70% inhibition by PPH-G58V with a similar inhibition range of the antibiotic used today, oxolinic acid, FIG. 5C.

The efficacy of a mutated phosphotriesterase-like lactonase bearing a mutation at H172, such as H172Y (consisting of the amino acid sequence as set forth in SEQ ID NO: 3 or 12), or any one of the PLLs of SEQ ID NOs: 16-110, optionally expressed as a MBP-fusion protein, with a substitution of an amino acid residue corresponding to G59V or H172Y in SEQ ID NO: 1, in treating or preventing fire blight is tested similarly as described above for the wild-type PPH and G59V PPH. Higher efficacy of these mutants in reducing and inhibiting fireblight disease than the wild-type mutant is expected.

Example 6. Treatment of Fire Blight with a Combination of PPH Mutant and Copper Salt Copper is well known as a protectant agent for use in inhibiting *E. amylovora* infection (in concentration of 0.19 g/L.

This preliminary experiment was done in order to check the possibility of using lower dosage of Cu$^{2+}$ with PPH_R2: P4-D5 (PPH-G58V), in order to achieve additive affect. A mixture of single colony of *E. amylovora* from two isolates (named 511 and 576) was cultured in LB medium (10 mL)

over-night, refreshed for 4 h, and each isolate, were nor-malized to OD$_{600}$ 0.5. Culture suspensions were mixed for 30 min in room temperature with: (i) 0.25 μM CuSO$_4$, (ii) 4 μM PPH_R2: P4-D5 and 0.25 μM CuSO$_4$. Untreated culture suspensions were used as a control.

Immature pears were sterilized for a few seconds with 1% HCl follow by H$_2$O wash, and punctured with a sterile needle dipped in the different mix. The treated fruit were incubated in a humidified chamber at 25° C. Disease symptoms diameter were measured after 9 days. Each treatment were done in 3 repeats, each repeat contain 3-6 immature pears.

Preliminary data indicates that the use of 0.25 mM CuSO$_4$ significantly inhibits the infection degree of *E. amilovora* in immature pears, and the addition of 4 μM PPH_R2: P4-D5 to 0.25 mM CuSO$_4$ solution gave a better effect than CuSO$_4$ alone.

The results in FIG. 7 show that the combination of CuSO$_4$ with the mutant enzyme PPH_R2: P4-D5 resulted in complete inhibition of the symptoms—as none of the pears were infected, as can be seen in the % of infection (n=3), calculated from the infection diameter (n=12-18 immature fruits).

Fruits and blossoms are treated for fire blight on pear fruit and blossom with variant concentrations of CuSO$_4$ (e.g. 0.0125, 0.025, 0.25 and 2.5 mM) alone or in combination with wild-type or mutant enzyme at e.g. 4 μM). Controls are untreated, treated with buffer alone or enzyme alone. The mutated enzyme tested is a mutated phosphotriesterase-like lactonase bearing a mutation at G59, such as G59V (consisting of the amino acid sequence as set forth in SEQ ID NO: 2 or 11), H172, such as H172Y (consisting of the amino acid sequence as set forth in SEQ ID NO: 3 or 12), or any one of the PLLs of SEQ ID NOs: 16-110, optionally expressed as a MBP-fusion protein, with a substitution of an amino acid residue corresponding to G59V or H172Y in SEQ ID NO: 1, in treating or preventing fire blight is tested similarly as described above for the wild-type PPH and G59V PPH. Higher efficacy of these mutants in reducing and inhibiting fireblight disease than the wild-type mutant is expected.

REFERENCES

1. McManus P S, Stockwell V O, Sundin G W, Jones A L. 2002. Antibiotic Use in Plant Agriculture. *Annu. Rev. Phytopathol.* 40(1):443-65
2. Põllumaa L, Alamäe T, Mäe A. 2012. Quorum sensing and expression of virulence in pectobacteria
3. Arnold D L, Lovell H C, Jackson R W, Mansfield J W. 2011. *Pseudomonas syringae* pv. *phaseolicola*: From "has bean" to supermodel. *Mol. Plant Pathol.*
4. Licciardello G, Bertani I, Steindler L, Bella P, Venturi V, Catara V. 2007. *Pseudomonas corrugata* contains a conserved N-acyl homoserine lactone quorum sensing system; its role in tomato pathogenicity and tobacco hypersensitivity response. *FEMS Microbiol. Ecol.*
5. Duffy B, Schärer H J, Bünter M, Klay A, Holliger E. 2005. Regulatory measures against *Erwinia amylovora* in Switzerland
6. Khersonsky O, Tawfik D S. 2006. Chromogenic and fluorogenic assays for the lactonase activity of serum paraoxonases. *ChemBioChem*
7. Afriat L, Roodveldt C, Manco G, Tawfik D S. 2006. The latent promiscuity of newly identified microbial lactonases is linked to a recently diverged phosphotriesterase. *Biochemistry.* 45(46): 13677-86

8. Jayaraman A, Wood T K. 2008. Bacterial quorum sensing: signals, circuits, and implications for biofilms and disease. *Annu. Rev. Biomed. Eng.* 10:145-67
9. Vrancken K, Holtappels M, Schoofs H, Deckers T, Valcke R. 2013. Pathogenicity and infection strategies of the fire blight pathogen *Erwinia amylovora* in Rosaceae: State of the art
10. Chen F, Gao Y, Chen X, Yu Z, Li X. 2013. Quorum quenching enzymes and their application in degrading signal molecules to block quorum sensing-dependent infection
11. Zhang L, Wang H, Liu X, Zhou W, Rao Z. 2019. The crystal structure of the phosphotriesterase from *M. tuberculosis*, another member of phosphotriesterase-like lactonase family. *Biochem. Biophys. Res. Commun.*
12. Wierenga R K. 2001. The TIM-barrel fold: A versatile framework for efficient enzymes
13. Pieper U, Webb B M, Barkan D T, Schneidman-Duhovny D, Schlessinger A, et al. 2011. ModBase, a database of annotated comparative protein structure models, and associated resources. *Nucleic Acids Res.*
14. Freudl R. 2018. Signal peptides for recombinant protein secretion in bacterial expression systems
15. Venturi V, Venuti C, Devescovi G, Lucchese C, Friscina A, et al. 2004. The plant pathogen *Erwinia amylovora* produces acyl-homoserine lactone signal molecules in vitro and in planta. *FEMS Microbiol. Lett.* 241(2):179-83
16. Crépin A, Barbey C, Beury-Cirou A, Hélias V, Taupin L, et al. 2012. Quorum sensing signaling molecules produced by reference and emerging soft-rot bacteria (*Dickeya* and *Pectobacterium* spp.). *PLoS One*
17. Crépin A, Beury-Cirou A, Barbey C, Farmer C, Hélias V, et al. 2012. N-Acyl Homoserine Lactones in diverse *Pectobacterium* and *Dickeya* plant pathogens: Diversity, abundance, and involvement in virulence. *Sensors*
18. Bhat K A, Masood S D, Bhat N A, Bhat M A, Razvi S M, et al. 2010. Current status of post harvest soft rot in vegetables: A review. *Asian J. Plant Sci.*
19. Loh J, Pierson E A, Pierson L S, Stacey G, Chatterjee A. 2002. Quorum sensing in plant-associated bacteria
20. Barnard A M L, Salmond G P C. 2007. Quorum sensing in *Erwinia* species. *Anal. Bioanal. Chem.* 387 (2):415-23
21. Lade H, Paul D, Kweon J H. 2014. N-Acyl Homoserine Lactone-Mediated Quorum Sensing with Special Reference to Use of Quorum Quenching Bacteria in Membrane Biofouling Control. *Biomed Res. Int.*
22. Schuster M, Greenberg E P. 2006. A network of networks: Quorum-sensing gene regulation in *Pseudomonas aeruginosa*
23. Li T, Wang D, Liu N, Ma Y, Ding T, et al. 2018. Inhibition of quorum sensing-controlled virulence factors and biofilm formation in *Pseudomonas fluorescens* by cinnamaldehyde. *Int. J. Food Microbiol.*
24. Conway B A, Greenberg E P. 2002. Quorum-sensing signals and quorum-sensing genes in *Burkholderia vietnamiensis. J. Bacteriol.*
25. Venturi V, Friscina A, Bertani I, Devescovi G, Aguilar C. 2004. Quorum sensing in the *Burkholderia cepacia* complex
26. Duerkop B A, Varga J, Chandler J R, Peterson S B, Herman J P, et al. 2009. Quorum-sensing control of antibiotic synthesis in *Burkholderia thailandensis. J. Bacteriol.*

27. Choi J H, Lee S Y. 2004. Secretory and extracellular production of recombinant proteins using *Escherichia coli*

28. Molina L, Rezzonico F, Défago G, Duffy B. 2005. Autoinduction in *Erwinia amylovora*: Evidence of an acyl-homoserine lactone signal in the fire blight pathogen. *J. Bacteriol.* 187(9):3206-13

29. Zhao Y, Blumer S E, Sundin G W. 2005. Identification of *Erwinia amylovora* genes induced during infection of immature pear tissue. *J. Bacteriol.*

What is claimed is:

1. A mutated phosphotriesterase-like lactonase having at least 90% identity with the wild-type putative parathion hydrolase from *M. tuberclorosis* of SEQ ID NO: 1, in which an amino acid residue corresponding to position 59 or 172 of SEQ ID NO: 1 is substituted, wherein a glycine residue corresponding to G59 is substituted by an amino acid residue selected from valine, alanine, leucine, and isoleucine, or a histidine residue corresponding to H172 is substituted by an amino acid residue selected from tyrosine, phenylalanine and tryptophan, and said mutated phosphotriesterase-like lactonase has substantially identical TIM-barrel fold to a wild-type phosphotriesterase-like lactonase and preserves catalytic residues in its active site.

2. The mutated phosphotriesterase-like lactonase of claim 1, wherein a glycine residue corresponding to G59 of SEQ ID NO: 1 is substituted by valine; or a histidine residue corresponding to H172 of SEQ ID NO: 1 is substituted by tyrosine.

3. The mutated phosphotriesterase-like lactonase of claim 2 comprising or essentially consisting of the amino acid sequence as set forth in SEQ ID NO: 2 or SEQ ID NO: 3.

4. The mutated phosphotriesterase-like lactonase of claim 1, wherein said mutated phosphotriesterase-like lactonase has an increased thermostability in comparison with thermostability of a non-mutated wild-type phosphotriesterase-like lactonase or substantially similar or higher lactonase catalytic activity provided with N-(3-oxo-hexanoyl)-homoserine lactone as a substrate in comparison with said non-mutated wild-type phosphotriesterase-like lactonase.

5. The mutated phosphotriesterase-like lactonase of claim 4, wherein said increased thermostability expressed as $T_{50}$ is about 50° C. to about 80° C.

6. The mutated phosphotriesterase-like lactonase of claim 4, having an extended shelf-life as compared with said non-mutated wild-type phosphotriesterase-like lactonase.

7. The mutated phosphotriesterase-like lactonase of claim 1, wherein a glycine residue corresponding to G59 of SEQ ID NO: 1 is substituted by valine or a histidine residue corresponding to H172 of SEQ ID NO: 1 is substituted by tyrosine; and said mutated phosphotriesterase-like lactonase has an increased thermostability in comparison with thermostability of a non-mutated wild-type phosphotriesterase-like lactonase or substantially similar or higher lactonase catalytic activity provided with N-(3-oxo-hexanoyl)-homoserine lactone as a substrate in comparison with said non-mutated wild-type phosphotriesterase-like lactonase.

8. The mutated phosphotriesterase-like lactonase of claim 7, comprising or essentially consisting of the amino acid sequence as set forth in SEQ ID NO: 2 or SEQ ID NO: 3; said increased thermostability expressed as $T_{50}$ is about 55° C. to about 80° C., or said mutated phosphotriesterase-like lactonase has an extended shelf-life as compared with said non-mutated wild-type phosphotriesterase-like lactonase.

9. The mutated phosphotriesterase-like lactonase of claim 1, comprising the PPH of SEQ ID NO: 1 in which the glycine residue at position 59 is substituted by an amino acid residue selected from valine, alanine, leucine, and isoleucine, or the histidine residue at position 172 is substituted by an amino acid residue selected from tyrosine, phenylalanine and tryptophan.

10. A composition comprising the mutated phosphotri-esterase-like lactonase of claim 1, optionally further comprising a copper salt.

11. The composition of claim 10, wherein said copper salt is CuSO$_4$.

12. An isolated nucleic acid molecule comprising a nucleic acid sequence encoding a mutated phosphotri-esterase-like lactonase of claim 1.

13. The nucleic acid molecule of claim 12 comprising a nucleic acid sequence as set forth in SEQ ID NO: 5, SEQ ID NO: 6, SEQ ID NO: 8, SEQ ID NO: 9, SEQ ID NO: 14 or SEQ ID NO: 15.

14. An expression vector comprising the nucleic acid molecule of claim 12 operatively linked to a promoter.

15. A cell comprising the isolated nucleic acid molecule of claim 12 or the expression vector of claim 14.

16. The cell of claim 15, selected from a bacterial, fungal, mammal or plant cell.

17. The cell of claim 16, wherein said cell is *E. coli*.

18. A plant or a part, organ or a plant propagation material thereof, at least partly covered or coated with a mutated phosphotriesterase-like lactonase of claim 1.

19. A plant or a part, organ or a plant propagation material thereof, at least partly covered or coated with a composition of claim 10.

20. A method for treating or preventing infection of a bacterium in a plant or a part, organ or a plant propagation material thereof, said plant being infected by or susceptible to a bacterium secreting a lactone selected from N-(3-hydroxybutanoyl)-L-homoserine lactone (C4-HSL), N-(3-oxo-hexanoyl)-homoserine lactone (C6-oxo-HSL), N-[(3S)-tetrahydro-2-oxo-3-furanyl]octanamide (C8-oxo-HSL), and N-[(3S)-tetrahydro-furanyl]decanamide (C10-HSL), said method comprising applying on said plant or said part, organ or plant propagation material thereof, the wild-type putative parathion hydrolase from *M. tuber-clorosis* of SEQ ID NO: 1, the mutated phosphotri-esterase-like lactonase of claim 1, or the composition of claim 10.

21. The method of claim 20, wherein said bacterium is selected from the group consisting of *Erwinia amylovora, Pectobacterium carotovorum, Pseudomonas syringae, Pseudomonas corrugata, Burkholderia vietnamiensis, Burkholderia cepacia, Burkholderia thailandensis* and *Pseudomonas aeruginosa*, including any pathovars.

22. The method of claim 21, wherein said bacterium is *Erwinia amylovora, Pectobacterium carotovorum*, or *Pseudomonas syringae*.

23. The method of claim 22, wherein said *Pseudomonas syringae* is *Pseudomonas tomato* (formerly known as *Pseudomonas syringae* pv. *tomato*).

24. The method of claim 20, wherein said putative para-thion hydrolase from *M. tuberclorosis*, said mutated phos-photriesterase-like lactonase, or said composition, and a separate composition comprising a copper salt, are separately applied to said plant, part, organ or plant propagation material of said plant.

25. The method of claim 20, comprising applying the mutated phosphotriesterase-like lactonase wherein a glycine residue corresponding to G59 of SEQ ID NO: 1 is substi-tuted by valine, or the phosphotriesterase-like lactonase wherein a histidine residue corresponding to H172 of SEQ ID NO: 1 is substituted by tyrosine.

26. The method of claim 24, wherein said copper salt is CuSO$_4$.

27. The method of claim 25, wherein said mutated phos-photriesterase-like lactonase wherein a glycine residue cor-responding to G59 of SEQ ID NO: 1 is substituted by valine comprises or essentially consists of the amino acid sequence as set forth in SEQ ID NO: 2 or SEQ ID NO: 11; or the phosphotriesterase-like lactonase wherein a histidine residue corresponding to H172 of SEQ ID NO: 1 is substituted by tyrosine comprises or essentially consists of the amino acid sequence as set forth in SEQ ID NO: 3 or SEQ ID NO: 12.

\*  \*  \*  \*  \*

SEQUENCE LISTING

<160> NUMBER OF SEQ ID NOS: 116

<210> SEQ ID NO 1
<211> LENGTH: 330
<212> TYPE: PRT
<213> ORGANISM: Mycobacterium tuberculosis

<400> SEQUENCE: 1

```
Met Ile Ser Glu Phe Pro Glu Leu Asn Thr Ala Arg Gly Pro Ile Asp
1               5                   10                  15

Thr Ala Asp Leu Gly Val Thr Leu Met His Glu His Val Phe Ile Met
            20                  25                  30

Thr Thr Glu Ile Ala Gln Asn Tyr Pro Glu Ala Trp Gly Asp Glu Asp
        35                  40                  45

Lys Arg Val Ala Gly Ala Ile Ala Arg Leu Gly Glu Leu Lys Ala Arg
    50                  55                  60

Gly Val Asp Thr Ile Val Asp Leu Thr Val Ile Gly Leu Gly Arg Tyr
65                  70                  75                  80

Ile Pro Arg Ile Ala Arg Val Ala Ala Ala Thr Glu Leu Asn Ile Val
                85                  90                  95

Val Ala Thr Gly Leu Tyr Thr Tyr Asn Asp Val Pro Phe Tyr Phe His
            100                 105                 110

Tyr Leu Gly Pro Gly Ala Gln Leu Asp Gly Pro Glu Ile Met Thr Asp
        115                 120                 125

Met Phe Val Arg Asp Ile Glu His Gly Ile Ala Asp Thr Gly Ile Lys
    130                 135                 140

Ala Gly Ile Leu Lys Cys Ala Thr Asp Glu Pro Gly Leu Thr Pro Gly
145                 150                 155                 160

Val Glu Arg Val Leu Arg Ala Val Ala Gln Ala His Lys Arg Thr Gly
                165                 170                 175

Ala Pro Ile Ser Thr His Thr His Ala Gly Leu Arg Arg Gly Leu Asp
            180                 185                 190

Gln Gln Arg Ile Phe Ala Glu Glu Gly Val Asp Leu Ser Arg Val Val
        195                 200                 205

Ile Gly His Cys Gly Asp Ser Thr Asp Val Gly Tyr Leu Glu Glu Leu
    210                 215                 220

Ile Ala Ala Gly Ser Tyr Leu Gly Met Asp Arg Phe Gly Val Asp Val
225                 230                 235                 240

Ile Ser Pro Phe Gln Asp Arg Val Asn Ile Val Ala Arg Met Cys Glu
                245                 250                 255

Arg Gly His Ala Asp Lys Met Val Leu Ser His Asp Ala Cys Cys Tyr
            260                 265                 270

Phe Asp Ala Leu Pro Glu Glu Leu Val Pro Val Ala Met Pro Asn Trp
        275                 280                 285

His Tyr Leu His Ile His Asn Asp Val Ile Pro Ala Leu Lys Gln His
    290                 295                 300

Gly Val Thr Asp Glu Gln Leu His Thr Met Leu Val Asp Asn Pro Arg
305                 310                 315                 320

Arg Ile Phe Glu Arg Gln Gly Gly Tyr Gln
                325                 330
```

-continued

<210> SEQ ID NO 2
<211> LENGTH: 330
<212> TYPE: PRT
<213> ORGANISM: Mycobacterium tuberculosis

<400> SEQUENCE: 2

```
Met Ile Ser Glu Phe Pro Glu Leu Asn Thr Ala Arg Gly Pro Ile Asp
1               5                   10                  15

Thr Ala Asp Leu Gly Val Thr Leu Met His Glu His Val Phe Ile Met
            20                  25                  30

Thr Thr Glu Ile Ala Gln Asn Tyr Pro Glu Ala Trp Gly Asp Glu Asp
        35                  40                  45

Lys Arg Val Ala Gly Ala Ile Ala Arg Leu Val Glu Leu Lys Ala Arg
    50                  55                  60

Gly Val Asp Thr Ile Val Asp Leu Thr Val Ile Gly Leu Gly Arg Tyr
65                  70                  75                  80

Ile Pro Arg Ile Ala Arg Val Ala Ala Ala Thr Glu Leu Asn Ile Val
                85                  90                  95

Val Ala Thr Gly Leu Tyr Thr Tyr Asn Asp Val Pro Phe Tyr Phe His
            100                 105                 110

Tyr Leu Gly Pro Gly Ala Gln Leu Asp Gly Pro Glu Ile Met Thr Asp
        115                 120                 125

Met Phe Val Arg Asp Ile Glu His Gly Ile Ala Asp Thr Gly Ile Lys
    130                 135                 140

Ala Gly Ile Leu Lys Cys Ala Thr Asp Glu Pro Gly Leu Thr Pro Gly
145                 150                 155                 160

Val Glu Arg Val Leu Arg Ala Val Ala Gln Ala His Lys Arg Thr Gly
                165                 170                 175

Ala Pro Ile Ser Thr His Thr His Ala Gly Leu Arg Arg Gly Leu Asp
            180                 185                 190

Gln Gln Arg Ile Phe Ala Glu Glu Gly Val Asp Leu Ser Arg Val Val
        195                 200                 205

Ile Gly His Cys Gly Asp Ser Thr Asp Val Gly Tyr Leu Glu Glu Leu
    210                 215                 220

Ile Ala Ala Gly Ser Tyr Leu Gly Met Asp Arg Phe Gly Val Asp Val
225                 230                 235                 240

Ile Ser Pro Phe Gln Asp Arg Val Asn Ile Val Ala Arg Met Cys Glu
                245                 250                 255

Arg Gly His Ala Asp Lys Met Val Leu Ser His Asp Ala Cys Cys Tyr
            260                 265                 270

Phe Asp Ala Leu Pro Glu Glu Leu Val Pro Val Ala Met Pro Asn Trp
        275                 280                 285

His Tyr Leu His Ile His Asn Asp Val Ile Pro Ala Leu Lys Gln His
    290                 295                 300

Gly Val Thr Asp Glu Gln Leu His Thr Met Leu Val Asp Asn Pro Arg
305                 310                 315                 320

Arg Ile Phe Glu Arg Gln Gly Gly Tyr Gln
                325                 330
```

<210> SEQ ID NO 3
<211> LENGTH: 330
<212> TYPE: PRT
<213> ORGANISM: Mycobacterium tuberculosis -continued

<400> SEQUENCE: 3

```
Met Ile Ser Glu Phe Pro Glu Leu Asn Thr Ala Arg Gly Pro Ile Asp
1               5                   10                  15

Thr Ala Asp Leu Gly Val Thr Leu Met His Glu His Val Phe Ile Met
            20                  25                  30

Thr Thr Glu Ile Ala Gln Asn Tyr Pro Glu Ala Trp Gly Asp Glu Asp
        35                  40                  45

Lys Arg Val Ala Gly Ala Ile Ala Arg Leu Gly Glu Leu Lys Ala Arg
    50                  55                  60

Gly Val Asp Thr Ile Val Asp Leu Thr Val Ile Gly Leu Gly Arg Tyr
65                  70                  75                  80

Ile Pro Arg Ile Ala Arg Val Ala Ala Ala Thr Glu Leu Asn Ile Val
                85                  90                  95

Val Ala Thr Gly Leu Tyr Thr Tyr Asn Asp Val Pro Phe Tyr Phe His
            100                 105                 110

Tyr Leu Gly Pro Gly Ala Gln Leu Asp Gly Pro Glu Ile Met Thr Asp
        115                 120                 125

Met Phe Val Arg Asp Ile Glu His Gly Ile Ala Asp Thr Gly Ile Lys
    130                 135                 140

Ala Gly Ile Leu Lys Cys Ala Thr Asp Glu Pro Gly Leu Thr Pro Gly
145                 150                 155                 160

Val Glu Arg Val Leu Arg Ala Val Ala Gln Ala Tyr Lys Arg Thr Gly
                165                 170                 175

Ala Pro Ile Ser Thr His Thr His Ala Gly Leu Arg Arg Gly Leu Asp
            180                 185                 190

Gln Gln Arg Ile Phe Ala Glu Glu Gly Val Asp Leu Ser Arg Val Val
        195                 200                 205

Ile Gly His Cys Gly Asp Ser Thr Asp Val Gly Tyr Leu Glu Glu Leu
    210                 215                 220

Ile Ala Ala Gly Ser Tyr Leu Gly Met Asp Arg Phe Gly Val Asp Val
225                 230                 235                 240

Ile Ser Pro Phe Gln Asp Arg Val Asn Ile Val Ala Arg Met Cys Glu
                245                 250                 255

Arg Gly His Ala Asp Lys Met Val Leu Ser His Asp Ala Cys Cys Tyr
            260                 265                 270

Phe Asp Ala Leu Pro Glu Glu Leu Val Pro Val Ala Met Pro Asn Trp
        275                 280                 285

His Tyr Leu His Ile His Asn Asp Val Ile Pro Ala Leu Lys Gln His
    290                 295                 300

Gly Val Thr Asp Glu Gln Leu His Thr Met Leu Val Asp Asn Pro Arg
305                 310                 315                 320

Arg Ile Phe Glu Arg Gln Gly Gly Tyr Gln
                325                 330
```

<210> SEQ ID NO 4
<211> LENGTH: 986
<212> TYPE: DNA
<213> ORGANISM: Mycobacterium tuberculosis

<400> SEQUENCE: 4

```
atgatttcag aattcccaga actaaatacc gctcgcggac ccatcgacac cgctgatctc      60
ggcgtcacgc tgatgcacga gcacgtcttc atcatgacca ccgagattgc gcagaactac     120
ccggaagcct ggggcgacga ggacaagcgg gtggccggcg ccatcgcccg gctagcgaac     180
```

-continued

```
tcaaggcccg cggcgtggac accatcgtcg acctcacggt gatcgggctg ggccgataca      240
tcccgcgcat cgcccgggtg gccgcggcca ccgagctgaa catcgtcgtg gccaccggct      300
tgtacaccta caacgacgtc ccgttctact tccactacct cgggccgggc gcacagctgg      360
acggcccgga gatcatgacc gacatgttcg tccgcgacat cgagcacggc atcgccgaca      420
ccggcatcaa ggcgggaatc ctcaagtgcg ccaccgacga acccggcctc accectggtg      480 tcgagcgggt gttgcgcgcg tcgcccaag cacacaaacg caccgggcg ccgatctcca        540 cccacaccca cgccgggctg cggcgcggcc ttgaccagca acgcatcttc gccgaggagg      600
gggtggacct gagccgggtg gttatcggac actgcggcga cagcaccgac gtcggctacc      660
tggaagagct catcgccgcc ggctcctacc tcgggatgga ccggttcggc gtcgacgtga      720
tctcaccgtt tcaggaccgg gtgaacatcg tggcccgaat gtgcgagcgc ggccatgccg      780
acaagatggt gctatcacac gacgcctgct gctatttcga cgcgcttccc gaggagctgg      840
tgccggtggc gatgccgaat tggcattacc tccacatcca caacgacgtc atccccgcac      900
tgaagcagca cggcgtcacc gacgagcagc tgcacaccat gctcgtcgac aacccgcgcc      960
gcatcttcga gcggcagggc ggctat                                         986
```

```
<210> SEQ ID NO 5
<211> LENGTH: 987
<212> TYPE: DNA
<213> ORGANISM: Mycobacterium tuberculosis

<400> SEQUENCE: 5
atgatttcag aattcccaga actaaatacc gctcgcggac ccatcgacac cgctgatctc       60
ggcgtcacgc tgatgcacga gcacgtcttc atcatgacca ccgagattgc gcagaactac      120
ccggaagcct ggggcgacga ggacaagcgg gtggccggcg ccatcgcccg gctagtcgaa      180
ctcaaggccc gcggcgtgga caccatcgtc gacctcacgg tgatcgggct gggccgatac      240
atcccgcgca tcgcccgggt ggccgcggcc accgagctga acatcgtcgt ggccaccggc      300
ttgtacacct acaacgacgt cccgttctac ttccactacc tcgggccggg cgcacagctg      360
gacggcccgg agatcatgac cgacatgttc gtccgcgaca tcgagcacgg catcgccgac      420
accggcatca aggcgggaat cctcaagtgc gccaccgacg aacccggcct caccectggt      480 gtcgagcggg tgttgcgcgc ggtcgcccaa gcacacaaac gcaccggggc gccgatctcc      540
acccacaccc acgccgggct gcggcgcggc cttgaccagc aacgcatctt cgccgaggag      600
ggggtggacc tgagccgggt ggttatcgga cactgcggcg acagcaccga cgtcggctac      660
ctggaagagc tcatcgccgc cggctcctac ctcgggatgg accggttcgg cgtcgacgtg      720
atctcaccgt ttcaggaccg ggtgaacatc gtggcccgaa tgtgcgagcg cggccatgcc      780
gacaagatgg tgctatcaca cgacgcctgc tgctatttcg acgcgcttcc cgaggagctg      840
gtgccggtgg cgatgccgaa ttggcattac ctccacatcc acaacgacgt catccccgca      900
ctgaagcagc acggcgtcac cgacgagcag ctgcacacca tgctcgtcga acccgcgc       960 cgcatcttcg agcggcaggg cggctat                                        987
```

```
<210> SEQ ID NO 6
<211> LENGTH: 990
<212> TYPE: DNA
<213> ORGANISM: Mycobacterium tuberculosis
```

-continued

<400> SEQUENCE: 6

```
atgatttcag aattcccaga actaaatacc gctcgcggac ccatcgacac cgctgatctc      60
ggcgtcacgc tgatgcacga gcacgtcttc atcatgacca ccgagattgc gcagaactac     120
ccggaagcct ggggcgacga ggacaagcgg gtggccggcg ccatcgcccg gctagtcgaa     180
ctcaaggccc gcggcgtgga caccatcgtc gacctcacgg tgatcgggct gggccgatac     240
atcccgcgca tcgcccgggt ggccgcggcc accgagctga acatcgtcgt ggccaccggc     300
ttgtacacct acaacgacgt cccgttctac ttccactacc tcgggccggg cgcacagctg     360
gacggcccgg agatcatgac cgacatgttc gtccgcgaca tcgagcacgg catcgccgac     420
accggcatca aggcgggaat cctcaagtgc gccaccgacg aacccggcct cacccctggt     480
gtcgagcggg tgttgcgcgc ggtcgcccaa gcatacaaac gcaccggggc gccgatctcc     540
acccacaccc acgccgggct gcggcgcggc cttgaccagc aacgcatctt cgccgaggag     600
ggggtggacc tgagccgggt ggttatcgga cactgcggcg acagcaccga cgtcggctac     660
ctggaagagc tcatcgccgc cggctcctac ctcgggatgg accggttcgg cgtcgacgtg     720
atctcaccgt ttcaggaccg ggtgaacatc gtggcccgaa tgtgcgagcg cggccatgcc     780
gacaagatgg tgctatcaca cgacgcctgc tgctatttcg acgcgcttcc cgaggagctg     840
gtgccggtgg cgatgccgaa ttggcattac ctccacatcc acaacgacgt catccccgca     900
ctgaagcagc acggcgtcac cgacgagcag ctgcacacca tgctcgtcga caacccgcgc     960
cgcatcttcg agcggcaggg cggctatcag                                     990
```

<210> SEQ ID NO 7
<211> LENGTH: 993
<212> TYPE: DNA
<213> ORGANISM: Artificial Sequence
<220> FEATURE:
<223> OTHER INFORMATION: synthetic

<400> SEQUENCE: 7

```
atgatttcag aattccctga actgaacacc gcgcgtggtc cgatcgacac cgcggacctg      60
ggcgttaccc tgatgcacga acacgttttc atcatgacca ccgaaatcgc tcagaactac     120
ccggaagcgt ggggtgacga agataaacgt gttgcgggtg caatcgctcg tctgggtgaa     180
ctgaaagctc gtggcgttga caccatcgtt gacctgaccg ttatcggtct gggtcgttac     240
atcccgcgta tcgctcgtgt tgcggctgct accgaactga acatcgttgt tgctaccggc     300
ctgtacacct acaacgatgt tccgttctac ttccactacc tgggtccggg tgcgcagctg     360
gacggcccgg aaatcatgac cgacatgttc gttcgtgaca tcgaacacgg tatcgcggat     420
accggtatca aagctggcat cctgaaatgc gcgaccgacg aacccgggtct gactccgggt     480 gttaacgtt ttctgcgtgc ggttgcacag gcgcacaaac gtaccggtgc gccgatcagc     540
acccacaccc acgcgggtct gcgtcgtggt ctggatcagc agcgtatctt cgctgaagaa     600
ggcgttgacc tgtcccgtgt tgttatcggt cactgcggtg attctaccga cgttggctac     660
ctggaagaac tgatcgcggc aggttcttac ctgggtatgg atcgtttcgg tgttgacgtt     720
atctccccgt tccaggatcg tgtgaacatc gttgcgcgca tgtgcgaacg tggtcacgcg     780
gacaaaatgg ttctgtctca cgacgcgtgc tgttacttcg atgctctgcc ggaagaactg     840
```

-continued

```
gttccggttg ctatgccgaa ctggcactac ctgcacatcc acaacgacgt tatcccagcg      900
ctgaaacagc acggtgttac cgacgaacag ctgcacacca tgctggttga caacccgcgt      960
cgtatcttcg aacgtcaggg tggttaccag taa                                   993
```

```
<210> SEQ ID NO 8
<211> LENGTH: 996
<212> TYPE: DNA
<213> ORGANISM: Artificial Sequence
<220> FEATURE:
<223> OTHER INFORMATION: synthetic

<400> SEQUENCE: 8
atgatttcag aattccctga actgaacacc gcgcgtggtc cgatcgacac cgcggacctg       60
ggcgttaccc tgatgcacga acacgttttc atcatgacca ccgaaatcgc tcagaactac      120
ccggaagcgt ggggtgacga agataaacgt gttgcgggtg caatcgctcg tctggttgaa      180
ctgaaagctc gtggcgttga caccatcgtt gacctgaccg ttatcggtct gggtcgttac      240
atcccgcgta tcgctcgtgt tgcggctgct accgaactga acatcgttgt tgctaccggc      300
ctgtacacct acaacgatgt tccgttctac ttccactacc tgggtccggg tgcgcagctg      360
gacggcccgg aaatcatgac cgacatgttc gttcgtgaca tcgaacacgg tatcgcggat      420
accggtatca aagctggcat cctgaaatgc gcgaccgacg aaccgggtct gactccgggt      480
gttgaacgtg ttctgcgtgc ggttgcacag gcgcacaaac gtaccggtgc gccgatcagc      540
acccacaccc acgcgggtct gcgtcgtggt ctggatcagc agcgtatctt cgctgaagaa      600
ggcgttgacc tgtcccgtgt tgttatcggt cactgcggtg attctaccga cgttggctac      660
ctggaagaac tgatcgcggc aggttcttac ctgggtatgg atcgtttcgg tgttgacgtt      720
atctccccgt tccaggatcg tgtgaacatc gttgcgcgca tgtgcgaacg tggtcacgcg      780
gacaaaatgg ttctgtctca cgacgcgtgc tgttacttcg atgctctgcc ggaagaactg      840
gttccggttg ctatgccgaa ctggcactac ctgcacatcc acaacgacgt tatcccagcg      900
ctgaaacagc acggtgttac cgacgaacag ctgcacacca tgctggttga caacccgcgt      960
cgtatcttcg aacgtcaggg tggttaccag taataa                               996
```

```
<210> SEQ ID NO 9
<211> LENGTH: 993
<212> TYPE: DNA
<213> ORGANISM: Artificial Sequence
<220> FEATURE:
<223> OTHER INFORMATION: synthetic

<400> SEQUENCE: 9
atgatttcag aattccctga actgaacacc gcgcgtggtc cgatcgacac cgcggacctg       60
ggcgttaccc tgatgcacga acacgttttc atcatgacca ccgaaatcgc tcagaactac      120
ccggaagcgt ggggtgacga agataaacgt gttgcgggtg caatcgctcg tctgggtgaa      180
ctgaaagctc gtggcgttga caccatcgtt gacctgaccg ttatcggtct gggtcgttac      240
atcccgcgta tcgctcgtgt tgcggctgct accgaactga acatcgttgt tgctaccggc      300
ctgtacacct acaacgatgt tccgttctac ttccactacc tgggtccggg tgcgcagctg      360
gacggcccgg aaatcatgac cgacatgttc gttcgtgaca tcgaacacgg tatcgcggat      420
accggtatca aagctggcat cctgaaatgc gcgaccgacg aaccgggtct gactccgggt      480
gttgaacgtg ttctgcgtgc ggttgcacag gcgtacaaac gtaccggtgc gccgatcagc      540
```

```
acccacaccc acgcgggtct gcgtcgtggt ctggatcagc agcgtatctt cgctgaagaa       600
ggcgttgacc tgtcccgtgt tgttatcggt cactgcggtg attctaccga cgttggctac       660
ctggaagaac tgatcgcggc aggttcttac ctgggtatgg atcgtttcgg tgttgacgtt       720
atctccccgt tccaggatcg tgtgaacatc gttgcgcgca tgtgcgaacg tggtcacgcg       780
gacaaaatgg ttctgtctca cgacgcgtgc tgttacttcg atgctctgcc ggaagaactg       840
gttccggttg ctatgccgaa ctggcactac ctgcacatcc acaacgacgt tatcccagcg       900
ctgaaacagc acggtgttac cgacgaacag ctgcacacca tgctggttga caacccgcgt       960
cgtatcttcg aacgtcaggg tggttaccag taa                                    993
```

```
<210> SEQ ID NO 10
<211> LENGTH: 716
<212> TYPE: PRT
<213> ORGANISM: Artificial Sequence
<220> FEATURE:
<223> OTHER INFORMATION: synthetic

<400> SEQUENCE: 10

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285
```

-continued

```
Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
    370                 375                 380

Glu Gly Arg Ile Ser Glu Phe Pro Glu Leu Asn Thr Ala Arg Gly Pro
385                 390                 395                 400

Ile Asp Thr Ala Asp Leu Gly Val Thr Leu Met His Glu His Val Phe
                405                 410                 415

Ile Met Thr Thr Glu Ile Ala Gln Asn Tyr Pro Glu Ala Trp Gly Asp
                420                 425                 430

Glu Asp Lys Arg Val Ala Gly Ala Ile Ala Arg Leu Gly Glu Leu Lys
            435                 440                 445

Ala Arg Gly Val Asp Thr Ile Val Asp Leu Thr Val Ile Gly Leu Gly
    450                 455                 460

Arg Tyr Ile Pro Arg Ile Ala Arg Val Ala Ala Ala Thr Glu Leu Asn
465                 470                 475                 480

Ile Val Val Ala Thr Gly Leu Tyr Thr Tyr Asn Asp Val Pro Phe Tyr
                485                 490                 495

Phe His Tyr Leu Gly Pro Gly Ala Gln Leu Asp Gly Pro Glu Ile Met
            500                 505                 510

Thr Asp Met Phe Val Arg Asp Ile Glu His Gly Ile Ala Asp Thr Gly
            515                 520                 525

Ile Lys Ala Gly Ile Leu Lys Cys Ala Thr Asp Glu Pro Gly Leu Thr
    530                 535                 540

Pro Gly Val Glu Arg Val Leu Arg Ala Val Ala Gln Ala His Lys Arg
545                 550                 555                 560

Thr Gly Ala Pro Ile Ser Thr His Thr His Ala Gly Leu Arg Arg Gly
            565                 570                 575

Leu Asp Gln Gln Arg Ile Phe Ala Glu Glu Gly Val Asp Leu Ser Arg
            580                 585                 590

Val Val Ile Gly His Cys Gly Asp Ser Thr Asp Val Gly Tyr Leu Glu
            595                 600                 605

Glu Leu Ile Ala Ala Gly Ser Tyr Leu Gly Met Asp Arg Phe Gly Val
    610                 615                 620

Asp Val Ile Ser Pro Phe Gln Asp Arg Val Asn Ile Val Ala Arg Met
625                 630                 635                 640

Cys Glu Arg Gly His Ala Asp Lys Met Val Leu Ser His Asp Ala Cys
            645                 650                 655

Cys Tyr Phe Asp Ala Leu Pro Glu Glu Leu Val Pro Val Ala Met Pro
            660                 665                 670

Asn Trp His Tyr Leu His Ile His Asn Asp Val Ile Pro Ala Leu Lys
            675                 680                 685

Gln His Gly Val Thr Asp Glu Gln Leu His Thr Met Leu Val Asp Asn
    690                 695                 700
```

-continued

```
Pro Arg Arg Ile Phe Glu Arg Gln Gly Gly Tyr Gln
705                 710                 715

<210> SEQ ID NO 11
<211> LENGTH: 716
<212> TYPE: PRT
<213> ORGANISM: Artificial Sequence
<220> FEATURE:
<223> OTHER INFORMATION: synthetic

<400> SEQUENCE: 11

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350
```

-continued

```
Ser Gly Arg Gln Thr Val Asp Glu Ala Leu Lys Asp Ala Gln Thr Asn
        355             360             365

Ser Ser Ser Asn Asn Asn Asn Asn Asn Asn Asn Asn Leu Gly Ile
    370             375             380

Glu Gly Arg Ile Ser Glu Phe Pro Glu Leu Asn Thr Ala Arg Gly Pro
385             390             395             400

Ile Asp Thr Ala Asp Leu Gly Val Thr Leu Met His Glu His Val Phe
            405             410             415

Ile Met Thr Thr Glu Ile Ala Gln Asn Tyr Pro Glu Ala Trp Gly Asp
            420             425             430

Glu Asp Lys Arg Val Ala Gly Ala Ile Ala Arg Leu Val Glu Leu Lys
            435             440             445

Ala Arg Gly Val Asp Thr Ile Val Asp Leu Thr Val Ile Gly Leu Gly
    450             455             460

Arg Tyr Ile Pro Arg Ile Ala Arg Val Ala Ala Ala Thr Glu Leu Asn
465             470             475             480

Ile Val Val Ala Thr Gly Leu Tyr Thr Tyr Asn Asp Val Pro Phe Tyr
            485             490             495

Phe His Tyr Leu Gly Pro Gly Ala Gln Leu Asp Gly Pro Glu Ile Met
            500             505             510

Thr Asp Met Phe Val Arg Asp Ile Glu His Gly Ile Ala Asp Thr Gly
            515             520             525

Ile Lys Ala Gly Ile Leu Lys Cys Ala Thr Asp Glu Pro Gly Leu Thr
    530             535             540

Pro Gly Val Glu Arg Val Leu Arg Ala Val Ala Gln Ala His Lys Arg
545             550             555             560

Thr Gly Ala Pro Ile Ser Thr His Thr His Ala Gly Leu Arg Arg Gly
            565             570             575

Leu Asp Gln Gln Arg Ile Phe Ala Glu Glu Gly Val Asp Leu Ser Arg
            580             585             590

Val Val Ile Gly His Cys Gly Asp Ser Thr Asp Val Gly Tyr Leu Glu
    595             600             605

Glu Leu Ile Ala Ala Gly Ser Tyr Leu Gly Met Asp Arg Phe Gly Val
    610             615             620

Asp Val Ile Ser Pro Phe Gln Asp Arg Val Asn Ile Val Ala Arg Met
625             630             635             640

Cys Glu Arg Gly His Ala Asp Lys Met Val Leu Ser His Asp Ala Cys
            645             650             655

Cys Tyr Phe Asp Ala Leu Pro Glu Glu Leu Val Pro Val Ala Met Pro
            660             665             670

Asn Trp His Tyr Leu His Ile His Asn Asp Val Ile Pro Ala Leu Lys
    675             680             685

Gln His Gly Val Thr Asp Glu Gln Leu His Thr Met Leu Val Asp Asn
    690             695             700

Pro Arg Arg Ile Phe Glu Arg Gln Gly Gly Tyr Gln
705             710             715
```

```
<210> SEQ ID NO 12
<211> LENGTH: 716
<212> TYPE: PRT
<213> ORGANISM: Artificial Sequence
<220> FEATURE:
<223> OTHER INFORMATION: synthetic
```

-continued

<400> SEQUENCE: 12

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Asn Leu Gly Ile
    370                 375                 380

Glu Gly Arg Ile Ser Glu Phe Pro Glu Leu Asn Thr Ala Arg Gly Pro
385                 390                 395                 400
```

-continued

```
Ile Asp Thr Ala Asp Leu Gly Val Thr Leu Met His Glu His Val Phe
            405                     410                 415

Ile Met Thr Thr Glu Ile Ala Gln Asn Tyr Pro Glu Ala Trp Gly Asp
            420                     425                 430

Glu Asp Lys Arg Val Ala Gly Ala Ile Ala Arg Leu Gly Glu Leu Lys
            435                     440                 445

Ala Arg Gly Val Asp Thr Ile Val Asp Leu Thr Val Ile Gly Leu Gly
            450                     455                 460

Arg Tyr Ile Pro Arg Ile Ala Arg Val Ala Ala Ala Thr Glu Leu Asn
465                     470                     475                 480

Ile Val Val Ala Thr Gly Leu Tyr Thr Tyr Asn Asp Val Pro Phe Tyr
            485                     490                 495

Phe His Tyr Leu Gly Pro Gly Ala Gln Leu Asp Gly Pro Glu Ile Met
            500                     505                 510

Thr Asp Met Phe Val Arg Asp Ile Glu His Gly Ile Ala Asp Thr Gly
            515                     520                 525

Ile Lys Ala Gly Ile Leu Lys Cys Ala Thr Asp Glu Pro Gly Leu Thr
            530                     535                 540

Pro Gly Val Glu Arg Val Leu Arg Ala Val Ala Gln Ala Tyr Lys Arg
545                     550                     555                 560

Thr Gly Ala Pro Ile Ser Thr His Thr His Ala Gly Leu Arg Arg Gly
            565                     570                 575

Leu Asp Gln Gln Arg Ile Phe Ala Glu Glu Gly Val Asp Leu Ser Arg
            580                     585                 590

Val Val Ile Gly His Cys Gly Asp Ser Thr Asp Val Gly Tyr Leu Glu
            595                     600                 605

Glu Leu Ile Ala Ala Gly Ser Tyr Leu Gly Met Asp Arg Phe Gly Val
            610                     615                 620

Asp Val Ile Ser Pro Phe Gln Asp Arg Val Asn Ile Val Ala Arg Met
625                     630                     635                 640

Cys Glu Arg Gly His Ala Asp Lys Met Val Leu Ser His Asp Ala Cys
            645                     650                 655

Cys Tyr Phe Asp Ala Leu Pro Glu Glu Leu Val Pro Val Ala Met Pro
            660                     665                 670

Asn Trp His Tyr Leu His Ile His Asn Asp Val Ile Pro Ala Leu Lys
            675                     680                 685

Gln His Gly Val Thr Asp Glu Gln Leu His Thr Met Leu Val Asp Asn
            690                     695                 700

Pro Arg Arg Ile Phe Glu Arg Gln Gly Gly Tyr Gln
705                     710                     715
```

```
<210> SEQ ID NO 13
<211> LENGTH: 2151
<212> TYPE: DNA
<213> ORGANISM: Artificial Sequence
<220> FEATURE:
<223> OTHER INFORMATION: synthetic

<400> SEQUENCE: 13
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
```

```
accccggaca aagcgttcca ggacaagctg tatccgttta cctgggatgc cgtacgttac      300
aacggcaagc tgattgctta cccgatcgct gttgaagcgt tatcgctgat ttataacaaa      360
gatctgctgc cgaacccgcc aaaaacctgg gaagagatcc cggcgctgga taaagaactg      420
aaagcgaaag gtaagagcgc gctgatgttc aacctgcaag aaccgtactt cacctggccg      480
ctgattgctg ctgacggggg ttatgcgttc aagtatgaaa acggcaagta cgacattaaa      540
gacgtgggcg tggataacgc tggcgcgaaa gcgggtctga ccttcctggt tgacctgatt      600
aaaaacaaac acatgaatgc agacaccgat tactccatcg cagaagctgc ctttaataaa      660
ggcgaaacag cgatgaccat caacggcccg tgggcatggt ccaacatcga caccagcaaa      720
gtgaattatg gtgtaacggt actgccgacc ttcaagggtc aaccatccaa accgttcgtt      780
ggcgtgctga gcgcaggtat taacgccgcc agtccgaaca aagagctggc aaaagagttc      840
ctcgaaaact atctgctgac tgatgaaggt ctggaagcgg ttaataaaga caaaccgctg      900
ggtgccgtag cgctgaagtc ttacgaggaa gagttggcga agatccacg tattgccgcc      960 actatggaaa acgcccagaa aggtgaaatc atgccgaaca tcccgcagat gtccgctttc     1020
tggtatgccg tgcgtactgc ggtgatcaac gccgccagcg gtcgtcagac tgtcgatgaa     1080
gccctgaaag acgcgcagac taattcgagc tcgaacaaca caacaataa caataacaac     1140 aacctcggga tcgagggaag gatttcagaa ttccctgaac tgaacaccgc gcgtggtccg     1200
atcgacaccg cggacctggg cgttaccctg atgcacgaac acgttttcat catgaccacc     1260
gaaatcgctc agaactaccc ggaagcgtgg ggtgacgaag ataaacgtgt tgcgggtgca     1320
atcgctcgtc tgggtgaact gaaagctcgt ggcgttgaca ccatcgttga cctgaccgtt     1380
atcggtctgg gtcgttacat cccgcgtatc gctcgtgttg cggctgctac cgaactgaac     1440
atcgttgttg ctaccggcct gtacacctac aacgatgttc cgttctactt ccactacctg     1500
ggtccgggtg cgcagctgga cggcccggaa atcatgaccg acatgttcgt tcgtgacatc     1560
gaacacggta tcgcggatac cggtatcaaa gctggcatcc tgaaatgcgc gaccgacgaa     1620
ccgggtctga ctccgggtgt tgaacgtgtt ctgcgtgcgg ttgcacaggc gcacaaacgt     1680
accggtgcgc cgatcagcac ccacacccac gcgggtctgc gtcgtggtct ggatcagcag     1740
cgtatcttcg ctgaagaagg cgttgacctg tcccgtgttg ttatcggtca ctgcggtgat     1800
tctaccgacg ttggctacct ggaagaactg atcgcggcag gttcttacct gggtatggat     1860
cgtttcggtg ttgacgttat ctccccgttc caggatcgtg tgaacatcgt tgcgcgcatg     1920
tgcgaacgtg gtcacgcgga caaaatggtt ctgtctcacg acgcgtgctg ttacttcgat     1980
gctctgccgg aagaactggt tccggttgct atgccgaact ggcactacct gcacatccac     2040
aacgacgtta tcccagcgct gaaacagcac ggtgttaccg acgaacagct gcacaccatg     2100
ctggttgaca acccgcgtcg tatcttcgaa cgtcagggtg gttaccagta a             2151
```

<210> SEQ ID NO 14
<211> LENGTH: 2154
<212> TYPE: DNA
<213> ORGANISM: Artificial Sequence
<220> FEATURE:
<223> OTHER INFORMATION: synthetic

<400> SEQUENCE: 14

```
atgaaaatcg aagaaggtaa actggtaatc tggattaacg gcgataaagg ctataacggt       60
ctcgctgaag tcggtaagaa attcgagaaa gataccggaa ttaaagtcac cgttgagcat      120
ccggataaac tggaagagaa attcccacag gttgcggcaa ctggcgatgg ccctgacatt      180
```

-continued

```
atcttctggg cacacgaccg ctttggtggc tacgctcaat ctggcctgtt ggctgaaatc    240
accccggaca aagcgttcca ggacaagctg tatccgttta cctgggatgc cgtacgttac    300
aacggcaagc tgattgctta cccgatcgct gttgaagcgt tatcgctgat ttataacaaa    360
gatctgctgc cgaacccgcc aaaaacctgg gaagagatcc cggcgctgga taaagaactg    420
aaagcgaaag gtaagagcgc gctgatgttc aacctgcaag aaccgtactt cacctggccg    480
ctgattgctg ctgacggggg ttatgcgttc aagtatgaaa acggcaagta cgacattaaa    540
gacgtgggcg tggataacgc tggcgcgaaa gcgggtctga ccttcctggt tgacctgatt    600
aaaaacaaac acatgaatgc agacaccgat tactccatcg cagaagctgc ctttaataaa    660
ggcgaaacag cgatgaccat caacggcccg tgggcatggt ccaacatcga caccagcaaa    720
gtgaattatg tgtaacggt actgccgacc ttcaagggtc aaccatccaa accgttcgtt    780
ggcgtgctga gcgcaggtat taacgccgcc agtccgaaca aagagctggc aaaagagttc    840
ctcgaaaact atctgctgac tgatgaaggt ctggaagcgg ttaataaaga caaaccgctg    900
ggtgccgtag cgctgaagtc ttacgaggaa gagttggcga aagatccacg tattgccgcc    960
actatggaaa acgcccagaa aggtgaaatc atgccgaaca tcccgcagat gtccgctttc   1020
tggtatgccg tgcgtactgc ggtgatcaac gccgccagcg gtcgtcagac tgtcgatgaa   1080
gccctgaaag acgcgcagac taattcgagc tcgaacaaca acaacaataa caataacaac   1140
aacctcggga tcgagggaag gatttcagaa ttccctgaac tgaacaccgc gcgtggtccg   1200
atcgacaccg cggacctggg cgttaccctg atgcacgaac acgttttcat catgaccacc   1260
gaaatcgctc agaactaccc ggaagcgtgg ggtgacgaag ataaacgtgt tgcgggtgca   1320
atcgctcgtc tggttgaact gaaagctcgt ggcgttgaca ccatcgttga cctgaccgtt   1380
atcggtctgg gtcgttacat cccgcgtatc gctcgtgttg cggctgctac cgaactgaac   1440
atcgttgttg ctaccggcct gtacacctac aacgatgttc cgttctactt ccactacctg   1500
ggtccgggtg cgcagctgga cggcccggaa atcatgaccg acatgttcgt tcgtgacatc   1560
gaacacggta tcgcggatac cggtatcaaa gctggcatcc tgaaatgcgc gaccgacgaa   1620
ccgggtctga ctccgggtgt tgaacgtgtt ctgcgtgcgg ttgcacaggc gcacaaacgt   1680
accggtgcgc cgatcagcac ccacacccac gcgggtctgc gtcgtggtct ggatcagcag   1740
cgtatcttcg ctgaagaagg cgttgacctg tcccgtgttg ttatcggtca ctgcggtgat   1800
tctaccgacg ttggctacct ggaagaactg atcgcggcag ttcttacct gggtatggat   1860 cgtttcggtg ttgacgttat ctccccgttc caggatcgtg tgaacatcgt tgcgcgcatg   1920
tgcgaacgtg gtcacgcgga caaaatggtt ctgtctcacg acgcgtgctg ttacttcgat   1980
gctctgccgg aagaactggt tccggttgct atgccgaact ggcactacct gcacatccac   2040
aacgacgtta tcccagcgct gaaacagcac ggtgttaccg acgaacagct gcacaccatg   2100
ctggttgaca acccgcgtcg tatcttcgaa cgtcagggtg gttaccagta ataa         2154
```

<210> SEQ ID NO 15
<211> LENGTH: 2151
<212> TYPE: DNA
<213> ORGANISM: Artificial Sequence
<220> FEATURE:
<223> OTHER INFORMATION: synthetic -continued

<400> SEQUENCE: 15

```
atgaaaatcg aagaaggtaa actggtaatc tggattaacg gcgataaagg ctataacggt      60
ctcgctgaag tcggtaagaa attcgagaaa gataccggaa ttaaagtcac cgttgagcat     120
ccggataaac tggaagagaa attcccacag gttgcggcaa ctggcgatgg ccctgacatt     180
atcttctggg cacacgaccg ctttggtggc tacgctcaat ctggcctgtt ggctgaaatc     240
accccggaca aagcgttcca ggacaagctg tatccgttta cctgggatgc cgtacgttac     300
aacggcaagc tgattgctta cccgatcgct gttgaagcgt tatcgctgat ttataacaaa     360
gatctgctgc cgaacccgcc aaaaacctgg aagagatcc cggcgctgga taaagaactg      420
aaagcgaaag gtaagagcgc gctgatgttc aacctgcaag aaccgtactt cacctggccg     480
ctgattgctg ctgacggggg ttatgcgttc aagtatgaaa acggcaagta cgacattaaa     540
gacgtgggcg tggataacgc tggcgcgaaa gcgggtctga ccttcctggt tgacctgatt     600
aaaaacaaac acatgaatgc agacaccgat tactccatcg cagaagctgc ctttaataaa     660
ggcgaaacag cgatgaccat caacggcccg tgggcatggt ccaacatcga caccagcaaa     720
gtgaattatg gtgtaacggt actgccgacc ttcaagggtc aaccatccaa accgttcgtt     780
ggcgtgctga gcgcaggtat taacgccgcc agtccgaaca aagagctggc aaaagagttc     840
ctcgaaaact atctgctgac tgatgaaggt ctggaagcgg ttaataaaga caaaccgctg     900
ggtgccgtag cgctgaagtc ttacgaggaa gagttggcga aagatccacg tattgccgcc     960
actatggaaa acgcccagaa aggtgaaatc atgccgaaca tcccgcagat gtccgctttc    1020
tggtatgccg tgcgtactgc ggtgatcaac gccgccagcg tcgtcagac tgtcgatgaa      1080 gccctgaaag acgcgcagac taattcgagc tcgaacaaca caacaataa caataacaac      1140 aacctcggga tcgagggaag gatttcagaa ttccctgaac tgaacaccgc gcgtggtccg    1200
atcgacaccg cggacctggg cgttaccctg atgcacgaac acgtttttcat catgaccacc    1260 gaaatcgctc agaactaccc ggaagcgtgg ggtgacgaag ataaacgtgt tgcgggtgca    1320
atcgctcgtc tgggtgaact gaaagctcgt ggcgttgaca ccatcgttga cctgaccgtt    1380
atcggtctgg gtcgttacat cccgcgtatc gctcgtgttg cggctgctac cgaactgaac    1440
atcgttgttg ctaccggcct gtacacctac aacgatgttc cgttctactt ccactacctg    1500
ggtccgggtg cgcagctgga cggcccggaa atcatgaccg acatgttcgt tcgtgacatc    1560
gaacacggta tcgcggatac cggtatcaaa gctggcatcc tgaaatgcgc gaccgacgaa    1620
ccgggtctga ctccgggtgt tgaacgtgtt ctgcgtgcgg ttgcacaggc gtacaaacgt    1680
accggtgcgc cgatcagcac ccacacccac gcgggtctgc gtcgtggtct ggatcagcag    1740
cgtatcttcg ctgaagaagg cgttgacctg tcccgtgttg ttatcggtca ctgcggtgat    1800
tctaccgacg ttggctacct ggaagaactg atcgcggcag ttcttacct gggtatggat     1860 cgtttcggtt ttgacgttat ctccccgttc caggatcgtg tgaacatcgt tgcgcgcatg    1920
tgcgaacgtg gtcacgcgga caaaatggtt ctgtctcacg acgcgtgctg ttacttcgat    1980
gctctgccgg aagaactggt tccggttgct atgccgaact ggcactacct gcacatccac    2040
aacgacgtta tcccagcgct gaaacagcac ggtgttaccg acgaacagct gcacaccatg    2100
ctggttgaca acccgcgtcg tatcttcgaa cgtcagggtg gttaccagta a            2151
```

<210> SEQ ID NO 16
<211> LENGTH: 415
<212> TYPE: PRT

<213> ORGANISM: Mycobacterium tuberculosis

<400> SEQUENCE: 16

```
Met Arg Ser Arg Pro Thr Lys Ser Arg Lys Ser Glu Tyr Gln Ile Arg
1               5                   10                  15

Ser Trp Ser Ser Cys Leu Ser Arg Ala Phe Pro Leu Asp Ser Lys Lys
            20                  25                  30

Ser Thr Val Ala Ala Met Ile Ser Pro Glu Arg Arg Ser Gly Tyr Leu
        35                  40                  45

Arg Val Lys Trp Leu Gly Leu Ser Ser Ile Arg Ile Gly Ser Arg Ala
    50                  55                  60

Val Arg Ser Thr Thr Arg Val Thr Leu Leu His Cys Gly Pro Ala Arg
65                  70                  75                  80

His Arg Leu Arg Pro Ser Ile Ser Asp Val Pro Glu Leu Asn Thr Ala
                85                  90                  95

Arg Gly Pro Ile Asp Thr Ala Asp Leu Gly Val Thr Leu Met His Glu
            100                 105                 110

His Val Phe Ile Met Thr Thr Glu Ile Ala Gln Asn Tyr Pro Glu Ala
            115                 120                 125

Trp Gly Asp Glu Asp Lys Arg Val Ala Gly Ala Ile Ala Arg Leu Gly
        130                 135                 140

Glu Leu Lys Ala Arg Gly Val Asp Thr Ile Val Asp Leu Thr Val Ile
145                 150                 155                 160

Gly Leu Gly Arg Tyr Ile Pro Arg Ile Ala Arg Val Ala Ala Ala Thr
                165                 170                 175

Glu Leu Asn Ile Val Val Ala Thr Gly Leu Tyr Thr Tyr Asn Asp Val
            180                 185                 190

Pro Phe Tyr Phe His Tyr Leu Gly Pro Gly Ala Gln Leu Asp Gly Pro
            195                 200                 205

Glu Ile Met Thr Asp Met Phe Val Arg Asp Ile Glu His Gly Ile Ala
        210                 215                 220

Asp Thr Gly Ile Lys Ala Gly Ile Leu Lys Cys Ala Thr Asp Glu Pro
225                 230                 235                 240

Gly Leu Thr Pro Gly Val Glu Arg Val Leu Arg Ala Val Ala Gln Ala
                245                 250                 255

His Lys Arg Thr Gly Ala Pro Ile Ser Thr His Thr His Ala Gly Leu
            260                 265                 270

Arg Arg Gly Leu Asp Gln Gln Arg Ile Phe Ala Glu Glu Gly Val Asp
        275                 280                 285

Leu Ser Arg Val Val Ile Gly His Cys Gly Asp Ser Thr Asp Val Gly
    290                 295                 300

Tyr Leu Glu Glu Leu Ile Ala Ala Gly Ser Tyr Leu Gly Met Asp Arg
305                 310                 315                 320

Phe Gly Val Asp Val Ile Ser Pro Phe Gln Asp Arg Val Asn Ile Val
            325                 330                 335

Ala Arg Met Cys Glu Arg Gly His Ala Asp Lys Met Val Leu Ser His
            340                 345                 350

Asp Ala Cys Cys Tyr Phe Asp Ala Leu Pro Glu Glu Leu Val Pro Val
            355                 360                 365

Ala Met Pro Asn Trp His Tyr Leu His Ile His Asn Asp Val Ile Pro
        370                 375                 380

Ala Leu Lys Gln His Gly Val Thr Asp Glu Gln Leu His Thr Met Leu
385                 390                 395                 400
```

-continued

```
Val Asp Asn Pro Arg Arg Ile Phe Glu Arg Gln Gly Gly Tyr Gln
                405             410             415

<210> SEQ ID NO 17
<211> LENGTH: 415
<212> TYPE: PRT
<213> ORGANISM: Mycobacterium tuberculosis

<400> SEQUENCE: 17

Met Arg Ser Arg Pro Thr Lys Ser Arg Lys Ser Glu Tyr Gln Ile Arg
1               5                   10                  15

Ser Trp Ser Ser Cys Leu Ser Arg Ala Phe Pro Leu Asp Ser Lys Lys
            20                  25                  30

Ser Thr Val Ala Ala Met Ile Ser Pro Glu Arg Arg Ser Gly Tyr Leu
        35                  40                  45

Arg Val Lys Trp Leu Gly Leu Ser Ser Ile Arg Ile Gly Ser Arg Ala
    50                  55                  60

Val Arg Ser Thr Thr Arg Val Thr Leu Leu His Cys Gly Pro Ala Arg
65                  70                  75                  80

His Arg Leu Arg Pro Ser Ile Ser Asp Val Pro Glu Leu Asn Thr Ala
                85                  90                  95

Arg Gly Pro Ile Asp Thr Ala Asp Leu Gly Val Thr Leu Met His Glu
            100                 105                 110

His Val Phe Ile Met Thr Thr Glu Ile Ala Gln Asn Tyr Pro Glu Ala
        115                 120                 125

Trp Gly Asp Glu Asp Lys Arg Val Ala Gly Ala Ile Ala Arg Leu Gly
        130                 135                 140

Glu Leu Lys Ala Arg Gly Val Asp Thr Ile Val Asp Leu Thr Val Ile
145                 150                 155                 160

Gly Leu Gly Arg Tyr Ile Pro Arg Ile Ala Arg Val Ala Ala Ala Thr
                165                 170                 175

Glu Leu Asn Ile Val Val Ala Thr Gly Leu Tyr Thr Tyr Asn Asp Val
            180                 185                 190

Pro Phe Tyr Phe His Tyr Leu Gly Pro Gly Ala Gln Leu Asp Gly Pro
        195                 200                 205

Glu Ile Met Thr Asp Met Phe Val Arg Asp Ile Glu His Gly Ile Ala
    210                 215                 220

Asp Thr Gly Ile Lys Ala Gly Ile Leu Lys Cys Ala Thr Asp Glu Pro
225                 230                 235                 240

Gly Leu Thr Pro Gly Val Glu Arg Val Leu Arg Ala Val Ala Gln Ala
                245                 250                 255

His Lys Arg Thr Gly Ala Pro Ile Ser Thr His Thr His Ala Gly Leu
            260                 265                 270

Arg Arg Gly Leu Asp Gln Gln Arg Ile Phe Ala Glu Glu Gly Val Glu
        275                 280                 285

Leu Ser Arg Val Val Ile Gly His Cys Gly Asp Ser Thr Asp Val Gly
    290                 295                 300

Tyr Leu Glu Glu Leu Ile Ala Ala Gly Ser Tyr Leu Gly Met Asp Arg
305                 310                 315                 320

Phe Gly Val Asp Val Ile Ser Pro Phe Gln Asp Arg Val Asn Ile Val
                325                 330                 335

Ala Arg Met Cys Glu Arg Gly His Ala Asp Lys Met Val Leu Ser His
            340                 345                 350

Asp Ala Cys Cys Tyr Phe Asp Ala Leu Pro Glu Glu Leu Val Pro Val
            355                 360                 365
```

```
Ala Met Pro Asn Trp His Tyr Leu His Ile His Asn Asp Val Ile Pro
    370             375             380

Ala Leu Lys Gln His Gly Val Thr Asp Glu Gln Leu His Thr Met Leu
385             390             395             400

Val Asp Asn Pro Arg Arg Ile Phe Glu Arg Gln Gly Gly Tyr Gln
            405             410             415

<210> SEQ ID NO 18
<211> LENGTH: 345
<212> TYPE: PRT
<213> ORGANISM: Mycobacterium tuberculosis

<400> SEQUENCE: 18

Met Thr Leu Leu His Cys Gly Pro Ala Arg His Arg Leu Arg Pro Ser
1               5               10              15

Ile Ser Asp Val Pro Glu Leu Asn Thr Ala Arg Gly Pro Ile Asp Thr
            20              25              30

Ala Asp Leu Gly Val Thr Leu Met His Glu His Val Phe Ile Met Thr
        35              40              45

Thr Glu Ile Ala Gln Asn Tyr Pro Glu Ala Trp Gly Asp Glu Asp Lys
    50              55              60

Arg Val Ala Gly Ala Ile Ala Arg Leu Gly Glu Leu Lys Ala Arg Gly
65              70              75              80

Val Asp Thr Ile Val Asp Leu Thr Val Ile Gly Leu Gly Arg Tyr Ile
            85              90              95

Pro Arg Ile Ala Arg Val Ala Ala Ala Thr Glu Leu Asn Ile Val Val
        100             105             110

Ala Thr Gly Leu Tyr Thr Tyr Asn Asp Val Pro Phe Tyr Phe His Tyr
        115             120             125

Leu Gly Pro Gly Ala Gln Leu Asp Gly Pro Glu Ile Met Thr Asp Met
    130             135             140

Phe Val Arg Asp Ile Glu His Gly Ile Ala Asp Thr Gly Ile Lys Ala
145             150             155             160

Gly Ile Leu Lys Cys Ala Thr Asp Glu Pro Gly Leu Thr Pro Gly Val
            165             170             175

Glu Arg Val Leu Arg Ala Val Ala Gln Ala His Lys Arg Thr Gly Ala
            180             185             190

Pro Ile Ser Thr His Thr His Ala Gly Leu Arg Arg Gly Leu Asp Gln
    195             200             205

Gln Arg Ile Phe Ala Glu Glu Gly Val Asp Leu Ser Arg Val Val Ile
    210             215             220

Gly His Cys Gly Asp Ser Thr Asp Val Gly Tyr Leu Glu Glu Leu Ile
225             230             235             240

Ala Ala Gly Ser Tyr Leu Gly Met Asp Arg Phe Gly Val Asp Val Ile
            245             250             255

Ser Pro Phe Gln Asp Arg Val Asn Ile Val Ala Arg Met Cys Glu Arg
            260             265             270

Gly His Ala Asp Lys Met Val Leu Ser His Asp Ala Cys Cys Tyr Phe
        275             280             285

Asp Ala Leu Pro Glu Glu Leu Val Pro Val Ala Met Pro Asn Trp His
    290             295             300

Tyr Leu His Ile His Asn Asp Val Ile Pro Ala Leu Lys Gln His Gly
305             310             315             320
```

-continued

```
Val Thr Asp Glu Gln Leu His Thr Met Leu Val Asp Asn Pro Arg Arg
            325                 330                 335

Ile Phe Glu Arg Gln Gly Gly Tyr Gln
            340                 345

<210> SEQ ID NO 19
<211> LENGTH: 326
<212> TYPE: PRT
<213> ORGANISM: Mycobacterium tuberculosis

<400> SEQUENCE: 19

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
            210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
            290                 295                 300

Glu Gln Leu His Thr Met Leu Val Asp Asn Pro Arg Arg Ile Phe Glu
305                 310                 315                 320

Arg Gln Gly Gly Tyr Gln
            325
```

```
<210> SEQ ID NO 20
<211> LENGTH: 326
<212> TYPE: PRT
<213> ORGANISM: Mycobacterium tuberculosis

<400> SEQUENCE: 20

Met Pro Gln Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 21
<211> LENGTH: 326
<212> TYPE: PRT
<213> ORGANISM: Mycobacterium tuberculosis
```

-continued

<400> SEQUENCE: 21

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Met Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

<210> SEQ ID NO 22
<211> LENGTH: 326
<212> TYPE: PRT
<213> ORGANISM: Mycobacterium tuberculosis

<400> SEQUENCE: 22

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30
```

```
Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Ala Ala Met Pro Asn Trp His Tyr Leu His
        275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

```
<210> SEQ ID NO 23
<211> LENGTH: 326
<212> TYPE: PRT
<213> ORGANISM: Mycobacterium tuberculosis

<400> SEQUENCE: 23
```

```
Met Pro Glu Leu Asn Thr Ala Arg Gly Pro Ile Asp Thr Ala Asp Leu
1                   5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60
```

```
Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Glu Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325
```

```
<210> SEQ ID NO 24
<211> LENGTH: 326
<212> TYPE: PRT
<213> ORGANISM: Mycobacterium tuberculosis

<400> SEQUENCE: 24
```

```
Met Pro Glu Leu Asn Thr Ala Arg Gly Pro Ile Asp Thr Ala Asp Leu
1                   5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95
```

```
Leu Phe Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
            210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 25
<211> LENGTH: 326
<212> TYPE: PRT
<213> ORGANISM: Mycobacterium tuberculosis

<400> SEQUENCE: 25

Met Pro Glu Leu Asn Thr Ala Arg Gly Pro Ile Asp Thr Ala Asp Leu
1                   5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125
```

```
Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
            195                 200                 205

Gly Asp Ser Thr Asp Ala Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 26
<211> LENGTH: 326
<212> TYPE: PRT
<213> ORGANISM: Mycobacterium tuberculosis

<400> SEQUENCE: 26

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Leu Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160
```

-continued

```
Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
            210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
            290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 27
<211> LENGTH: 326
<212> TYPE: PRT
<213> ORGANISM: Mycobacterium tuberculosis

<400> SEQUENCE: 27

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
            50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190
```

-continued

```
Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Ala Gly Tyr Gln
                325

<210> SEQ ID NO 28
<211> LENGTH: 326
<212> TYPE: PRT
<213> ORGANISM: Mycobacterium tuberculosis

<400> SEQUENCE: 28

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
        20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
        100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
        180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
        210                 215                 220
```

-continued

```
Ser Tyr Leu Gly Met Asp Gln Phe Gly Val Asp Val Ile Ser Pro Phe
225                 230                 235                 240

Gln Asp Arg Val Asn Ile Val Ala Arg Met Cys Glu Arg Gly His Ala
                    245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325
```

```
<210> SEQ ID NO 29
<211> LENGTH: 326
<212> TYPE: PRT
<213> ORGANISM: Mycobacterium tuberculosis

<400> SEQUENCE: 29

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Ala Asn Ile Val Ala Arg Met Cys Glu Arg Gly His Ala
                245                 250                 255
```

```
Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 30
<211> LENGTH: 326
<212> TYPE: PRT
<213> ORGANISM: Mycobacterium tuberculosis

<400> SEQUENCE: 30

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285
```

-continued

```
Ile His Asn Asp Val Ile Pro Ala Leu Lys Gln His Gly Val Thr Asn
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 31
<211> LENGTH: 326
<212> TYPE: PRT
<213> ORGANISM: Mycobacterium tuberculosis

<400> SEQUENCE: 31

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Thr Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300
```

```
Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 32
<211> LENGTH: 326
<212> TYPE: PRT
<213> ORGANISM: Mycobacterium tuberculosis

<400> SEQUENCE: 32

Met Pro Glu Leu Asn Thr Ala Arg Gly Pro Ile Asp Thr Ala Asp Leu
1               5                   10                  15

Gly Val Thr Leu Met His Glu His Val Phe Ile Met Ala Thr Glu Ile
                20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65              70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

```
<210> SEQ ID NO 33
<211> LENGTH: 326
<212> TYPE: PRT
<213> ORGANISM: Mycobacterium tuberculosis

<400> SEQUENCE: 33

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Ala Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 34
<211> LENGTH: 326
<212> TYPE: PRT
<213> ORGANISM: Mycobacterium tuberculosis
```

<400> SEQUENCE: 34

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Phe Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 35
<211> LENGTH: 326
<212> TYPE: PRT
<213> ORGANISM: Mycobacterium tuberculosis

<400> SEQUENCE: 35

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

```
Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

<210> SEQ ID NO 36
<211> LENGTH: 326
<212> TYPE: PRT
<213> ORGANISM: Mycobacterium tuberculosis

<400> SEQUENCE: 36

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60
```

```
Ile Val Asp Leu Thr Val Ile Gly Leu Gly Arg Tyr Ile Pro Arg Ile
65              70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu Gln
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

<210> SEQ ID NO 37
<211> LENGTH: 326
<212> TYPE: PRT
<213> ORGANISM: Mycobacterium tuberculosis

<400> SEQUENCE: 37

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
                35                  40                  45

Gly Ala Ile Ala Arg Leu Gly Glu Leu Lys Ala Arg Gly Val Asp Thr
    50                  55                  60

Ile Val Asp Leu Lys Val Ile Gly Leu Gly Arg Tyr Ile Pro Arg Ile
65              70                  75                  80

Ala Arg Val Ala Ala Ala Thr Glu Leu Asn Ile Val Val Ala Thr Gly
                85                  90                  95
```

```
Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 38
<211> LENGTH: 326
<212> TYPE: PRT
<213> ORGANISM: Mycobacterium tuberculosis

<400> SEQUENCE: 38

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125
```

-continued

```
Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
                195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Leu
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
                275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

```
<210> SEQ ID NO 39
<211> LENGTH: 326
<212> TYPE: PRT
<213> ORGANISM: Mycobacterium tuberculosis

<400> SEQUENCE: 39

Met Pro Glu Leu Asn Thr Ala Arg Gly Pro Ile Asp Thr Ala Asp Leu
1               5                   10                  15

Gly Val Thr Leu Met His Glu His Val Leu Ile Met Thr Thr Glu Ile
                20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160
```

```
Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 40
<211> LENGTH: 326
<212> TYPE: PRT
<213> ORGANISM: Mycobacterium tuberculosis

<400> SEQUENCE: 40

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Leu Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190
```

```
Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
                275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 41
<211> LENGTH: 326
<212> TYPE: PRT
<213> ORGANISM: Mycobacterium tuberculosis

<400> SEQUENCE: 41

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Lys Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
        210                 215                 220
```

```
Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 42
<211> LENGTH: 326
<212> TYPE: PRT
<213> ORGANISM: Mycobacterium tuberculosis

<400> SEQUENCE: 42

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr His Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255
```

-continued

```
Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 43
<211> LENGTH: 326
<212> TYPE: PRT
<213> ORGANISM: Mycobacterium tuberculosis

<400> SEQUENCE: 43

Met Pro Glu Leu Asn Thr Ala Arg Gly Pro Ile Asp Thr Ala Asp Leu
1               5                   10                  15

Gly Val Met Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270
```

-continued

```
Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 44
<211> LENGTH: 326
<212> TYPE: PRT
<213> ORGANISM: Mycobacterium tuberculosis

<400> SEQUENCE: 44

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
        275                 280                 285
```

-continued

```
Ile His Asn Asp Val Ile Pro Ala Leu Lys Gln His Gly Val Thr Asp
    290                 295                 300

Glu Gln Leu His Thr Met Leu Val Gly Asn Pro Arg Arg Ile Phe Glu
305                 310                 315                 320

Arg Gln Gly Gly Tyr Gln
                325

<210> SEQ ID NO 45
<211> LENGTH: 326
<212> TYPE: PRT
<213> ORGANISM: Mycobacterium tuberculosis

<400> SEQUENCE: 45

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln His Ile
            180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300
```

```
Glu Gln Leu His Thr Met Leu Val Asp Asn Pro Arg Arg Ile Phe Glu
305                 310             315             320

Arg Gln Gly Gly Tyr Gln
                325

<210> SEQ ID NO 46
<211> LENGTH: 326
<212> TYPE: PRT
<213> ORGANISM: Mycobacterium tuberculosis

<400> SEQUENCE: 46

Met Pro Glu Leu Asn Thr Ala Arg Gly Pro Ile Asp Thr Ala Asp Leu
1               5               10              15

Gly Val Thr Leu Met His Glu His Val Phe Ile Met Thr Thr Glu Ile
                20              25              30

Ala Gln Asn Tyr Pro Glu Ala Trp Gly Asp Glu Asp Lys Arg Val Ala
                35              40              45

Gly Ala Ile Ala Arg Leu Gly Glu Leu Lys Ala Arg Gly Val Asp Thr
        50              55              60

Ile Val Asp Leu Thr Val Ile Gly Leu Gly Arg Tyr Ile Pro Arg Ile
65              70              75              80

Ala Arg Val Ala Ala Ala Thr Glu Leu Asn Ile Val Val Ala Thr Gly
                85              90              95

Leu Tyr Thr Tyr Asn Asp Val Pro Phe Tyr Phe His Tyr Leu Gly Pro
                100             105             110

Gly Ala Gln Leu Asp Gly Pro Glu Ile Met Thr Asp Met Phe Val Arg
                115             120             125

Asp Ile Glu His Gly Ile Ala Asp Thr Gly Ile Lys Ala Gly Ile Leu
        130             135             140

Lys Cys Ala Thr Asp Glu Pro Gly Leu Thr Pro Gly Val Glu Arg Val
145             150             155             160

Leu Arg Ala Val Ala Gln Ala His Lys Arg Thr Gly Ala Pro Ile Ser
                165             170             175

Thr His Thr His Ala Gly Leu Arg Arg Gly Leu Asp Gln Gln Arg Ile
                180             185             190

Phe Ala Glu Glu Gly Val Asp Leu Ser Arg Val Val Ile Gly His Cys
                195             200             205

Gly Asp Ser Thr Asp Val Gly Tyr Leu Glu Glu Leu Ile Ala Ala Gly
        210             215             220

Ser Tyr Leu Gly Met Asp Arg Phe Gly Val Asp Val Ile Ser Pro Phe
225             230             235             240

Gln Asp Arg Val Asn Ile Val Ala Arg Met Cys Glu Arg Gly His Ala
                245             250             255

Asp Lys Met Val Leu Ser His Asp Ala Cys Cys Tyr Phe Asp Ala Leu
                260             265             270

Pro Glu Glu Leu Val Pro Val Ala Met Pro Asn Trp His Tyr Leu His
                275             280             285

Ile His Asn Asp Val Ile Pro Ala Leu Lys Gln His Gly Val Thr Asp
        290             295             300

Glu Gln Leu His Thr Met Leu Val Asp Asn Pro Arg Arg Ile Val Glu
305                 310             315             320

Arg Gln Gly Gly Tyr Gln
                325
```

<210> SEQ ID NO 47
<211> LENGTH: 326
<212> TYPE: PRT
<213> ORGANISM: Mycobacterium tuberculosis

<400> SEQUENCE: 47

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly Arg Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 48
<211> LENGTH: 326
<212> TYPE: PRT
<213> ORGANISM: Mycobacterium tuberculosis

<400> SEQUENCE: 48

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Arg Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

<210> SEQ ID NO 49
<211> LENGTH: 326
<212> TYPE: PRT
<213> ORGANISM: Mycobacterium tuberculosis

<400> SEQUENCE: 49

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30
```

-continued

---

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
    210                 215                 220

Ser Ser Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 50
<211> LENGTH: 326
<212> TYPE: PRT
<213> ORGANISM: Mycobacterium tuberculosis
<220> FEATURE:
<221> NAME/KEY: misc_feature
<222> LOCATION: (145)..(145)
<223> OTHER INFORMATION: Xaa can be any naturally occurring amino acid

<400> SEQUENCE: 50

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

-continued

```
Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Xaa Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 51
<211> LENGTH: 326
<212> TYPE: PRT
<213> ORGANISM: Mycobacterium tuberculosis

<400> SEQUENCE: 51

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95
```

```
Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Arg Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 52
<211> LENGTH: 326
<212> TYPE: PRT
<213> ORGANISM: Mycobacterium tuberculosis

<400> SEQUENCE: 52

Met Pro Glu Leu Asn Thr Ala Arg Arg Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125
```

```
Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
                195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
    275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 53
<211> LENGTH: 326
<212> TYPE: PRT
<213> ORGANISM: Mycobacterium tuberculosis

<400> SEQUENCE: 53

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
                35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
                115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175
```

```
Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
            210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
            290                 295                 300

Glu Gln Leu His Thr Met Leu Val Asp Asn Pro Arg Cys Ile Phe Glu
305                 310                 315                 320

Arg Gln Gly Gly Tyr Gln
            325

<210> SEQ ID NO 54
<211> LENGTH: 326
<212> TYPE: PRT
<213> ORGANISM: Mycobacterium tuberculosis

<400> SEQUENCE: 54

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Val Arg Gly Val Asp Thr
            50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Asp Gln Gln Arg Ile
            180                 185                 190
```

```
Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 55
<211> LENGTH: 326
<212> TYPE: PRT
<213> ORGANISM: Mycobacterium tuberculosis

<400> SEQUENCE: 55

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Lys Lys Val Pro Phe Tyr Phe His Tyr Leu Gly Pro
                100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
        195                 200                 205
```

```
Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
                275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325
```

```
<210> SEQ ID NO 56
<211> LENGTH: 326
<212> TYPE: PRT
<213> ORGANISM: Mycobacterium tuberculosis

<400> SEQUENCE: 56
```

```
Met Pro Glu Leu Asn Thr Ala Arg Gly Pro Ile Asp Thr Ala Asp Leu
1                   5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
                35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
                115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Val Ile Gly His Cys
                195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240
```

Gln Asp Arg Val Asn Ile Val Ala Arg Met Cys Glu Arg Gly His Ala
            245                 250                 255

Asp Lys Met Val Leu Ser His Asp Ala Cys Cys Cys Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
            290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 57
<211> LENGTH: 326
<212> TYPE: PRT
<213> ORGANISM: Mycobacterium tuberculosis

<400> SEQUENCE: 57

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
            35                  40                  45

Gly Ala Ile Ala Arg Leu Gly Glu Leu Lys Val Arg Gly Val Asp Thr
            50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Asp Leu Ser Arg Val Ile Ile Gly His Cys
            195                 200                 205

Gly Asp Ser Thr Asp Val Gly Tyr Leu Glu Glu Leu Ile Ala Ala Gly
            210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

-continued

```
Pro Glu Glu Leu Val Pro Val Ala Met Pro Asn Trp His Tyr Leu His
        275                 280             285

Ile His Asn Asp Val Ile Pro Ala Leu Lys Gln His Gly Val Thr Asp
    290                 295             300

Glu Gln Leu His Thr Met Leu Val Asp Asn Pro Arg Arg Ile Phe Glu
305                 310             315                 320

Arg Gln Gly Gly Tyr Gln
            325

<210> SEQ ID NO 58
<211> LENGTH: 326
<212> TYPE: PRT
<213> ORGANISM: Mycobacterium tuberculosis

<400> SEQUENCE: 58

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Cys Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
        165                 170                 175

Thr His Thr His Ala Gly Leu Arg Arg Gly Leu Asp Gln Gln Arg Ile
        180                 185                 190

Phe Ala Glu Glu Gly Val Glu Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
        245                 250                 255

Asp Lys Met Val Leu Ser His Asp Ala Cys Cys Tyr Phe Asp Ala Leu
        260                 265                 270

Pro Glu Glu Leu Val Pro Val Ala Met Pro Asn Trp His Tyr Leu His
        275                 280             285

Ile His Asn Asp Val Ile Pro Ala Leu Lys Gln His Gly Val Thr Asp
    290                 295             300
```

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 59
<211> LENGTH: 328
<212> TYPE: PRT
<213> ORGANISM: Mycobacterium tuberculosis

<400> SEQUENCE: 59

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
                35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
                115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
                180                 185                 190

Phe Ala Glu Glu Gly Val Glu Leu Ser Arg Val Val Ile Gly His Cys
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
                260                 265                 270

Pro Glu Glu Leu Val Pro Val Ala Met Pro Asn Trp His Tyr Leu His
        275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Ile
305                 310                 315                 320

Phe Glu Arg Gln Gly Gly Tyr Gln
                325

```
<210> SEQ ID NO 60
<211> LENGTH: 326
<212> TYPE: PRT
<213> ORGANISM: Mycobacterium tuberculosis

<400> SEQUENCE: 60

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Cys Asp Ala Leu
            260                 265                 270

Pro Gly Glu Leu Val Pro Val Ala Met Pro Asn Trp His Tyr Leu His
        275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 61
<211> LENGTH: 326
<212> TYPE: PRT
<213> ORGANISM: Mycobacterium tuberculosis
```

-continued

```
<400> SEQUENCE: 61

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr His Lys His Val Pro Phe Tyr Phe His Tyr Leu Gly Pro
            100                 105                 110

Gly Ala Gln Leu Asp Gly Pro Glu Ile Met Thr Asp Met Phe Val Arg
            115                 120                 125

Asp Ile Glu His Gly Ile Ala Asp Thr Gly Ile Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Val Ile Gly His Cys
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Gln
                325

<210> SEQ ID NO 62
<211> LENGTH: 328
<212> TYPE: PRT
<213> ORGANISM: Mycobacterium tuberculosis

<400> SEQUENCE: 62

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30
```

```
Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
                115                 120                 125

Asp Ile Glu His Gly Ile Ala Asp Thr Gly Ile Lys Ala Gly Ile Leu
            130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
                165                 170                 175

Thr His Thr His Ala Gly Leu Arg Arg Gly Leu Asp Gln Gln Arg Ile
            180                 185                 190

Phe Ala Lys Glu Gly Val Glu Leu Ser Arg Val Val Ile Gly His Cys
                195                 200                 205

Gly Asp Ser Thr Asp Val Gly Tyr Leu Glu Glu Leu Ile Ala Ala Gly
            210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Met Leu Val Asp Asn Pro Arg Arg Ile Phe Ile
305                 310                 315                 320

Phe Glu Arg Gln Gly Gly Tyr Gln
                325
```

```
<210> SEQ ID NO 63
<211> LENGTH: 326
<212> TYPE: PRT
<213> ORGANISM: Mycobacterium canettii

<400> SEQUENCE: 63
```

```
Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Val Arg Gly Val Asp Thr
    50                  55                  60
```

-continued

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Ser Phe His Tyr Leu Gly Pro
            100                 105                 110

Gly Ala Arg Leu Gly Gly Pro Glu Ile Met Thr Asp Met Phe Val Arg
            115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
            180                 185                 190

Phe Ala Glu Glu Gly Val Asp Leu Ser Arg Val Ile Ile Gly His Cys
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
                245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg His Gly Gly Tyr Gln
                325

<210> SEQ ID NO 64
<211> LENGTH: 326
<212> TYPE: PRT
<213> ORGANISM: Mycobacterium tuberculosis
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (82)..(84)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (183)..(185)
<223> OTHER INFORMATION: Xaa can be any naturally occurring amino acid
<220> FEATURE:
<221> NAME/KEY: misc_feature
<222> LOCATION: (196)..(196)
<223> OTHER INFORMATION: Xaa can be any naturally occurring amino acid
<220> FEATURE:
<221> NAME/KEY: misc_feature
<222> LOCATION: (212)..(212)
<223> OTHER INFORMATION: Xaa can be any naturally occurring amino acid
<220> FEATURE:
<221> NAME/KEY: misc_feature
<222> LOCATION: (310)..(310)
<223> OTHER INFORMATION: Xaa can be any naturally occurring amino acid

<400> SEQUENCE: 64

Met Pro Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
    50                  55                  60

Ile Val Asp Leu Thr Val Ile Gly Leu Gly Xaa Tyr Ile Pro Arg Ile
65                  70                  75                  80

Ala Xaa Xaa Xaa Ala Ala Thr Glu Leu Asn Ile Val Val Ala Thr Xaa
                85                  90                  95

Leu Tyr Thr Tyr Asn Asp Val Pro Phe Tyr Phe His Tyr Leu Gly Pro
            100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Ala Pro Ile Ser
            165                 170                 175

Thr His Thr His Ala Gly Xaa Xaa Xaa Gly Leu Asp Gln Gln Arg Ile
            180                 185                 190

Phe Ala Glu Xaa Gly Val Asp Leu Ser Arg Val Val Ile Gly His Cys
        195                 200                 205

Gly Asp Ser Xaa Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Gln Asp Arg Val Asn Ile Val Ala Arg Met Cys Glu Arg Gly His Ala
            245                 250                 255

Asp Lys Met Val Leu Ser His Asp Ala Cys Cys Tyr Phe Asp Ala Leu
            260                 265                 270

Pro Glu Glu Leu Val Pro Val Ala Met Pro Asn Trp His Tyr Leu His
            275                 280                 285

Ile His Asn Asp Val Ile Pro Ala Leu Lys Gln His Gly Val Thr Asp
    290                 295                 300

Glu Gln Leu His Thr Xaa Leu Val Asp Asn Pro Arg Arg Ile Phe Glu
305                 310                 315                 320

Arg Gln Gly Gly Tyr Gln
                325

<210> SEQ ID NO 65
<211> LENGTH: 306
<212> TYPE: PRT
<213> ORGANISM: Mycobacterium tuberculosis -continued

<400> SEQUENCE: 65

```
Met His Glu His Val Phe Ile Met Thr Thr Glu Ile Ala Gln Asn Tyr
1               5                   10                  15

Pro Glu Ala Trp Gly Asp Glu Asp Lys Arg Val Ala Gly Ala Ile Ala
            20                  25                  30

Arg Leu Gly Glu Leu Lys Ala Arg Gly Val Asp Thr Ile Val Asp Leu
        35                  40                  45

Thr Val Ile Gly Leu Gly Arg Tyr Ile Pro Arg Ile Ala Arg Val Ala
        50                  55                  60

Ala Ala Thr Glu Leu Asn Ile Val Val Ala Thr Gly Leu Tyr Thr Tyr
65                  70                  75                  80

Asn Asp Val Pro Phe Tyr Phe His Tyr Leu Gly Pro Gly Ala Gln Leu
                85                  90                  95

Asp Gly Pro Glu Ile Met Thr Asp Met Phe Val Arg Asp Ile Glu His
            100                 105                 110

Gly Ile Ala Asp Thr Gly Ile Lys Ala Gly Ile Leu Lys Cys Ala Thr
        115                 120                 125

Asp Glu Pro Gly Leu Thr Pro Gly Val Glu Arg Val Leu Arg Ala Val
        130                 135                 140

Ala Gln Ala His Lys Arg Thr Gly Ala Pro Ile Ser Thr His Thr His
145                 150                 155                 160

Ala Gly Leu Arg Arg Gly Leu Asp Gln Gln Arg Ile Phe Ala Glu Glu
                165                 170                 175

Gly Val Asp Leu Ser Arg Val Val Ile Gly His Cys Gly Asp Ser Thr
            180                 185                 190

Asp Val Gly Tyr Leu Glu Glu Leu Ile Ala Ala Gly Ser Tyr Leu Gly
        195                 200                 205

Met Asp Arg Phe Gly Val Asp Val Ile Ser Pro Phe Gln Asp Arg Val
    210                 215                 220

Asn Ile Val Ala Arg Met Cys Glu Arg Gly His Ala Asp Lys Met Val
225                 230                 235                 240

Leu Ser His Asp Ala Cys Cys Tyr Phe Asp Ala Leu Pro Glu Glu Leu
                245                 250                 255

Val Pro Val Ala Met Pro Asn Trp His Tyr Leu His Ile His Asn Asp
            260                 265                 270

Val Ile Pro Ala Leu Lys Gln His Gly Val Thr Asp Glu Gln Leu His
        275                 280                 285

Thr Met Leu Val Asp Asn Pro Arg Arg Ile Phe Glu Arg Gln Gly Gly
    290                 295                 300

Tyr Gln
305
```

<210> SEQ ID NO 66
<211> LENGTH: 313
<212> TYPE: PRT
<213> ORGANISM: Mycobacterium tuberculosis

<400> SEQUENCE: 66

```
Met Val Gly Asp Arg Asp Arg Val Leu Glu His Val Phe Ile Met Thr
1               5                   10                  15

Thr Glu Ile Ala Gln Asn Tyr Pro Glu Ala Trp Gly Asp Glu Asp Lys
            20                  25                  30

Arg Val Ala Gly Ala Ile Ala Arg Leu Gly Glu Leu Lys Ala Arg Gly
        35                  40                  45
```

```
Val Asp Thr Ile Val Asp Leu Thr Val Ile Gly Leu Gly Arg Tyr Ile
    50              55              60

Pro Arg Ile Ala Arg Val Ala Ala Ala Thr Glu Leu Asn Ile Val Val
65              70              75              80

Ala Thr Gly Leu Tyr Thr Tyr Asn Asp Val Pro Phe Tyr Phe His Tyr
                85              90              95

Leu Gly Pro Gly Ala Gln Leu Asp Gly Pro Glu Ile Met Thr Asp Met
            100             105             110

Phe Val Arg Asp Ile Glu His Gly Ile Ala Asp Thr Gly Ile Lys Ala
            115             120             125

Gly Ile Leu Lys Cys Ala Thr Asp Glu Pro Gly Leu Thr Pro Gly Val
    130             135             140

Glu Arg Val Leu Arg Ala Val Ala Gln Ala His Lys Arg Thr Gly Ala
145             150             155             160

Pro Ile Ser Thr His Thr His Ala Gly Leu Arg Arg Gly Leu Asp Gln
            165             170             175

Gln Arg Ile Phe Ala Glu Glu Gly Val Asp Leu Ser Arg Val Val Ile
            180             185             190

Gly His Cys Gly Asp Ser Thr Asp Val Gly Tyr Leu Glu Glu Leu Ile
            195             200             205

Ala Ala Gly Ser Tyr Leu Gly Met Asp Arg Phe Gly Val Asp Val Ile
    210             215             220

Ser Pro Phe Gln Asp Arg Val Asn Ile Val Ala Arg Met Cys Glu Arg
225             230             235             240

Gly His Ala Asp Lys Met Val Leu Ser His Asp Ala Cys Cys Tyr Phe
            245             250             255

Asp Ala Leu Pro Glu Glu Leu Val Pro Val Ala Met Pro Asn Trp His
            260             265             270

Tyr Leu His Ile His Asn Asp Val Ile Pro Ala Leu Lys Gln His Gly
            275             280             285

Val Thr Asp Glu Gln Leu His Thr Met Leu Val Asp Asn Pro Arg Arg
    290             295             300

Ile Phe Glu Arg Gln Gly Gly Tyr Gln
305             310

<210> SEQ ID NO 67
<211> LENGTH: 325
<212> TYPE: PRT
<213> ORGANISM: Mycobacterium lacus

<400> SEQUENCE: 67

Met Pro Val Leu Asn Thr Ala Arg Gly Pro Ile Asp Thr Ala Asp Leu
1               5               10              15

Gly Val Thr Leu Met His Glu His Val Phe Ile Met Thr Thr Glu Ile
            20              25              30

Ala Gln Asn Tyr Pro Glu Ala Trp Gly Asp Glu Glu Arg Arg Val Ala
        35              40              45

Asp Ala Ile Thr Arg Leu Gly Glu Leu Lys Ala Arg Gly Val Asp Thr
    50              55              60

Ile Val Asp Leu Thr Val Ile Gly Leu Gly Arg Tyr Ile Pro Arg Ile
65              70              75              80

Ala Arg Val Ala Ser Ala Thr Glu Leu Asn Ile Val Val Ala Thr Gly
            85              90              95
```

-continued

```
Leu Tyr Thr Tyr Asn Asp Val Pro Phe Tyr Phe His Tyr Leu Gly Pro
            100                 105                 110

Gly Gly Met Leu Asp Gly Pro Glu Ile Met Thr Asp Met Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Val Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Ala Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Asn Gly
    210                 215                 220

Ser Tyr Leu Gly Met Asp Arg Phe Gly Ile Asp Val Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Val Ala Val Ala Ala Pro Asn Trp His Tyr Leu His
            275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr
                325

<210> SEQ ID NO 68
<211> LENGTH: 326
<212> TYPE: PRT
<213> ORGANISM: Mycobacterium avium

<400> SEQUENCE: 68

Met Ser Glu Leu Asn Thr Ala Arg Gly Pro Ile Asp Thr Ala Ala Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Gln Arg Val Ala
            35                  40                  45

Asp Ala Ile Asp Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
            100                 105                 110

Gly Ala Glu Leu Gly Gly Pro Glu Ile Met Thr Asp Met Phe Val Arg
            115                 120                 125
```

-continued

```
Asp Ile Glu Gln Gly Ile Ala Asp Thr Gly Ile Lys Ala Gly Ile Leu
    130             135             140

Lys Cys Ala Thr Asp Ala Pro Gly Val Thr Pro Gly Val Glu Arg Val
145             150             155             160

Leu Arg Ala Val Ala Gln Ala His Lys Arg Thr Gly Val Pro Ile Ser
                165             170             175

Thr His Thr His Ala Gly Leu Arg Arg Gly Leu Asp Gln Gln Arg Ile
            180             185             190

Phe Glu Glu Glu Gly Val Asp Leu Ser Arg Val Val Ile Gly His Ser
            195             200             205

Gly Asp Ser Thr Asp Val Gly Tyr Leu Glu Glu Leu Ile Ala Ala Gly
    210             215             220

Ser Tyr Leu Gly Met Asp Arg Phe Gly Ile Asp Ala Ile Ser Pro Phe
225             230             235             240

Glu Asp Arg Val Asn Ile Val Ala Gln Met Cys Glu Arg Gly His Ala
            245             250             255

Asp Lys Met Val Leu Ser His Asp Ala Asn Cys Tyr Phe Asp Ala Leu
            260             265             270

Pro Glu Glu Leu Val Pro Gln Val Met Pro Asn Trp His Tyr Leu His
            275             280             285

Ile His Asn Asp Val Ile Pro Ala Leu Lys Gln Arg Gly Val Thr Asp
    290             295             300

Glu Gln Leu His Thr Met Leu Val Asp Asn Pro Arg Arg Ile Phe Glu
305             310             315             320

Arg Gln Gly Pro Tyr Gly
            325
```

```
<210> SEQ ID NO 69
<211> LENGTH: 299
<212> TYPE: PRT
<213> ORGANISM: Mycobacterium tuberculosis

<400> SEQUENCE: 69

Met Thr Thr Glu Ile Ala Gln Asn Tyr Pro Glu Ala Trp Gly Asp Glu
1               5               10              15

Asp Lys Arg Val Ala Gly Ala Ile Ala Arg Leu Gly Glu Leu Lys Ala
            20              25              30

Arg Gly Val Asp Thr Ile Val Asp Leu Thr Val Ile Gly Leu Gly Arg
            35              40              45

Tyr Ile Pro Arg Ile Ala Arg Val Ala Ala Ala Thr Glu Leu Asn Ile
    50              55              60

Val Val Ala Thr Gly Leu Tyr Thr Tyr Asn Asp Val Pro Phe Tyr Phe
65              70              75              80

His Tyr Leu Gly Pro Gly Ala Gln Leu Asp Gly Pro Glu Ile Met Thr
                85              90              95

Asp Met Phe Val Arg Asp Ile Glu His Gly Ile Ala Asp Thr Gly Ile
            100             105             110

Lys Ala Gly Ile Leu Lys Cys Ala Thr Asp Glu Pro Gly Leu Thr Pro
            115             120             125

Gly Val Glu Arg Val Leu Arg Ala Val Ala Gln Ala His Lys Arg Thr
    130             135             140

Gly Ala Pro Ile Ser Thr His Thr His Ala Gly Leu Arg Arg Gly Leu
145             150             155             160
```

```
Asp Gln Gln Arg Ile Phe Ala Glu Glu Gly Val Asp Leu Ser Arg Val
            165                 170                 175

Val Ile Gly His Cys Gly Asp Ser Thr Asp Val Gly Tyr Leu Glu Glu
            180                 185                 190

Leu Ile Ala Ala Gly Ser Tyr Leu Gly Met Asp Arg Phe Gly Val Asp
            195                 200                 205

Val Ile Ser Pro Phe Gln Asp Arg Val Asn Ile Val Ala Arg Met Cys
            210                 215                 220

Glu Arg Gly His Ala Asp Lys Met Val Leu Ser His Asp Ala Cys Cys
225                 230                 235                 240

Tyr Phe Asp Ala Leu Pro Glu Glu Leu Val Pro Val Ala Met Pro Asn
            245                 250                 255

Trp His Tyr Leu His Ile His Asn Asp Val Ile Pro Ala Leu Lys Gln
            260                 265                 270

His Gly Val Thr Asp Glu Gln Leu His Thr Met Leu Val Asp Asn Pro
            275                 280                 285

Arg Arg Ile Phe Glu Arg Gln Gly Gly Tyr Gln
    290                 295

<210> SEQ ID NO 70
<211> LENGTH: 326
<212> TYPE: PRT
<213> ORGANISM: Mycobacterium haemophilum

<400> SEQUENCE: 70

Met Ser Glu Leu Asn Thr Ala Arg Gly Pro Ile Ser Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Gln Arg Val Ala
            35                  40                  45

Asp Ala Ile Ala Arg Leu Ser Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Leu Tyr Thr Tyr Asn Asp Val Pro Phe Tyr Phe His Tyr Leu Gly Pro
            100                 105                 110

Gly Ala Pro Leu Asn Gly Pro Glu Ile Met Thr Asp Met Phe Val Arg
            115                 120                 125

Asp Ile Glu Gln Gly Val Ala Asp Thr Gly Ile Lys Ala Gly Ile Leu
            130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Ala Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Asn Gly
            210                 215                 220
```

```
Ser Tyr Leu Gly Met Asp Arg Phe Gly Val Asp Val Ile Leu Pro Phe
225             230             235             240

Glu Asp Arg Val Ser Ile Val Ala Gln Met Cys Glu Arg Gly His Ala
            245             250             255

Asp Lys Met Val Leu Ser His Asp Ala Asn Cys Tyr Phe Asp Ala Leu
        260             265             270

Pro Glu Ala Leu Gln Pro Val Ala Ala Pro Asn Trp His Tyr Leu His
    275             280             285

Ile His Asn Asp Val Ile Pro Ala Leu Lys Glu Arg Gly Val Thr Asp
    290             295             300

Glu Gln Leu His Thr Met Leu Val Asp Asn Pro Arg Arg Ile Phe Glu
305             310             315             320

Arg Gln Gly Thr Tyr Glu
                325

<210> SEQ ID NO 71
<211> LENGTH: 326
<212> TYPE: PRT
<213> ORGANISM: Mycobacterium sp.

<400> SEQUENCE: 71

Met Ser Glu Leu Asn Thr Ala Arg Gly Pro Ile Asp Thr Ala Asp Leu
1               5               10              15

Gly Val Thr Leu Met His Glu His Val Phe Ile Met Thr Thr Glu Val
            20              25              30

Val Gln Asn Tyr Pro Glu Ala Trp Gly Asp Glu Asp Lys Arg Val Ala
        35              40              45

Asp Ala Val Ala Arg Leu Asn Glu Leu Lys Ser Arg Gly Val Asp Thr
    50              55              60

Ile Val Asp Leu Thr Val Ile Gly Leu Gly Arg Tyr Ile Pro Arg Ile
65              70              75              80

Ala Arg Val Ala Ala Gln Thr Glu Leu Asn Ile Val Val Ala Thr Gly
            85              90              95

Leu Tyr Thr Tyr Asn Asp Val Pro Phe Cys Phe His Tyr Leu Gly Pro
            100             105             110

Gly Thr Gln Leu Asp Gly Pro Glu Thr Met Thr Asp Leu Phe Val Arg
        115             120             125

Asp Ile Glu Gln Gly Ile Ala Asp Thr Gly Ile Lys Ala Gly Ile Leu
    130             135             140

Lys Cys Ala Thr Asp Glu Pro Gly Ile Thr Pro Gly Val Glu Arg Val
145             150             155             160

Leu Arg Ala Val Ala Gln Ala His Lys Arg Thr Gly Val Pro Ile Ser
            165             170             175

Thr His Thr His Ala Gly Leu Arg Arg Gly Leu Glu Gln Gln Arg Ile
            180             185             190

Phe Glu Glu Glu Gly Val Asp Leu Ser Arg Val Val Ile Gly His Ser
        195             200             205

Gly Asp Ser Thr Asp Val Gly Tyr Leu Glu Glu Leu Val Ala Ala Gly
    210             215             220

Ser Tyr Leu Gly Met Asp Arg Phe Gly Leu Asp Val Ile Leu Pro Phe
225             230             235             240

Glu Asp Arg Val Asn Ile Val Ala Gln Met Cys Glu Arg Gly His Ala
            245             250             255
```

-continued

```
Asp Lys Met Val Leu Ser His Asp Ala Ser Cys Tyr Phe Asp Ala Leu
            260                 265                 270

Pro Glu Ala Leu Leu Pro Val Ala Ala Pro Asn Trp Asn Tyr Leu His
            275                 280                 285

Ile His Asn Asp Val Ile Pro Ala Leu Lys Gln Arg Gly Val Thr Asp
            290                 295                 300

Glu Gln Leu His Thr Met Leu Val Asp Asn Pro Arg Arg Ile Phe Glu
305                 310                 315                 320

Arg Gln Gly Gly Tyr Glu
                325
```

```
<210> SEQ ID NO 72
<211> LENGTH: 326
<212> TYPE: PRT
<213> ORGANISM: Mycobacterium shimoidei

<400> SEQUENCE: 72
```

```
Met Ser Gln Leu Asn Thr Ala Arg Gly Pro Ile Asp Thr Ala Asp Leu
1                   5                   10                  15

Gly Val Thr Leu Met His Glu His Val Phe Ile Met Thr Thr Glu Val
            20                  25                  30

Ala Gln Asn Tyr Pro Glu Ala Trp Gly Asp Glu Glu Gln Arg Val Ala
            35                  40                  45

Asp Ala Ile Thr Arg Leu Asn Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Arg Phe His Tyr Gln Gly Pro
            100                 105                 110

Gly Thr Gln Leu Asp Gly Pro Glu Ile Met Thr Asp Met Phe Val Arg
            115                 120                 125

Asp Ile Glu Gln Gly Ile Ala Asp Thr Gly Ile Lys Ala Ala Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Ala Asp Leu Ser Arg Val Ile Ile Gly His Ser
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Ile Asp Val Ile Ser Pro Phe
225                 230                 235                 240

Glu Asp Arg Val Asn Ile Val Ala Arg Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Leu Pro Val Val Ala Pro Asn Trp His Tyr Leu His
            275                 280                 285
```

-continued

```
Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Thr Gly Ala Tyr Glu
                325

<210> SEQ ID NO 73
<211> LENGTH: 326
<212> TYPE: PRT
<213> ORGANISM: Mycobacterium shimoidei

<400> SEQUENCE: 73

Met Ser Gln Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
                20                  25                  30

Ala Gln Asn Tyr Pro Glu Ala Trp Gly Asp Glu Glu Gln Arg Val Ala
            35                  40                  45

Asp Ala Ile Thr Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Arg Phe His Tyr Gln Gly Pro
                100                 105                 110

Gly Thr Gln Leu Asp Gly Pro Glu Ile Met Thr Asp Met Phe Val Arg
            115                 120                 125

Asp Ile Glu Gln Gly Ile Ala Asp Thr Gly Ile Lys Ala Ala Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Ile Asp Val Ile Ser Pro Phe
225                 230                 235                 240

Glu Asp Arg Val Asn Ile Val Ala Gln Met Cys Glu Arg Gly His Ala
            245                 250                 255

Asp Lys Met Val Leu Ser His Asp Ala Asn Cys Tyr Phe Asp Ala Leu
            260                 265                 270

Pro Glu Glu Leu Leu Pro Val Val Ala Pro Asn Trp His Tyr Leu His
            275                 280                 285

Ile His Asn Asp Val Ile Pro Ala Leu Lys Glu Arg Gly Val Thr Asp
    290                 295                 300
```

```
Glu Gln Leu His Thr Met Leu Val Asp Asn Pro Arg Arg Ile Phe Glu
305                 310                 315                 320

Arg Thr Gly Ala Tyr Glu
                325

<210> SEQ ID NO 74
<211> LENGTH: 325
<212> TYPE: PRT
<213> ORGANISM: Mycobacterium bohemicum

<400> SEQUENCE: 74

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Gln Arg Val Ala
                35                  40                  45

Asp Ala Ile Thr Arg Leu Asn Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Cys Phe His Tyr Leu Gly Pro
                100                 105                 110

Gly Ala Ala Leu Gly Gly Pro Glu Val Met Thr Asp Met Phe Val Arg
                115                 120                 125

Asp Ile Glu Gln Gly Ile Ala Asp Thr Gly Val Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Arg Arg Thr Gly Val Pro Ile Ser
                165                 170                 175

Thr His Thr His Ala Gly Leu Arg Arg Gly Leu Glu Gln Gln Arg Ile
                180                 185                 190

Phe Glu Glu Glu Gly Val Asp Leu Ser Arg Val Val Ile Gly His Ser
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Ile Asp Val Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
                260                 265                 270

Pro Glu Glu Leu Leu Ala Val Ala Ala Pro Asn Trp His Tyr Leu His
        275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Arg Gly Ala Tyr
                325
```

-continued

```
<210> SEQ ID NO 75
<211> LENGTH: 326
<212> TYPE: PRT
<213> ORGANISM: Mycobacterium kansasii

<400> SEQUENCE: 75

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
            20                  25                  30

Val Gln Asn Tyr Pro Glu Ala Trp Gly Asp Glu Asp Lys Arg Val Ala
        35                  40                  45

Asp Ala Val Ala Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
                85                  90                  95

Leu Tyr Thr Tyr Asn Asp Val Pro Phe Cys Phe His Tyr Leu Gly Pro
            100                 105                 110

Gly Thr Gln Leu Asp Gly Pro Glu Thr Met Thr Asp Leu Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Asp Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Val Ile Gly His Ser
        195                 200                 205

Gly Asp Ser Thr Asp Val Gly Tyr Leu Glu Glu Leu Val Ala Ala Gly
    210                 215                 220

Ser Tyr Leu Gly Met Asp Arg Phe Gly Leu Asp Val Ile Leu Pro Phe
225                 230                 235                 240

Glu Asp Arg Val Asn Ile Val Ala Gln Met Cys Glu Arg Gly His Ala
            245                 250                 255

Asp Lys Met Val Leu Ser His Asp Ala Ser Cys Tyr Phe Asp Ala Leu
            260                 265                 270

Pro Glu Ala Leu Leu Pro Val Ala Ala Pro Asn Trp Asn Tyr Leu His
        275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Glu
                325

<210> SEQ ID NO 76
<211> LENGTH: 326
<212> TYPE: PRT
<213> ORGANISM: Mycobacterium avium
```

-continued

<400> SEQUENCE: 76

Met Ser Glu Leu Asn Thr Ala Arg Gly Pro Ile Asp Thr Ala Ala Leu
1               5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Glu Gln Arg Val Ala
            35                  40                  45

Asp Ala Ile Asp Arg Leu Asn Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Cys Phe His Tyr Leu Gly Pro
                100                 105                 110

Gly Ala Glu Leu Gly Gly Pro Glu Ile Met Thr Asp Met Phe Val Arg
            115                 120                 125

Asp Ile Glu Gln Gly Ile Ala Asp Thr Gly Ile Lys Ala Gly Ile Leu
        130                 135                 140

Lys Cys Ala Thr Asp Ala Pro Gly Val Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Ile Asp Ala Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Val Pro Gln Val Met Pro Asn Trp His Tyr Leu His
            275                 280                 285

Ile His Asn Asp Val Ile Pro Ala Leu Lys Gln Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Pro Tyr Gly
                325

<210> SEQ ID NO 77
<211> LENGTH: 335
<212> TYPE: PRT
<213> ORGANISM: Mycobacterium sp.

<400> SEQUENCE: 77

Met Gly Tyr Val Ser Gln Pro Gly Ile Ala Ser Glu Leu Asn Thr Ala
1               5                   10                  15

Arg Gly Pro Ile Asp Thr Ala Asp Leu Gly Val Thr Leu Met His Glu
                20                  25                  30

```
His Val Phe Ile Met Thr Thr Glu Ile Ala Leu Asn Tyr Pro Glu Ala
        35                  40                  45

Trp Gly Asp Glu Glu Lys Arg Val Ala Asp Ala Val Thr Arg Leu Asn
    50                  55                  60

Glu Leu Lys Ala Arg Gly Val Asp Thr Ile Val Asp Leu Thr Val Ile
65                  70                  75                  80

Gly Leu Gly Arg Tyr Ile Pro Arg Ile Ala Lys Val Ala Ala Ala Thr
                85                  90                  95

Glu Leu Asn Ile Val Val Ala Thr Gly Leu Tyr Thr Tyr Asn Asp Val
            100                 105                 110

Pro Phe Cys Phe His Tyr Met Gly Pro Gly Ala Gln Leu Gly Gly Pro
        115                 120                 125

Glu Ile Met Thr Asp Met Phe Val Arg Asp Ile Glu Gln Gly Ile Ala
    130                 135                 140

Asp Thr Gly Ile Lys Ala Gly Ile Leu Lys Cys Ala Thr Asp Glu Pro
145                 150                 155                 160

Gly Ile Thr Pro Gly Val Glu Arg Val Leu Arg Ala Val Ala Gln Ala
                165                 170                 175

His Lys Arg Thr Gly Val Pro Ile Ser Thr His Thr His Ala Gly Leu
            180                 185                 190

Arg Arg Gly Leu Glu Gln Gln Arg Ile Phe Glu Glu Glu Gly Val Asp
            195                 200                 205

Leu Ser Arg Val Ile Ile Gly His Ser Gly Asp Ser Thr Asp Val Gly
    210                 215                 220

Tyr Leu Glu Glu Leu Ile Ala Ala Gly Ser Tyr Leu Gly Met Asp Arg
225                 230                 235                 240

Phe Gly Ile Asp Val Ile Leu Pro Phe Glu Glu Arg Val Asn Ile Val
                245                 250                 255

Ala Thr Met Cys Glu Arg Gly His Ala Asp Lys Met Val Leu Ser His
            260                 265                 270

Asp Ala Asn Cys Tyr Phe Asp Ala Leu Pro Glu Glu Met Leu Ala Val
            275                 280                 285

Ala Ala Pro Asn Trp His Tyr Leu His Ile His Asn Asp Val Ile Pro
    290                 295                 300

Ala Leu Lys Gln Arg Gly Val Thr Asp Glu Gln Leu His Thr Met Leu
305                 310                 315                 320

Val Asp Asn Pro Arg Arg Ile Phe Glu Arg Gln Gly Ala Tyr Gln
                325                 330                 335
```

<210> SEQ ID NO 78
<211> LENGTH: 325
<212> TYPE: PRT
<213> ORGANISM: Mycobacterium sp.

<400> SEQUENCE: 78

```
Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Lys Arg Val Ala
        35                  40                  45

Asp Ala Ile Thr Arg Leu Asn Glu Leu Lys Ser Arg Gly Val His Thr
    50                  55                  60
```

```
Ile Val Asp Leu Thr Val Ile Gly Leu Gly Arg Tyr Ile Pro Arg Ile
65              70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Arg Phe His Tyr Gln Gly Pro
            100                 105                 110

Gly Cys Met Leu Glu Gly Pro Glu Ile Met Thr Asp Met Phe Val Arg
            115                 120                 125

Asp Ile Glu Gln Gly Ile Ala Asp Thr Gly Val Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Val
            180                 185                 190

Phe Ala Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Ile Asp Leu Ile Leu Pro Phe
225                 230                 235                 240

Glu Asp Arg Val Asn Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Val Pro Val Ala Thr Pro Asn Trp His Tyr Leu His
            275                 280                 285

Ile His Asn Asp Val Ile Pro Ala Leu Lys Glu Arg Gly Val Thr Asp
    290                 295                 300

Glu Gln Val His Thr Met Leu Val Asp Asn Pro Arg Arg Ile Phe Glu
305                 310                 315                 320

Arg Gln Gly Gly Tyr
                325
```

```
<210> SEQ ID NO 79
<211> LENGTH: 326
<212> TYPE: PRT
<213> ORGANISM: Mycobacterium haemophilum

<400> SEQUENCE: 79
```

```
Met Ser Glu Leu Asn Thr Ala Arg Gly Pro Ile Ser Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Gln Arg Val Ala
            35                  40                  45

Asp Ala Ile Ala Arg Leu Ser Glu Leu Lys Ala Arg Gly Val Asp Thr
    50                  55                  60

Ile Val Asp Leu Thr Val Ile Gly Leu Gly Arg Tyr Ile Pro Arg Ile
65              70                  75                  80

Ala Arg Val Ala Ala Ala Thr Glu Leu Asn Ile Val Val Ala Thr Gly
                85                  90                  95
```

-continued

```
Leu Tyr Thr Tyr Asn Asp Val Pro Phe Tyr Phe His Tyr Leu Gly Pro
            100                 105                 110

Gly Ala Pro Leu Asn Gly Pro Glu Ile Met Thr Asp Met Phe Val Arg
            115                 120                 125

Asp Ile Glu Gln Gly Val Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Ala Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Asn Gly
    210                 215                 220

Ser Tyr Leu Gly Met Asp Arg Phe Gly Val Asp Val Ile Leu Pro Phe
225                 230                 235                 240

Glu Asp Arg Val Ser Ile Val Ala Gln Met Cys Glu Arg Gly His Ala
                245                 250                 255

Gly Lys Met Val Leu Ser His Asp Ala Asn Cys Tyr Phe Asp Ala Leu
            260                 265                 270

Pro Glu Ala Leu Gln Pro Val Ala Ala Pro Asn Trp His Tyr Leu His
            275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Thr Tyr Glu
                325

<210> SEQ ID NO 80
<211> LENGTH: 326
<212> TYPE: PRT
<213> ORGANISM: Mycobacterium persicum

<400> SEQUENCE: 80

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
            20                  25                  30

Ala Gln Asn Tyr Pro Glu Ala Trp Gly Asp Glu Asp Arg Arg Val Ala
            35                  40                  45

Asp Ala Val Ala Arg Leu Asn Glu Leu Lys Ser Arg Gly Val Asp Thr
    50                  55                  60

Ile Val Asp Leu Thr Val Ile Gly Leu Gly Arg Tyr Val Pro Arg Ile
65                  70                  75                  80

Ala Arg Val Ala Ala Gln Thr Glu Leu Asn Ile Val Val Ala Thr Gly
                85                  90                  95

Leu Tyr Thr Tyr Asn Asp Val Pro Phe Cys Phe His Tyr Leu Gly Pro
            100                 105                 110

Gly Thr Gln Leu Asp Gly Pro Glu Thr Met Thr Asp Leu Phe Val Arg
            115                 120                 125
```

-continued

```
Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
                180                 185                 190

Phe Glu Glu Glu Gly Val Asp Leu Ser Arg Val Val Ile Gly His Ser
                195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Leu Asp Val Ile Leu Pro Phe
225                 230                 235                 240

Glu Glu Arg Val Ala Ile Val Ala Gln Met Cys Glu Arg Gly His Ala
                245                 250                 255

Asp Lys Met Val Leu Ser His Asp Ala Thr Cys Tyr Phe Asp Ala Leu
                260                 265                 270

Pro Glu Ala Leu Leu Pro Val Ala Ala Pro Asn Trp His Tyr Leu His
                275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Asp
                325

<210> SEQ ID NO 81
<211> LENGTH: 326
<212> TYPE: PRT
<213> ORGANISM: Mycobacterium persicum

<400> SEQUENCE: 81

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
                20                  25                  30

Ala Gln Asn Tyr Pro Glu Ala Trp Gly Asp Glu Asp Arg Arg Val Ala
            35                  40                  45

Asp Ala Val Ala Arg Leu Asn Glu Leu Lys Ser Arg Gly Val Asp Thr
    50                  55                  60

Ile Val Asp Leu Thr Val Ile Gly Leu Gly Arg Tyr Val Pro Arg Ile
65                  70                  75                  80

Ala Arg Val Ala Ala Glu Thr Glu Leu Asn Ile Val Val Ala Thr Gly
                85                  90                  95

Leu Tyr Thr Tyr Asn Asp Val Pro Phe Cys Phe His Tyr Leu Gly Pro
                100                 105                 110

Gly Thr Gln Leu Asp Gly Pro Glu Thr Met Thr Asp Leu Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160
```

-continued

```
Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Leu Asp Val Ile Leu Pro Phe
225                 230                 235                 240

Glu Glu Arg Val Ala Ile Val Ala Gln Met Cys Glu Arg Gly His Ala
            245                 250                 255

Asp Lys Met Val Leu Ser His Asp Ala Thr Cys Tyr Phe Asp Ala Leu
            260                 265                 270

Pro Glu Ala Leu Leu Pro Val Ala Ala Pro Asn Trp His Tyr Leu His
            275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Asp
                325

<210> SEQ ID NO 82
<211> LENGTH: 326
<212> TYPE: PRT
<213> ORGANISM: Mycobacterium sp.

<400> SEQUENCE: 82

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
            20                  25                  30

Val Gln Asn Tyr Pro Asp Ala Trp Gly Asp Glu Asp Lys Arg Val Ala
        35                  40                  45

Asp Ala Val Ala Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
            85                  90                  95

Leu Tyr Thr Tyr Asn Asp Val Pro Phe Cys Phe His Tyr Leu Gly Pro
            100                 105                 110

Gly Thr Gln Leu Asp Gly Pro Glu Thr Met Thr Asp Leu Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190
```

```
Phe Glu Glu Glu Gly Val Asp Leu Ser Arg Val Val Ile Gly His Ser
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Leu Asp Val Ile Leu Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
                260                 265                 270

Pro Glu Ala Leu Leu Pro Val Ala Ala Pro Asn Trp Asn Tyr Leu His
        275                 280                 285

Ile His Asn Asp Val Ile Pro Ala Leu Lys Gln Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ala Tyr Glu
                325
```

<210> SEQ ID NO 83
<211> LENGTH: 326
<212> TYPE: PRT
<213> ORGANISM: Mycobacterium sp.

<400> SEQUENCE: 83

```
Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
        20                  25                  30

Ala Leu Asn Tyr Pro Glu Ala Trp Gly Asp Glu Glu Lys Arg Val Ala
        35                  40                  45

Asp Ala Val Ala Arg Leu Asn Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Lys Val Ala Ala Ser Thr Asp Leu Asn Ile Val Val Ala Thr Gly
                85                  90                  95

Leu Tyr Thr Tyr Asn Asp Val Pro Phe Cys Phe His Tyr Met Gly Pro
        100                 105                 110

Gly Ala Gln Leu Gly Gly Pro Glu Ile Met Thr Asp Met Phe Val Arg
        115                 120                 125

Asp Ile Glu Gln Gly Ile Ala Asp Thr Gly Ile Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
        165                 170                 175

Thr His Thr His Ala Gly Leu Arg Arg Gly Leu Glu Gln Gln Arg Ile
        180                 185                 190

Phe Glu Glu Glu Gly Val Asp Leu Ser Arg Val Ile Ile Gly His Ser
        195                 200                 205

Gly Asp Ser Thr Asp Val Gly Tyr Leu Glu Glu Leu Ile Ala Ala Gly
        210                 215                 220
```

```
Ser Tyr Leu Gly Met Asp Arg Phe Gly Ile Asp Val Ile Leu Pro Phe
225                 230                 235                 240

Glu Glu Arg Val Asn Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Met Leu Ala Val Ala Ala Pro Asn Trp His Tyr Leu His
        275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ala Tyr Gln
                325

<210> SEQ ID NO 84
<211> LENGTH: 326
<212> TYPE: PRT
<213> ORGANISM: Mycobacterium avium

<400> SEQUENCE: 84

Met Ser Glu Leu Asn Thr Ala Arg Gly Pro Ile Asp Thr Ala Ala Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Gln Arg Val Ala
        35                  40                  45

Asp Ala Ile Asp Arg Leu Asn Glu Leu Lys Ala Arg Gly Val Asp Thr
    50                  55                  60

Ile Val Asp Leu Thr Val Ile Gly Arg Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Cys Phe His Tyr Leu Gly Pro
            100                 105                 110

Gly Ala Glu Leu Gly Gly Pro Glu Ile Met Thr Asp Met Phe Val Arg
        115                 120                 125

Asp Ile Glu Gln Gly Ile Ala Asp Thr Gly Ile Lys Ala Gly Ile Leu
    130                 135                 140

Lys Cys Ala Thr Asp Ala Pro Gly Val Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
            180                 185                 190

Phe Glu Glu Glu Gly Val Asp Leu Ser Arg Val Val Ile Gly His Ser
        195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Ile Asp Ala Ile Ser Pro Phe
225                 230                 235                 240

Glu Asp Arg Val Asn Ile Val Ala Gln Met Cys Glu Arg Gly His Ala
                245                 250                 255
```

-continued

```
Asp Lys Met Val Leu Ser His Asp Ala Asn Cys Tyr Phe Asp Ala Leu
        260             265             270

Pro Glu Glu Leu Val Pro Gln Val Met Pro Asn Trp His Tyr Leu His
        275             280             285

Ile His Asn Asp Val Ile Pro Ala Leu Lys Gln Arg Gly Val Thr Asp
    290             295             300

Glu Gln Leu His Thr Met Leu Val Asp Asn Pro Arg Arg Ile Phe Glu
305             310             315             320

Arg Gln Gly Pro Tyr Gly
                325

<210> SEQ ID NO 85
<211> LENGTH: 326
<212> TYPE: PRT
<213> ORGANISM: Mycobacterium interjectum

<400> SEQUENCE: 85

Met Ser Glu Leu Asn Thr Ala Arg Gly Ala Ile Asp Thr Ala Asp Leu
1               5               10              15

Gly Val Thr Leu Met His Glu His Val Phe Ile Met Thr Thr Glu Ile
        20              25              30

Ala Leu Asn Tyr Pro Glu Ala Trp Gly Asp Glu Glu Gln Arg Val Ala
        35              40              45

Asp Ala Ile Asp Arg Leu Asn Glu Leu Lys Ala Arg Gly Val Asp Thr
    50              55              60

Ile Val Asp Leu Thr Val Ile Gly Leu Gly Arg Tyr Ile Pro Arg Ile
65              70              75              80

Ala Arg Val Ala Ala Ala Thr Glu Leu Asn Ile Val Val Ala Thr Gly
            85              90              95

Leu Tyr Thr Tyr Asn Asp Val Pro Phe Arg Phe His Tyr Gln Gly Pro
        100             105             110

Gly Ala Pro Leu Asp Gly Pro Glu Ile Met Thr Asp Met Phe Val Arg
        115             120             125

Asp Ile Glu Glu Gly Ile Ala Asp Thr Gly Val Lys Ala Gly Ile Leu
    130             135             140

Lys Cys Ala Thr Asp Glu Pro Gly Val Thr Pro Gly Val Glu Arg Val
145             150             155             160

Leu Arg Ala Val Ala Gln Ala His Lys Arg Thr Gly Val Pro Ile Ser
            165             170             175

Thr His Thr His Ala Gly Leu Arg Arg Gly Leu Glu Gln Gln Arg Ile
        180             185             190

Phe Ser Glu Glu Gly Val Asp Leu Ser Arg Val Val Ile Gly His Ser
        195             200             205

Gly Asp Thr Thr Asp Val Gly Tyr Leu Glu Glu Leu Ile Ala Ala Gly
    210             215             220

Ser Tyr Leu Gly Met Asp Arg Phe Gly Ile Asp Leu Ile Ser Pro Phe
225             230             235             240

Glu Asp Arg Val Asn Ile Val Ala Thr Met Cys Glu Arg Gly His Ala
            245             250             255

Asp Lys Met Val Leu Ser His Asp Ala Asn Cys Tyr Phe Asp Ala Leu
        260             265             270

Pro Glu Glu Leu Leu Pro Val Ala Ala Pro Asn Trp His Tyr Leu His
        275             280             285
```

-continued

```
Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ala Tyr Glu
                325

<210> SEQ ID NO 86
<211> LENGTH: 326
<212> TYPE: PRT
<213> ORGANISM: Mycobacterium sp.

<400> SEQUENCE: 86

Met Ser Glu Leu Asn Thr Ala Arg Gly Leu Ile Asp Thr Ala Asp Leu
1               5                   10                  15

Gly Val Thr Leu Met His Glu His Val Phe Ile Met Thr Thr Glu Val
            20                  25                  30

Val Gln Asn Tyr Pro Glu Ala Trp Gly Asp Glu Asp Gln Arg Val Ala
        35                  40                  45

Asp Ala Val Ala Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
            85                  90                  95

Leu Tyr Thr Tyr Asn Asp Val Pro Phe Cys Phe His Tyr Leu Gly Pro
            100                 105                 110

Gly Thr Gln Leu Asp Gly Pro Glu Thr Met Thr Asp Leu Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Leu Asp Val Ile Leu Pro Phe
225                 230                 235                 240

Glu Asp Arg Val Asn Ile Val Ala Arg Met Cys Glu Arg Gly His Ala
            245                 250                 255

Asp Lys Met Val Leu Ser His Asp Ala Thr Cys Tyr Phe Asp Ala Leu
            260                 265                 270

Pro Glu Ala Leu Leu Pro Val Ala Ala Pro Asn Trp Asn Tyr Leu His
            275                 280                 285

Ile His Asn Asp Val Ile Pro Ala Leu Lys Gln Arg Gly Val Thr Asp
    290                 295                 300
```

```
Glu Gln Leu His Thr Met Leu Val Asp Asn Pro Gln Arg Ile Phe Glu
305             310             315             320

Arg Gln Gly Ala Tyr Glu
            325

<210> SEQ ID NO 87
<211> LENGTH: 326
<212> TYPE: PRT
<213> ORGANISM: Mycobacterium persicum

<400> SEQUENCE: 87

Met Ser Glu Leu Asn Thr Ala Arg Gly Pro Ile Asp Thr Ala Asp Leu
1               5               10              15

Gly Val Thr Leu Met His Glu His Val Phe Ile Met Thr Thr Glu Val
                20              25              30

Ala Gln Asn Tyr Pro Glu Ala Trp Gly Asp Glu Asp Arg Arg Val Ala
            35              40              45

Asp Ala Val Ala Arg Leu Asn Glu Leu Lys Ser Arg Gly Gly Asp Thr
        50              55              60

Ile Val Asp Leu Thr Val Ile Gly Leu Gly Arg Tyr Val Pro Arg Ile
65              70              75              80

Ala Arg Val Ala Ala Gln Thr Glu Leu Asn Ile Val Val Ala Thr Gly
                85              90              95

Leu Tyr Thr Tyr Asn Asp Val Pro Phe Cys Phe His Tyr Leu Gly Pro
                100             105             110

Gly Thr Gln Leu Asp Gly Pro Glu Thr Met Thr Asp Leu Phe Val Arg
            115             120             125

Asp Ile Glu Gln Gly Ile Ala Asp Thr Gly Ile Lys Ala Gly Ile Leu
        130             135             140

Lys Cys Ala Thr Asp Glu Pro Gly Ile Thr Pro Gly Val Glu Arg Val
145             150             155             160

Leu Arg Ala Val Ala Gln Ala His Lys Arg Thr Gly Val Pro Ile Ser
                165             170             175

Thr His Thr His Ala Gly Leu Arg Arg Gly Leu Glu Gln Gln Arg Ile
                180             185             190

Phe Glu Glu Glu Gly Val Asp Leu Ser Arg Val Val Ile Gly His Ser
            195             200             205

Gly Asp Ser Thr Asp Val Gly Tyr Leu Glu Glu Leu Ile Ala Ala Gly
        210             215             220

Ser Tyr Leu Gly Met Asp Arg Phe Gly Leu Asp Val Ile Leu Pro Phe
225             230             235             240

Glu Glu Arg Val Ala Ile Val Ala Gln Met Cys Glu Arg Gly His Ala
            245             250             255

Asp Lys Met Val Leu Ser His Asp Ala Thr Cys Tyr Phe Asp Ala Leu
            260             265             270

Pro Glu Ala Leu Leu Pro Val Ala Ala Pro Asn Trp His Tyr Leu His
        275             280             285

Ile His Asn Asp Val Ile Pro Ala Leu Lys Gln Arg Gly Val Thr Asp
    290             295             300

Glu Gln Leu His Thr Met Leu Val Asp Asn Pro Arg Arg Ile Phe Glu
305             310             315             320

Arg Gln Gly Gly Tyr Asp
            325
```

<210> SEQ ID NO 88
<211> LENGTH: 326
<212> TYPE: PRT
<213> ORGANISM: Mycobacterium kansasii

<400> SEQUENCE: 88

Met Ser Glu Leu Asn Pro Ala Arg Gly Pro Ile Asp Thr Ala Asp Leu
1               5                   10                  15

Gly Val Thr Leu Met His Glu His Val Phe Ile Met Thr Thr Glu Val
            20                  25                  30

Val Gln Asn Tyr Pro Asp Ala Trp Gly Asp Glu Asp Lys Arg Val Ala
        35                  40                  45

Asp Ala Val Ala Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
                85                  90                  95

Leu Tyr Thr Tyr Asn Asp Val Pro Phe Cys Phe His Tyr Leu Gly Pro
            100                 105                 110

Gly Thr Gln Leu Asp Gly Pro Glu Thr Met Thr Asp Leu Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Leu Asp Val Ile Leu Pro Phe
225                 230                 235                 240

Glu Asp Arg Val Asn Ile Val Ala Gln Met Cys Glu Arg Gly His Ala
            245                 250                 255

Asp Lys Met Val Leu Ser His Asp Ala Asn Cys Tyr Phe Asp Ala Leu
            260                 265                 270

Pro Glu Ala Leu Leu Pro Val Ala Ala Pro Asn Trp Asn Tyr Leu His
            275                 280                 285

Ile His Asn Asp Val Ile Pro Ala Leu Lys Gln Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ala Tyr Glu
                325

<210> SEQ ID NO 89
<211> LENGTH: 326
<212> TYPE: PRT
<213> ORGANISM: Mycobacterium fragae

<400> SEQUENCE: 89

Met Ser Gln Leu Asn Thr Ala Arg Gly Pro Ile Asp Thr Gly Asp Leu
1               5                   10                  15

Gly Val Thr Leu Met His Glu His Val Phe Ile Met Thr Thr Glu Ile
                20                  25                  30

Ala Leu Asn Tyr Pro Glu Ala Trp Gly Asp Glu Asp Gln Arg Val Ser
            35                  40                  45

Asp Ala Val Asn Arg Leu Asn Glu Leu Lys Ser Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Glu Thr Asp Leu Asn Ile Val Val Ala Thr Gly
                85                  90                  95

Leu Tyr Thr Tyr Asn Asp Val Pro Phe Arg Phe His Tyr Gln Gly Pro
                100                 105                 110

Gly Thr Gln Leu Asp Gly Pro Glu Ile Met Thr Asp Met Phe Val Arg
            115                 120                 125

Asp Ile Glu Glu Gly Ile Ala Asp Thr Gly Ile Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
                180                 185                 190

Phe Glu Glu Glu Gly Val Asp Leu Ser Arg Val Ile Ile Gly His Ser
            195                 200                 205

Gly Asp Ser Thr Asp Ile Gly Tyr Leu Glu Glu Leu Ile Ala Ala Gly
        210                 215                 220

Ser Tyr Leu Gly Met Asp Arg Phe Gly Ile Asp Val Ile Leu Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Met Pro Val Ala Ala Pro Asn Trp His Tyr Leu His
            275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ala Tyr Gln
                325

<210> SEQ ID NO 90
<211> LENGTH: 326
<212> TYPE: PRT
<213> ORGANISM: Mycobacterium kubicae

<400> SEQUENCE: 90

Met Ser Glu Leu Asn Thr Ala Arg Gly Pro Ile Asp Thr Ala Asn Leu
1               5                   10                  15

Gly Val Thr Leu Met His Glu His Val Phe Ile Met Thr Thr Glu Ile
                20                  25                  30

-continued

```
Ile Gln Asn Tyr Pro Glu Ala Trp Gly Asp Glu Glu Lys Arg Val Ala
        35                  40                  45

Asp Ala Val Ala Arg Leu Asn Glu Leu Lys Ser Arg Gly Val Asp Ser
    50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
                85                  90                  95

Ile Tyr Thr Tyr Asn Asp Val Pro Phe His Phe His Tyr Ser Gly Pro
                100                 105                 110

Gly Thr Ile Leu Asn Gly Pro Glu Val Met Val Asp Met Phe Val Arg
            115                 120                 125

Asp Ile Glu Gln Gly Ile Ala Asp Thr Gly Val Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ser Gly
    210                 215                 220

Ser Tyr Leu Gly Met Asp Arg Phe Gly Leu Asp Leu Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Val Val Pro Gln Val Leu Pro Asn Trp His Tyr Leu His
            275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Glu
                325
```

<210> SEQ ID NO 91
<211> LENGTH: 326
<212> TYPE: PRT
<213> ORGANISM: Mycobacterium kubicae

<400> SEQUENCE: 91

```
Met Ser Glu Leu Asn Thr Ala Arg Gly Pro Ile Asp Thr Ala Asn Leu
1               5                   10                  15

Gly Val Thr Leu Met His Glu His Val Phe Ile Met Thr Thr Glu Ile
            20                  25                  30

Ile Gln Asn Tyr Pro Glu Ala Trp Gly Asp Glu Glu Lys Arg Val Ala
        35                  40                  45

Asp Ala Val Ala Arg Leu Asn Glu Leu Lys Ser Arg Gly Val Asp Ser
    50                  55                  60
```

```
Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
                85                  90                  95

Ile Tyr Thr Tyr Asn Asp Val Pro Phe His Phe His Tyr Ser Gly Pro
            100                 105                 110

Gly Thr Ile Leu Asn Gly Pro Glu Val Met Val Asp Met Phe Val Arg
            115                 120                 125

Asp Ile Glu Gln Gly Ile Ala Asp Thr Gly Val Lys Ala Gly Ile Leu
    130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Ile Gly Tyr Leu Glu Glu Leu Ile Ala Ser Gly
    210                 215                 220

Ser Tyr Leu Gly Met Asp Arg Phe Gly Leu Asp Leu Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Val Val Pro Gln Val Leu Pro Asn Trp His Tyr Leu His
            275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Gly Tyr Glu
                325
```

<210> SEQ ID NO 92
<211> LENGTH: 326
<212> TYPE: PRT
<213> ORGANISM: Mycobacterium sp. E3198

<400> SEQUENCE: 92

```
Met Ser Glu Leu Asn Thr Ala Arg Gly Ala Ile Asp Thr Ala Asp Leu
1               5                   10                  15

Gly Val Thr Leu Met His Glu His Val Phe Ile Met Thr Thr Glu Ile
            20                  25                  30

Ala Leu Asn Tyr Pro Glu Ala Trp Gly Asp Glu Glu Gln Arg Val Ala
        35                  40                  45

Asp Ala Ile Asp Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95
```

```
Leu Tyr Thr Tyr Asn Asp Val Pro Phe Arg Phe His Tyr Gln Gly Pro
            100                 105                 110

Gly Ala Pro Leu Asp Gly Pro Glu Ile Met Thr Asp Met Phe Val Arg
            115                 120                 125

Asp Ile Glu Glu Gly Ile Ala Asp Thr Gly Val Lys Ala Gly Ile Leu
        130                 135                 140

Lys Cys Ala Thr Asp Glu Pro Gly Val Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Ser Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Ile Asp Leu Ile Ser Pro Phe
225                 230                 235                 240

Glu Asp Arg Val Asn Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Leu Pro Val Ala Ala Pro Asn Trp His Tyr Leu His
            275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ala Tyr Ala
                325
```

```
<210> SEQ ID NO 93
<211> LENGTH: 326
<212> TYPE: PRT
<213> ORGANISM: Mycobacterium decipiens

<400> SEQUENCE: 93
```

```
Met Ser Ala Leu Asn Thr Ala Arg Gly Pro Ile Asp Thr Ala Asp Leu
1                   5                   10                  15

Gly Val Thr Leu Met His Glu His Val Phe Ile Met Thr Thr Glu Ile
            20                  25                  30

Ala Gln Asn Tyr Pro Glu Gly Trp Gly Asp Glu Glu Gln Arg Val Ala
            35                  40                  45

Asp Ala Ile Thr Arg Leu Ser Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Phe Phe His Tyr Leu Gly Pro
            100                 105                 110

Gly Gly Met Leu Asp Gly Pro Glu Ile Met Thr Asp Met Phe Val Arg
            115                 120                 125
```

-continued

```
Asp Ile Glu Glu Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Met Arg Thr Gly Val Pro Ile Ser
                165                 170                 175

Thr His Thr His Ala Gly Leu Arg Arg Gly Leu Glu Gln Gln Arg Ile
                180                 185                 190

Phe Ala Glu Glu Gly Val Asp Leu Ser Arg Val Ile Ile Gly His Ser
                195                 200                 205

Gly Asp Ser Thr Asp Val Gly Tyr Leu Glu Glu Leu Ile Ser Asn Gly
    210                 215                 220

Ser Tyr Leu Gly Met Asp Arg Phe Gly Ile Asp Leu Ile Leu Pro Phe
225                 230                 235                 240

Glu Glu Arg Val Asn Ile Val Ala Arg Leu Cys Glu Arg Gly His Ala
                245                 250                 255

Asp Lys Met Val Leu Ser His Asp Ala Asn Cys Tyr Phe Asp Ala Leu
                260                 265                 270

Pro Glu Ala Leu Val Pro Ala Ala Ala Pro Asn Trp His Tyr Leu His
                275                 280                 285

Ile His Asn Asp Val Ile Pro Ala Leu Lys Glu Arg Gly Val Thr Asp
    290                 295                 300

Glu Gln Val Arg Thr Met Leu Val Asp Asn Pro Arg Arg Ile Phe Glu
305                 310                 315                 320

Arg Gln Gly Gly Tyr Gln
                325

<210> SEQ ID NO 94
<211> LENGTH: 325
<212> TYPE: PRT
<213> ORGANISM: Mycobacterium sp.

<400> SEQUENCE: 94

Met Ser Glu Leu Asn Thr Ala Arg Gly Ser Ile Asp Thr Ala Asp Leu
1               5                   10                  15

Gly Val Thr Leu Met His Glu His Val Phe Ile Met Thr Thr Glu Ile
                20                  25                  30

Ala Leu Asn Tyr Pro Glu Ala Trp Gly Asp Glu Glu Gln Arg Val Ala
            35                  40                  45

Asp Ala Ile Thr Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Cys Phe His Tyr Met Gly Pro
                100                 105                 110

Gly Ala Gln Leu Gly Gly Pro Glu Ile Met Thr Glu Met Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160
```

```
Leu Arg Ala Val Ala Gln Ala His Lys Gln Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Ile Ile Gly His Ser
            195                 200                 205

Gly Asp Ser Thr Asp Val Gly Tyr Leu Glu Glu Leu Ile Ser Ala Gly
        210                 215                 220

Ser Tyr Leu Gly Met Asp Arg Phe Gly Ile Asp Val Ile Leu Pro Phe
225                 230                 235                 240

Glu Asp Arg Val Asn Ile Val Ala Thr Met Cys Glu Arg Gly His Ala
            245                 250                 255

Asp Lys Met Val Leu Ser His Asp Ala Asn Cys Tyr Phe Asp Ala Leu
            260                 265                 270

Pro Glu Glu Leu Leu Pro Val Ala Ala Pro Asn Trp His Tyr Leu His
            275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ser Tyr
                325

<210> SEQ ID NO 95
<211> LENGTH: 325
<212> TYPE: PRT
<213> ORGANISM: Mycobacterium sp. E342

<400> SEQUENCE: 95

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Leu Asn Tyr Pro Glu Ala Trp Gly Asp Glu Asp Lys Arg Val Ala
        35                  40                  45

Asp Ala Ile Ala Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Asp Leu Asn Ile Val Val Ala Thr Gly
            85                  90                  95

Leu Tyr Thr Tyr Asn Asp Ile Pro Phe Arg Phe His Tyr Glu Gly Pro
            100                 105                 110

Gly Gly Met Leu Asp Gly Pro Glu Ile Met Thr Asp Met Phe Val Lys
            115                 120                 125

Asp Ile Glu Gln Gly Ile Ala Asp Thr Gly Val Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190
```

```
Phe Glu Glu Glu Gly Val Asp Leu Thr Arg Val Val Ile Gly His Ser
        195                 200                 205

Gly Asp Ser Thr Asp Ile Gly Tyr Leu Glu Glu Leu Ile Ala Ala Gly
    210                 215                 220

Ser Tyr Leu Gly Met Asp Arg Phe Gly Leu Asp Val Ile Ser Pro Phe
225                 230                 235                 240

Glu Glu Arg Val Lys Ile Val Ala Gln Met Cys Glu Arg Gly His Ala
                245                 250                 255

Asp Lys Met Val Leu Ser His Asp Ala Asn Cys Tyr Phe Asp Ala Leu
                260                 265                 270

Pro Glu Glu Leu Val Pro Gln Met Ala Pro Asn Trp His Tyr Leu His
            275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ala Tyr
                325
```

```
<210> SEQ ID NO 96
<211> LENGTH: 325
<212> TYPE: PRT
<213> ORGANISM: Mycobacterium sp. 852002-10029_SCH5224772

<400> SEQUENCE: 96

Met Ser Glu Leu Asn Thr Ala Arg Gly Ser Ile Asp Thr Ala Gln Leu
1               5                   10                  15

Gly Val Thr Leu Met His Glu His Val Phe Ile Met Thr Thr Glu Ile
                20                  25                  30

Ala Glu Asn Tyr Pro Glu Ala Trp Gly Asp Glu Glu Arg Arg Val Ala
            35                  40                  45

Asp Ala Ile Asp Arg Leu Asn Glu Leu Lys Ser Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Glu Leu Gly Gly Pro Glu Ile Met Thr Asp Met Phe Val Arg
            115                 120                 125

Asp Ile Glu Gln Gly Ile Ala Asp Thr Gly Val Lys Ala Gly Ile Leu
    130                 135                 140

Lys Cys Ala Thr Asp Ala Pro Gly Val Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
                180                 185                 190

Phe Glu Glu Glu Gly Val Asp Leu Ser Arg Val Val Ile Gly His Ser
        195                 200                 205

Gly Asp Ser Thr Asp Val Gly Tyr Leu Glu Glu Leu Ile Ala Ala Gly
    210                 215                 220
```

```
Ser Tyr Leu Gly Met Asp Arg Phe Gly Ile Asp Ala Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Val Pro Gln Val Met Pro Asn Trp His Tyr Leu His
        275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Gln Thr Gly Ala Tyr
                325
```

```
<210> SEQ ID NO 97
<211> LENGTH: 326
<212> TYPE: PRT
<213> ORGANISM: Mycobacterium gastri

<400> SEQUENCE: 97
```

```
Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
            20                  25                  30

Val Gln Asn Tyr Pro Asp Ala Trp Gly Asp Glu Asp Lys Arg Val Ala
        35                  40                  45

Asp Ala Val Gly Arg Leu Asn Val Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
                85                  90                  95

Leu Tyr Thr Tyr Asn Asp Val Pro Phe Cys Phe His Tyr Leu Gly Pro
            100                 105                 110

Gly Thr Gln Leu Asp Gly Pro Glu Ile Met Thr Asp Leu Phe Val Arg
        115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Ile Ile Gly His Ser
        195                 200                 205

Gly Asp Ser Thr Asp Val Gly Tyr Leu Glu Glu Leu Val Ala Ala Gly
    210                 215                 220

Ser Tyr Leu Gly Met Asp Arg Phe Gly Ile Asp Val Ile Leu Pro Phe
225                 230                 235                 240

Glu Asp Arg Val Asn Ile Val Ala Thr Met Cys Glu Arg Gly His Ala
                245                 250                 255
```

```
Asp Lys Met Val Leu Ser His Asp Ala Asn Cys Tyr Phe Asp Ala Leu
            260                 265                 270

Pro Glu Ala Leu Leu Pro Val Ala Ala Pro Asn Trp His Tyr Leu His
            275                 280                 285

Ile His Asn Asp Val Ile Pro Ala Leu Thr Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ala Tyr Glu
                325
```

```
<210> SEQ ID NO 98
<211> LENGTH: 325
<212> TYPE: PRT
<213> ORGANISM: Mycobacterium riyadhense

<400> SEQUENCE: 98
```

```
Met Ser Glu Leu Asn Thr Ala Arg Gly Thr Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Gly Trp Gly Asp Glu Glu Lys Arg Val Ala
            35                  40                  45

Asp Ala Ile Thr Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Gln Val Ala Ala Gln Thr Glu Leu Asn Ile Val Val Ala Thr Gly
            85                  90                  95

Leu Tyr Thr Tyr Asn Asp Val Pro Phe Cys Phe His Phe Met Gly Pro
            100                 105                 110

Gly Gly Met Leu Asp Gly Pro Glu Ile Met Thr Asp Met Phe Val Arg
            115                 120                 125

Asp Ile Glu Gln Gly Ile Ala Asp Thr Gly Ile Lys Ala Ala Ile Leu
    130                 135                 140

Lys Cys Ala Thr Asp Glu Pro Gly Val Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Val Asp Val Ile Ser Pro Phe
225                 230                 235                 240

Glu Asp Arg Val Asn Ile Val Ala Gln Met Cys Glu Arg Gly His Ala
            245                 250                 255

Asp Lys Met Val Leu Ser His Asp Ala Asn Cys Tyr Phe Asp Ala Leu
            260                 265                 270

Pro Glu Ala Leu Val Pro Val Val Thr Pro Asn Trp His Tyr Leu His
            275                 280                 285
```

```
Ile His Asn Asp Val Ile Pro Ala Leu Lys Gln Arg Gly Val Thr Asp
    290                 295                 300

Glu Gln Val Gln Thr Met Leu Val Asp Asn Pro Arg Arg Ile Phe Glu
305                 310                 315                 320

Arg Gln Gly Gly Tyr
                325

<210> SEQ ID NO 99
<211> LENGTH: 326
<212> TYPE: PRT
<213> ORGANISM: Mycobacterium nebraskense

<400> SEQUENCE: 99

Met Ser Glu Leu Asn Thr Ala Arg Gly Pro Ile Asp Thr Ala Asp Leu
1               5                  10                  15

Gly Val Thr Leu Met His Glu His Val Phe Ile Met Thr Thr Glu Ile
                20                  25                  30

Ala Leu Asn Tyr Pro Glu Ala Trp Gly Asp Glu Glu Lys Arg Val Ala
            35                  40                  45

Asp Ala Ile Ala Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Arg Phe His Tyr Glu Gly Pro
                100                 105                 110

Gly Gly Met Leu Asp Gly Pro Glu Ile Met Thr Glu Met Phe Val Arg
            115                 120                 125

Asp Ile Glu Gln Gly Ile Ala Asp Thr Gly Val Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Thr Arg Val Val Ile Gly His Ser
            195                 200                 205

Gly Asp Ser Thr Asp Val Gly Tyr Leu Glu Glu Leu Val Ala Ala Gly
    210                 215                 220

Ser Tyr Leu Gly Met Asp Arg Phe Gly Leu Asp Val Ile Ser Pro Phe
225                 230                 235                 240

Glu Glu Arg Val Gly Ile Val Ala Thr Met Cys Glu Arg Gly His Ala
            245                 250                 255

Asp Lys Met Val Leu Ser His Asp Ala Asn Cys Tyr Phe Asp Ala Leu
            260                 265                 270

Pro Glu Glu Leu Val Pro Gln Met Ala Pro Asn Trp His Tyr Leu His
            275                 280                 285

Ile His Asn Asp Val Ile Pro Ala Leu Lys Glu Arg Gly Val Thr Asp
    290                 295                 300
```

-continued

Glu Gln Leu His Thr Met Leu Val Asp Asn Pro Arg Arg Ile Phe Glu
305                 310                 315                 320

Arg Gln Gly Ala Tyr Glu
                325

<210> SEQ ID NO 100
<211> LENGTH: 326
<212> TYPE: PRT
<213> ORGANISM: Mycobacterium kansasii

<400> SEQUENCE: 100

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
                20                  25                  30

Val Gln Asn Tyr Pro Asp Ala Trp Gly Asp Glu Asp Lys Arg Val Ala
                35                  40                  45

Asp Ala Val Ala Arg Leu Asn Glu Leu Lys Ser Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Gln Thr Glu Leu Asn Ile Val Val Ala Thr Gly
                85                  90                  95

Leu Tyr Thr Tyr Asn Asp Val Pro Phe Cys Phe His Tyr Leu Gly Pro
                100                 105                 110

Gly Thr Gln Leu Asp Gly Pro Glu Thr Met Thr Asp Leu Phe Val Arg
                115                 120                 125

Asp Ile Glu Gln Gly Ile Ala Asp Thr Gly Ile Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys His Thr Gly Val Pro Ile Ser
                165                 170                 175

Thr His Thr His Ala Gly Leu Arg Arg Gly Leu Glu Gln Gln Arg Ile
                180                 185                 190

Phe Glu Glu Glu Gly Val Asp Leu Ser Arg Val Val Ile Gly His Ser
                195                 200                 205

Gly Asp Ser Thr His Val Gly Tyr Leu Glu Glu Leu Ile Ala Ala Gly
        210                 215                 220

Ser Tyr Leu Gly Met Asp Arg Phe Gly Leu Asp Val Ile Leu Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
                260                 265                 270

Pro Glu Ala Leu Leu Pro Val Ala Ala Pro Asn Trp Asn Tyr Leu His
                275                 280                 285

Ile His Asn Asp Val Ile Pro Ala Leu Lys Gln Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ala Tyr Glu
                325

<210> SEQ ID NO 101
<211> LENGTH: 326
<212> TYPE: PRT
<213> ORGANISM: Mycobacterium sp. 852002-40037_SCH5390672

<400> SEQUENCE: 101

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Lys Arg Val Ala
        35                  40                  45

Asp Ala Ile Ala Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Ile Pro Phe Arg Phe His Tyr Glu Gly Pro
            100                 105                 110

Gly Gly Met Leu Gly Gly Pro Glu Ile Met Thr Asp Met Phe Val Lys
            115                 120                 125

Asp Ile Glu Val Gly Ile Ala Asp Thr Gly Val Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Val Asp Leu Thr Arg Val Val Ile Gly His Ser
            195                 200                 205

Gly Asp Ser Thr Asp Ile Gly Tyr Leu Glu Glu Leu Ile Ala Ala Gly
    210                 215                 220

Ser Tyr Leu Gly Met Asp Arg Phe Gly Leu Asp Val Ile Ser Pro Phe
225                 230                 235                 240

Glu Glu Arg Val Arg Ile Val Ala Glu Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Val Pro Gln Met Ala Pro Asn Trp His Tyr Leu His
            275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ser Tyr Glu
                325

<210> SEQ ID NO 102
<211> LENGTH: 326
<212> TYPE: PRT
<213> ORGANISM: Mycobacterium kubicae

```
<400> SEQUENCE: 102

Met Ser Glu Leu Asn Thr Ala Arg Gly Pro Ile Asp Thr Ala Asn Leu
1               5                   10                  15

Gly Val Thr Leu Met His Glu His Val Phe Ile Met Thr Thr Glu Ile
            20                  25                  30

Ile Gln Asn Tyr Pro Glu Ala Trp Gly Asp Glu Glu Lys Arg Val Ala
            35                  40                  45

Asp Ala Val Ala Arg Leu Asn Glu Leu Lys Ser Arg Gly Val Asp Ser
        50                  55                  60

Ile Val Asp Leu Thr Val Ile Gly Leu Gly Arg Tyr Ile Pro Arg Ile
65                  70                  75                  80

Ala Arg Val Ala Ala Gln Thr Asp Leu Asn Ile Val Val Ala Thr Gly
                85                  90                  95

Ile Tyr Thr Tyr Asn Asp Val Pro Phe His Phe His Tyr Asn Gly Pro
            100                 105                 110

Gly Thr Ile Leu Asn Gly Pro Glu Val Met Val Asp Met Phe Val Arg
            115                 120                 125

Asp Ile Glu Gln Gly Ile Ala Asp Thr Gly Val Lys Ala Gly Ile Leu
        130                 135                 140

Lys Cys Ala Thr Asp Glu Pro Gly Leu Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Asp Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Ile Gly Tyr Leu Glu Glu Leu Ile Ala Ser Gly
        210                 215                 220

Ser Tyr Leu Gly Met Asp Arg Phe Gly Leu Asp Leu Ile Ser Pro Phe
225                 230                 235                 240

Glu Asp Arg Val Asn Ile Val Ala Gln Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Val Val Pro Gln Val Leu Pro Asn Trp His Tyr Leu His
            275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Gly Tyr Glu
                325

<210> SEQ ID NO 103
<211> LENGTH: 326
<212> TYPE: PRT
<213> ORGANISM: Mycobacterium marinum

<400> SEQUENCE: 103

Met Ser Ala Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
            20                  25                  30
```

-continued

```
Ala Gln Asn Tyr Pro Glu Ala Trp Gly Asp Glu Glu Lys Arg Val Ala
        35                  40                  45

Asp Ala Ile Thr Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Ile Ala Ala Ala Thr Asp Leu Asn Ile Val Val Ala Thr Gly
                85                  90                  95

Leu Tyr Thr Tyr Asn Asp Val Pro Tyr Arg Phe His Tyr Gln Gly Pro
                100                 105                 110

Gly Gly Met Leu Asp Gly Pro Glu Ile Met Thr Asp Met Phe Val Arg
            115                 120                 125

Asp Ile Glu Gly Gly Ile Ala Asp Thr Gly Val Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Thr His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Ile Asp Leu Ile Leu Pro Phe
225                 230                 235                 240

Glu Asp Arg Val Asn Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Thr Ala Val Ala Thr Pro Asn Trp His Tyr Leu His
            275                 280                 285

Ile His Asn Asp Val Ile Pro Ala Leu Lys Glu Arg Gly Val Thr Asp
    290                 295                 300

Glu Gln Val His Thr Met Leu Val Asp Asn Pro Arg Arg Ile Phe Glu
305                 310                 315                 320

Arg Gln Gly Gly Tyr Gln
                325

<210> SEQ ID NO 104
<211> LENGTH: 326
<212> TYPE: PRT
<213> ORGANISM: Mycobacterium malmoense

<400> SEQUENCE: 104

Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Leu Asn Tyr Pro Glu Ala Trp Gly Asp Glu Asp Arg Arg Val Ala
        35                  40                  45

Asp Ala Ile Asp Arg Leu Asn Glu Leu Lys Ser Arg Gly Val Asp Thr
    50                  55                  60
```

-continued

```
Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Arg Phe His Tyr Glu Gly Pro
            100                 105                 110

Gly Gly Met Leu Asp Gly Pro Glu Ile Met Thr Glu Met Phe Val Arg
            115                 120                 125

Asp Ile Glu Gln Gly Ile Ala Asp Thr Gly Ile Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Leu Asp Val Ile Ser Pro Phe
225                 230                 235                 240

Glu Glu Arg Val Lys Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Asp Leu Val Pro Gln Met Ala Pro Asn Trp His Tyr Leu His
            275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Gln Gly Ala Tyr Glu
                325
```

<210> SEQ ID NO 105
<211> LENGTH: 326
<212> TYPE: PRT
<213> ORGANISM: Mycobacterium scrofulaceum

<400> SEQUENCE: 105

```
Met Ser Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
            20                  25                  30

Ala Leu Asn Tyr Pro Glu Ala Trp Gly Asp Glu Asp Arg Arg Val Ala
        35                  40                  45

Asp Ala Ile Asp Arg Leu Asn Glu Leu Lys Ser Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95
```

-continued

```
Leu Tyr Thr Tyr Asn Asp Val Pro Phe Arg Phe His Tyr Glu Gly Pro
            100                 105                 110

Gly Gly Leu Leu Asp Gly Pro Glu Ile Met Thr Glu Met Phe Val Arg
            115                 120                 125

Asp Ile Glu Gln Gly Ile Ala Asp Thr Gly Ile Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Leu Asp Val Ile Ser Pro Phe
225                 230                 235                 240

Glu Glu Arg Val Lys Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Asp Leu Val Pro Gln Met Ala Pro Asn Trp His Tyr Leu His
            275                 280                 285

Ile His Asn Asp Val Ile Pro Ala Leu Lys Glu Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ala Tyr Glu
                325

<210> SEQ ID NO 106
<211> LENGTH: 326
<212> TYPE: PRT
<213> ORGANISM: Mycobacterium marinum

<400> SEQUENCE: 106

Met Ser Ala Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
            20                  25                  30

Ala Gln Asn Tyr Pro Glu Ala Trp Gly Asp Glu Glu Lys Arg Val Ala
            35                  40                  45

Asp Ala Ile Thr Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Ile Ala Ala Ala Thr Asp Leu Asn Ile Val Val Ala Thr Gly
                85                  90                  95

Leu Tyr Thr Tyr Asn Asp Val Pro Tyr Arg Phe His Tyr Gln Gly Pro
            100                 105                 110

Gly Gly Met Leu Asp Gly Pro Glu Ile Met Thr Asp Met Phe Val Arg
            115                 120                 125
```

-continued

```
Asp Ile Glu Gln Gly Ile Ala Asp Thr Gly Val Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Thr His Lys Arg Thr Gly Val Pro Ile Ser
                165                 170                 175

Thr His Thr His Ala Gly Leu Arg Arg Gly Leu Glu Gln Gln Arg Ile
                180                 185                 190

Phe Glu Glu Glu Gly Val Asp Leu Ser Arg Val Ile Ile Gly His Ser
            195                 200                 205

Gly Asp Ser Thr Asp Val Gly Tyr Leu Glu Glu Leu Ile Ala Ala Gly
    210                 215                 220

Ser Tyr Leu Gly Met Asp Arg Phe Gly Ile Asp Leu Ile Leu Pro Phe
225                 230                 235                 240

Glu Asp Arg Val Ser Ile Val Ala Thr Met Cys Glu Arg Gly His Ala
                245                 250                 255

Asp Lys Met Val Leu Ser His Asp Ala Asn Cys Tyr Phe Asp Ala Leu
            260                 265                 270

Pro Glu Glu Leu Thr Ala Val Ala Thr Pro Asn Trp His Tyr Leu His
            275                 280                 285

Ile His Asn Asp Val Ile Pro Ala Leu Lys Glu Arg Gly Val Thr Asp
    290                 295                 300

Glu Gln Val His Thr Met Leu Val Asp Asn Pro Arg Arg Ile Phe Glu
305                 310                 315                 320

Arg Gln Gly Gly Tyr Gln
                325
```

```
<210> SEQ ID NO 107
<211> LENGTH: 325
<212> TYPE: PRT
<213> ORGANISM: Mycobacterium sp. E2497

<400> SEQUENCE: 107

Met Leu Glu Leu Asn Thr Ala Arg Gly Pro Ile Asp Thr Ala Asp Leu
1               5                   10                  15

Gly Val Thr Leu Met His Glu His Val Phe Ile Met Thr Thr Glu Ile
                20                  25                  30

Ala Leu Asn Tyr Pro Glu Ala Trp Gly Asp Glu Glu Lys Arg Val Ala
            35                  40                  45

Asp Ala Ile Ala Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Asp Leu Asn Ile Val Val Ala Thr Gly
                85                  90                  95

Leu Tyr Thr Tyr Asn Asp Ile Pro Phe Arg Phe His Tyr Glu Gly Pro
                100                 105                 110

Gly Gly Met Leu Gly Gly Pro Glu Ile Met Thr Asp Met Phe Val Lys
            115                 120                 125

Asp Ile Glu Gln Gly Ile Ala Asp Thr Gly Val Lys Ala Gly Ile Leu
    130                 135                 140

Lys Cys Ala Thr Asp Glu Pro Gly Ile Thr Pro Gly Val Glu Arg Val
145                 150                 155                 160
```

Leu Arg Ala Val Ala Gln Ala His Lys Arg Thr Gly Val Pro Ile Ser
            165                 170                 175

Thr His Thr His Ala Gly Leu Arg Arg Gly Leu Glu Gln Gln Arg Ile
            180                 185                 190

Phe Glu Glu Glu Gly Val Asp Leu Thr Arg Val Val Ile Gly His Ser
            195                 200                 205

Gly Asp Ser Thr Asp Ile Gly Tyr Leu Glu Glu Leu Ile Ala Ala Gly
    210                 215                 220

Ser Tyr Leu Gly Met Asp Arg Phe Gly Leu Asp Val Ile Ser Pro Phe
225                 230                 235                 240

Glu Glu Arg Val Lys Ile Val Ala Gln Met Cys Glu Arg Gly His Ala
            245                 250                 255

Asp Lys Met Val Leu Ser His Asp Ala Asn Cys Tyr Phe Asp Ala Leu
            260                 265                 270

Pro Glu Glu Leu Val Pro Gln Met Ala Pro Asn Trp His Tyr Leu His
            275                 280                 285

Ile His Asn Asp Val Ile Pro Ala Leu Lys Gln Arg Gly Val Thr Asp
    290                 295                 300

Glu Gln Leu His Thr Met Leu Val Asp Asn Pro Arg Arg Ile Phe Glu
305                 310                 315                 320

Arg Gln Gly Ala Tyr
            325

<210> SEQ ID NO 108
<211> LENGTH: 325
<212> TYPE: PRT
<213> ORGANISM: Mycobacterium simiae

<400> SEQUENCE: 108

Met Ser Glu Leu Asn Thr Ala Arg Gly Ala Ile Asp Thr Ala Asp Leu
1               5                   10                  15

Gly Val Thr Leu Met His Glu His Val Phe Ile Met Thr Thr Glu Ile
            20                  25                  30

Ala Gln Asn Tyr Pro Glu Ala Trp Gly Asp Glu Glu Lys Arg Val Ala
        35                  40                  45

Asp Ala Ile Ala Arg Leu Asn Glu Leu Lys Ala Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
            85                  90                  95

Ile Tyr Thr Tyr Asn Asp Val Pro Phe Arg Phe His Tyr Glu Gly Pro
            100                 105                 110

Gly Gly Met Leu Asp Gly Pro Glu Ile Met Thr Glu Met Phe Val Arg
            115                 120                 125

Asp Ile Glu Gln Gly Ile Ala Asp Thr Gly Val Lys Ala Gly Ile Leu
    130                 135                 140

Lys Cys Ala Thr Asp Glu Pro Gly Ile Thr Pro Gly Val Glu Arg Val
145                 150                 155                 160

Leu Arg Ala Val Ala Gln Ala His Lys Arg Thr Gly Val Pro Ile Ser
            165                 170                 175

Thr His Thr His Ala Gly Leu Arg Arg Gly Leu Asp Gln Gln Lys Ile
            180                 185                 190

```
Phe Asp Glu Glu Gly Val Asp Leu Thr Arg Val Val Ile Gly His Ser
        195                 200                 205

Gly Asp Ser Thr Asp Val Gly Tyr Leu Glu Glu Leu Ile Ala Ala Gly
        210                 215                 220

Ser Tyr Leu Gly Met Asp Arg Phe Gly Leu Asp Val Ile Ser Pro Phe
225                 230                 235                 240

Glu Glu Arg Val Lys Ile Val Ala Gln Met Cys Glu Arg Gly His Ala
                245                 250                 255

Asp Lys Met Val Leu Ser His Asp Ala Asn Cys Tyr Phe Asp Ala Leu
                260                 265                 270

Pro Glu Glu Leu Val Pro Gln Leu Ala Pro Asn Trp His Tyr Leu His
                275                 280                 285

Ile His Asn Asp Val Ile Pro Ala Leu Lys Glu Arg Gly Val Thr Asp
        290                 295                 300

Glu Gln Leu His Thr Met Leu Val Asp Asn Pro Arg Arg Ile Phe Glu
305                 310                 315                 320

Arg Thr Gly Ala Tyr
                325

<210> SEQ ID NO 109
<211> LENGTH: 326
<212> TYPE: PRT
<213> ORGANISM: Mycobacterium marinum
<220> FEATURE:
<221> NAME/KEY: misc_feature
<222> LOCATION: (84)..(84)
<223> OTHER INFORMATION: Xaa can be any naturally occurring amino acid

<400> SEQUENCE: 109

Met Ser Ala Leu Asn Thr Ala Arg Gly Pro Ile Asp Thr Ala Asp Leu
1               5                   10                  15

Gly Val Thr Leu Met His Glu His Val Phe Ile Met Thr Thr Glu Val
                20                  25                  30

Ala Gln Asn Tyr Pro Glu Ala Trp Gly Asp Glu Glu Lys Arg Val Ala
        35                  40                  45

Asp Ala Ile Thr Arg Leu Asn Glu Leu Lys Ser Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Ile Xaa Ala Ala Thr Asp Leu Asn Ile Val Val Ala Thr Gly
                85                  90                  95

Leu Tyr Thr Tyr Asn Asp Val Pro Tyr Arg Phe His Tyr Gln Gly Pro
            100                 105                 110

Gly Gly Met Leu Asp Gly Pro Glu Ile Met Thr Asp Met Phe Val Arg
            115                 120                 125

Asp Ile Glu Gln Gly Ile Ala Asp Thr Gly Val Lys Ala Gly Ile Leu
        130                 135                 140

Lys Cys Ala Thr Asp Glu Pro Gly Ile Thr Pro Gly Val Glu Arg Val
145                 150                 155                 160

Leu Arg Ala Val Ala Gln Thr His Lys Arg Thr Gly Val Pro Ile Ser
                165                 170                 175

Thr His Thr His Ala Gly Leu Arg Arg Gly Leu Glu Gln Gln Arg Ile
            180                 185                 190

Phe Glu Glu Glu Gly Val Asp Leu Ser Arg Val Ile Ile Gly His Ser
        195                 200                 205
```

-continued

```
Gly Asp Ser Thr Asp Val Gly Tyr Leu Glu Glu Leu Ile Ala Ala Gly
    210                 215                 220

Ser Tyr Leu Gly Met Asp Arg Phe Gly Ile Asp Leu Ile Leu Pro Phe
225                 230                 235                 240

Glu Asp Arg Val Asn Ile Val Ala Thr Met Cys Glu Arg Gly His Ala
                245                 250                 255

Asp Lys Met Val Leu Ser His Asp Ala Asn Cys Tyr Phe Asp Ala Leu
                260                 265                 270

Pro Glu Glu Leu Thr Ala Val Ala Thr Pro Asn Trp His Tyr Leu His
            275                 280                 285

Ile His Asn Asp Val Ile Pro Ala Leu Lys Glu Arg Gly Val Thr Asp
    290                 295                 300

Glu Gln Val His Thr Met Leu Val Asp Asn Pro Arg Arg Ile Phe Glu
305                 310                 315                 320

Arg Gln Gly Gly Tyr Gln
                325
```

```
<210> SEQ ID NO 110
<211> LENGTH: 326
<212> TYPE: PRT
<213> ORGANISM: Mycobacterium sp. E796

<400> SEQUENCE: 110

Met Pro Glu Leu Asn Thr Ala Arg Gly Ala Ile Asp Thr Ala Asp Leu
1               5                   10                  15

Gly Val Thr Leu Met His Glu His Val Phe Ile Met Thr Thr Glu Ile
                20                  25                  30

Ala Leu Asn Tyr Pro Glu Ala Trp Gly Asp Glu Asp Gln Arg Val Ala
            35                  40                  45

Asp Ala Val Asn Arg Leu Asn Glu Leu Lys Ser Arg Gly Val Asp Thr
    50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Arg Phe His Tyr Leu Gly Pro
                100                 105                 110

Gly Thr Gln Leu Asp Gly Pro Glu Ile Met Thr Asp Met Phe Val Arg
            115                 120                 125

Asp Ile Glu Glu Gly Ile Ala Asp Thr Gly Ile Lys Ala Gly Ile Leu
    130                 135                 140

Lys Cys Ala Thr Asp Glu Pro Gly Val Thr Pro Gly Val Glu Arg Val
145                 150                 155                 160

Leu Arg Ala Val Ala Gln Ala His Lys Arg Thr Gly Val Pro Ile Ser
                165                 170                 175

Thr His Thr His Ala Gly Thr Arg Arg Gly Leu Glu Gln Gln Arg Ile
            180                 185                 190

Phe Glu Glu Glu Gly Val Asp Leu Ser Arg Val Val Ile Gly His Ser
            195                 200                 205

Gly Asp Ser Thr Asp Leu Asp Tyr Leu Glu Glu Leu Ile Gly Asn Gly
    210                 215                 220

Ser Tyr Ile Gly Met Asp Arg Phe Gly Ile Asp Val Tyr Leu Pro Phe
225                 230                 235                 240

Glu Asp Arg Val Asn Thr Val Ala Arg Met Cys Glu Arg Gly His Ala
                245                 250                 255
```

```
Asp Lys Met Val Leu Ser His Asp Ala Asn Cys Tyr Phe Asp Ala Leu
        260             265             270

Pro Glu Glu Leu Leu Pro Val Ala Ala Pro Asn Trp His Tyr Leu His
        275             280             285

Ile His Asn Asp Val Ile Pro Ala Leu Lys Glu Arg Gly Val Thr Asp
    290             295             300

Glu Gln Leu His Thr Met Leu Val Asp Asn Pro Arg Arg Ile Phe Glu
305             310             315             320

Arg Gln Gly Ala Tyr Ser
            325
```

```
<210> SEQ ID NO 111
<211> LENGTH: 277
<212> TYPE: PRT
<213> ORGANISM: Mycobacterium tuberculosis (positions 1-277 of SEQ ID
      NO: 1)

<400> SEQUENCE: 111

Met Ile Ser Glu Phe Pro Glu Leu Asn Thr Ala Arg Gly Pro Ile Asp
1               5               10              15

Thr Ala Asp Leu Gly Val Thr Leu Met His Glu His Val Phe Ile Met
        20              25              30

Thr Thr Glu Ile Ala Gln Asn Tyr Pro Glu Ala Trp Gly Asp Glu Asp
        35              40              45

Lys Arg Val Ala Gly Ala Ile Ala Arg Leu Gly Glu Leu Lys Ala Arg
    50              55              60

Gly Val Asp Thr Ile Val Asp Leu Thr Val Ile Gly Leu Gly Arg Tyr
65              70              75              80

Ile Pro Arg Ile Ala Arg Val Ala Ala Ala Thr Glu Leu Asn Ile Val
            85              90              95

Val Ala Thr Gly Leu Tyr Thr Tyr Asn Asp Val Pro Phe Tyr Phe His
        100             105             110

Tyr Leu Gly Pro Gly Ala Gln Leu Asp Gly Pro Glu Ile Met Thr Asp
        115             120             125

Met Phe Val Arg Asp Ile Glu His Gly Ile Ala Asp Thr Gly Ile Lys
    130             135             140

Ala Gly Ile Leu Lys Cys Ala Thr Asp Glu Pro Gly Leu Thr Pro Gly
145             150             155             160

Val Glu Arg Val Leu Arg Ala Val Ala Gln Ala His Lys Arg Thr Gly
            165             170             175

Ala Pro Ile Ser Thr His Thr His Ala Gly Leu Arg Arg Gly Leu Asp
        180             185             190

Gln Gln Arg Ile Phe Ala Glu Glu Gly Val Asp Leu Ser Arg Val Val
        195             200             205

Ile Gly His Cys Gly Asp Ser Thr Asp Val Gly Tyr Leu Glu Glu Leu
    210             215             220

Ile Ala Ala Gly Ser Tyr Leu Gly Met Asp Arg Phe Gly Val Asp Val
225             230             235             240

Ile Ser Pro Phe Gln Asp Arg Val Asn Ile Val Ala Arg Met Cys Glu
            245             250             255

Arg Gly His Ala Asp Lys Met Val Leu Ser His Asp Ala Cys Cys Tyr
        260             265             270

Phe Asp Ala Leu Pro
        275
```

<210> SEQ ID NO 112
<211> LENGTH: 277
<212> TYPE: PRT
<213> ORGANISM: Mycobacterium tuberculosis (positions 1-277 of SEQ ID
      NO: 2)

<400> SEQUENCE: 112

Met Ile Ser Glu Phe Pro Glu Leu Asn Thr Ala Arg Gly Pro Ile Asp
1               5                   10                  15

Thr Ala Asp Leu Gly Val Thr Leu Met His Glu His Val Phe Ile Met
            20                  25                  30

Thr Thr Glu Ile Ala Gln Asn Tyr Pro Glu Ala Trp Gly Asp Glu Asp
        35                  40                  45

Lys Arg Val Ala Gly Ala Ile Ala Arg Leu Val Glu Leu Lys Ala Arg
    50                  55                  60

Gly Val Asp Thr Ile Val Asp Leu Thr Val Ile Gly Leu Gly Arg Tyr
65                  70                  75                  80

Ile Pro Arg Ile Ala Arg Val Ala Ala Ala Thr Glu Leu Asn Ile Val
                85                  90                  95

Val Ala Thr Gly Leu Tyr Thr Tyr Asn Asp Val Pro Phe Tyr Phe His
            100                 105                 110

Tyr Leu Gly Pro Gly Ala Gln Leu Asp Gly Pro Glu Ile Met Thr Asp
        115                 120                 125

Met Phe Val Arg Asp Ile Glu His Gly Ile Ala Asp Thr Gly Ile Lys
    130                 135                 140

Ala Gly Ile Leu Lys Cys Ala Thr Asp Glu Pro Gly Leu Thr Pro Gly
145                 150                 155                 160

Val Glu Arg Val Leu Arg Ala Val Ala Gln Ala His Lys Arg Thr Gly
                165                 170                 175

Ala Pro Ile Ser Thr His Thr His Ala Gly Leu Arg Arg Gly Leu Asp
            180                 185                 190

Gln Gln Arg Ile Phe Ala Glu Glu Gly Val Asp Leu Ser Arg Val Val
        195                 200                 205

Ile Gly His Cys Gly Asp Ser Thr Asp Val Gly Tyr Leu Glu Glu Leu
    210                 215                 220

Ile Ala Ala Gly Ser Tyr Leu Gly Met Asp Arg Phe Gly Val Asp Val
225                 230                 235                 240

Ile Ser Pro Phe Gln Asp Arg Val Asn Ile Val Ala Arg Met Cys Glu
                245                 250                 255

Arg Gly His Ala Asp Lys Met Val Leu Ser His Asp Ala Cys Cys Tyr
            260                 265                 270

Phe Asp Ala Leu Pro
        275

<210> SEQ ID NO 113
<211> LENGTH: 277
<212> TYPE: PRT
<213> ORGANISM: Mycobacterium tuberculosis (positions 1-277 of SEQ ID
      NO: 3)

<400> SEQUENCE: 113

Met Ile Ser Glu Phe Pro Glu Leu Asn Thr Ala Arg Gly Pro Ile Asp
1               5                   10                  15

Thr Ala Asp Leu Gly Val Thr Leu Met His Glu His Val Phe Ile Met
            20                  25                  30

-continued

```
Thr Thr Glu Ile Ala Gln Asn Tyr Pro Glu Ala Trp Gly Asp Glu Asp
        35                  40                  45

Lys Arg Val Ala Gly Ala Ile Ala Arg Leu Gly Glu Leu Lys Ala Arg
    50                  55                  60

Gly Val Asp Thr Ile Val Asp Leu Thr Val Ile Gly Leu Gly Arg Tyr
65                  70                  75                  80

Ile Pro Arg Ile Ala Arg Val Ala Ala Ala Thr Glu Leu Asn Ile Val
                85                  90                  95

Val Ala Thr Gly Leu Tyr Thr Tyr Asn Asp Val Pro Phe Tyr Phe His
                100                 105                 110

Tyr Leu Gly Pro Gly Ala Gln Leu Asp Gly Pro Glu Ile Met Thr Asp
        115                 120                 125

Met Phe Val Arg Asp Ile Glu His Gly Ile Ala Asp Thr Gly Ile Lys
    130                 135                 140

Ala Gly Ile Leu Lys Cys Ala Thr Asp Glu Pro Gly Leu Thr Pro Gly
145                 150                 155                 160

Val Glu Arg Val Leu Arg Ala Val Ala Gln Ala Tyr Lys Arg Thr Gly
                165                 170                 175

Ala Pro Ile Ser Thr His Thr His Ala Gly Leu Arg Arg Gly Leu Asp
                180                 185                 190

Gln Gln Arg Ile Phe Ala Glu Glu Gly Val Asp Leu Ser Arg Val Val
        195                 200                 205

Ile Gly His Cys Gly Asp Ser Thr Asp Val Gly Tyr Leu Glu Glu Leu
    210                 215                 220

Ile Ala Ala Gly Ser Tyr Leu Gly Met Asp Arg Phe Gly Val Asp Val
225                 230                 235                 240

Ile Ser Pro Phe Gln Asp Arg Val Asn Ile Val Ala Arg Met Cys Glu
                245                 250                 255

Arg Gly His Ala Asp Lys Met Val Leu Ser His Asp Ala Cys Cys Tyr
                260                 265                 270

Phe Asp Ala Leu Pro
        275
```

```
<210> SEQ ID NO 114
<211> LENGTH: 306
<212> TYPE: PRT
<213> ORGANISM: Artificial Sequence
<220> FEATURE:
<223> OTHER INFORMATION: synthetic
```

```
<400> SEQUENCE: 114
```

```
Val Asp Glu Ala Leu Lys Asp Ala Gln Thr Asn Ser Ser Ser Asn Asn
1               5                   10                  15

Asn Asn Asn Asn Asn Asn Asn Asn Leu Gly Ile Glu Gly Arg Ile Ser
                20                  25                  30

Glu Phe Pro Glu Leu Asn Thr Ala Arg Gly Pro Ile Asp Thr Ala Asp
        35                  40                  45

Leu Gly Val Thr Leu Met His Glu His Val Phe Ile Met Thr Thr Glu
    50                  55                  60

Ile Ala Gln Asn Tyr Pro Glu Ala Trp Gly Asp Glu Asp Lys Arg Val
65                  70                  75                  80

Ala Gly Ala Ile Ala Arg Leu Gly Glu Leu Lys Ala Arg Gly Val Asp
                85                  90                  95

Thr Ile Val Asp Leu Thr Val Ile Gly Leu Gly Arg Tyr Ile Pro Arg
                100                 105                 110
```

```
Ile Ala Arg Val Ala Ala Ala Thr Glu Leu Asn Ile Val Val Ala Thr
        115                 120                 125

Gly Leu Tyr Thr Tyr Asn Asp Val Pro Phe Tyr Phe His Tyr Leu Gly
        130                 135                 140

Pro Gly Ala Gln Leu Asp Gly Pro Glu Ile Met Thr Asp Met Phe Val
145                 150                 155                 160

Arg Asp Ile Glu His Gly Ile Ala Asp Thr Gly Ile Lys Ala Gly Ile
                165                 170                 175

Leu Lys Cys Ala Thr Asp Glu Pro Gly Leu Thr Pro Gly Val Glu Arg
                180                 185                 190

Val Leu Arg Ala Val Ala Gln Ala His Lys Arg Thr Gly Ala Pro Ile
        195                 200                 205

Ser Thr His Thr His Ala Gly Leu Arg Arg Gly Leu Asp Gln Gln Arg
        210                 215                 220

Ile Phe Ala Glu Glu Gly Val Asp Leu Ser Arg Val Val Ile Gly His
225                 230                 235                 240

Cys Gly Asp Ser Thr Asp Val Gly Tyr Leu Glu Glu Leu Ile Ala Ala
                245                 250                 255

Gly Ser Tyr Leu Gly Met Asp Arg Phe Gly Val Asp Val Ile Ser Pro
                260                 265                 270

Phe Gln Asp Arg Val Asn Ile Val Ala Arg Met Cys Glu Arg Gly His
                275                 280                 285

Ala Asp Lys Met Val Leu Ser His Asp Ala Cys Cys Tyr Phe Asp Ala
        290                 295                 300

Leu Pro
305
```

```
<210> SEQ ID NO 115
<211> LENGTH: 273
<212> TYPE: PRT
<213> ORGANISM: Mycobacterium tuberculosis (positions 1-273 of SEQ ID
      NO: 50)
<220> FEATURE:
<221> NAME/KEY: misc_feature
<222> LOCATION: (145)..(145)
<223> OTHER INFORMATION: Xaa can be any naturally occurring amino acid

<400> SEQUENCE: 115
```

```
Met Pro Glu Leu Asn Thr Ala Arg Gly Pro Ile Asp Thr Ala Asp Leu
1                   5                   10                  15

Gly Val Thr Leu Met His Glu His Val Phe Ile Met Thr Thr Glu Ile
                20                  25                  30

Ala Gln Asn Tyr Pro Glu Ala Trp Gly Asp Glu Asp Lys Arg Val Ala
        35                  40                  45

Gly Ala Ile Ala Arg Leu Gly Glu Leu Lys Ala Arg Gly Val Asp Thr
        50                  55                  60

Ile Val Asp Leu Thr Val Ile Gly Leu Gly Arg Tyr Ile Pro Arg Ile
65                  70                  75                  80

Ala Arg Val Ala Ala Ala Thr Glu Leu Asn Ile Val Val Ala Thr Gly
                85                  90                  95

Leu Tyr Thr Tyr Asn Asp Val Pro Phe Tyr Phe His Tyr Leu Gly Pro
                100                 105                 110

Gly Ala Gln Leu Asp Gly Pro Glu Ile Met Thr Asp Met Phe Val Arg
        115                 120                 125

Asp Ile Glu His Gly Ile Ala Asp Thr Gly Ile Lys Ala Gly Ile Leu
        130                 135                 140
```

-continued

```
Xaa Cys Ala Thr Asp Glu Pro Gly Leu Thr Pro Gly Val Glu Arg Val
145             150             155             160

Leu Arg Ala Val Ala Gln Ala His Lys Arg Thr Gly Ala Pro Ile Ser
            165             170             175

Thr His Thr His Ala Gly Leu Arg Arg Gly Leu Asp Gln Gln Arg Ile
            180             185             190

Phe Ala Glu Glu Gly Val Asp Leu Ser Arg Val Val Ile Gly His Cys
        195             200             205

Gly Asp Ser Thr Asp Val Gly Tyr Leu Glu Glu Leu Ile Ala Ala Gly
    210             215             220

Ser Tyr Leu Gly Met Asp Arg Phe Gly Val Asp Val Ile Ser Pro Phe
225             230             235             240

Gln Asp Arg Val Asn Ile Val Ala Arg Met Cys Glu Arg Gly His Ala
            245             250             255

Asp Lys Met Val Leu Ser His Asp Ala Cys Cys Tyr Phe Asp Ala Leu
            260             265             270

Pro

<210> SEQ ID NO 116
<211> LENGTH: 9
<212> TYPE: PRT
<213> ORGANISM: Artificial Sequence
<220> FEATURE:
<223> OTHER INFORMATION: SYNTHETIC

<400> SEQUENCE: 116

Ala Trp Arg His Pro Gln Phe Gly Gly
1               5
```